(12) United States Patent
Fonquerna Pou et al.

(10) Patent No.: US 7,622,480 B2
(45) Date of Patent: Nov. 24, 2009

(54) AZAINDOLYLPIPERIDINE DERIVATIVES AS ANTIHISTAMINIC AND ANTIALLERGIC AGENTS

(75) Inventors: Silvia Fonquerna Pou, Barcelona (ES); Luis Miguel Pages Santacana, Barcelona (ES); Carlos Puig Duran, Barlceona (ES); Jose Manuel Prieto Soto, Barcelona (ES); Aranzazu Cardus Figueras, Barcelona (ES)

(73) Assignee: Laboratorios Almirall S.A., Barcelona (ES)

( * ) Notice: Subject to any disclaimer, the term of this patent is extended or adjusted under 35 U.S.C. 154(b) by 573 days.

(21) Appl. No.: 10/509,279

(22) PCT Filed: Apr. 1, 2003

(86) PCT No.: PCT/EP03/03377

§ 371 (c)(1),
(2), (4) Date: May 5, 2005

(87) PCT Pub. No.: WO03/082867

PCT Pub. Date: Oct. 9, 2003

(65) Prior Publication Data

US 2005/0176751 A1  Aug. 11, 2005

(30) Foreign Application Priority Data

Apr. 1, 2002  (ES) ................. 200200753

(51) Int. Cl.
*A61K 31/437* (2006.01)
*C07D 401/04* (2006.01)

(52) U.S. Cl. ...................... 514/300; 546/113

(58) Field of Classification Search ............. 546/113, 546/199; 548/464; 514/300
See application file for complete search history.

(56) References Cited

FOREIGN PATENT DOCUMENTS

| WO | WO 98/20875 | * | 5/1998 |
|----|-------------|---|--------|
| WO | WO 00 75130 A2 | | 12/2000 |
| WO | WO 02 14317 A1 | | 2/2002 |
| WO | WO 02 20013 A2 | | 3/2002 |
| WO | WO 02 36589 A2 | | 5/2002 |
| WO | WO02/051837 A2 | | 7/2002 |
| WO | WO02/079151 A1 | | 10/2002 |

* cited by examiner

*Primary Examiner*—Bernard Dentz
*Assistant Examiner*—David E Gallis
(74) *Attorney, Agent, or Firm*—Finnegan, Henderson, Farabow, Garrett & Dunner, LLP

(57) ABSTRACT

This invention is directed to selective antagonists of $H_1$ histamine receptors having the general formula (I); to processes for their preparation; to pharmaceutical compositions comprising them; and to their use in therapy.

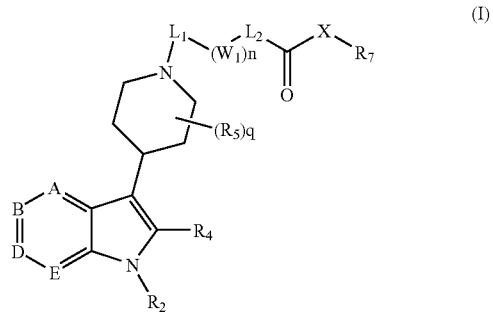

21 Claims, No Drawings

AZAINDOLYLPIPERIDINE DERIVATIVES AS ANTIHISTAMINIC AND ANTIALLERGIC AGENTS

This application is a national stage filing under 35 U.S.C. 371 of International Application No. PCT/EP03/03377, filed on Apr. 1, 2003. This application claims the benefit of priority under 35 U.S.C. § 119 to Spanish Patent Application No. P200200753 filed on Apr. 1, 2002.

The present invention relates to novel azaindolylpiperidine compounds and pharmaceutically acceptable salts thereof. These compounds are antagonists of $H_1$ histamine receptors and are thus useful for the treatment of bronchial asthma, allergic rhinitis, conjunctivitis, dermatitis, urticaria and other allergic diseases.

Due to their capability to cross the blood-brain barrier, most commercial antihistamines produce adverse side-effects such as sleepiness and sedation. Antihistamines having an indolylpiperidine core have been disclosed in EP 224919 and WO 0075130. It has now been found that replacing one or more carbon atoms of the six-membered ring of the indolyl moiety by the corresponding number of nitrogen atoms dramatically decreases the capability of the compounds to cross the blood-brain barrier, diminishing the occurrence of side effects.

Thus, the present invention provides certain novel azaindolylpiperidine compounds having improved antihistaminic and antiallergic activities and a reduced occurrence of sedative and cardiovascular side effects. Azaindolylpiperidines of a different general structure have been disclosed in EP 842934 as serotonin agonists.

Further objectives of the present invention are to provide a method for preparing said compounds; pharmaceutical compositions comprising an effective amount of said compounds; the use of the compounds in the manufacture of a medicament for the treatment of diseases susceptible of being improved by antagonism of $H_1$ histamine receptors, such as allergic diseases; and methods of treatment of diseases susceptible to amelioration by antagonism of $H_1$ histamine receptors, such as allergic diseases, comprising the administration of the compounds of the invention to a subject in need of treatment.

In accordance with the present invention, novel azaindolylpiperidine compounds represented by the general formula I are provided

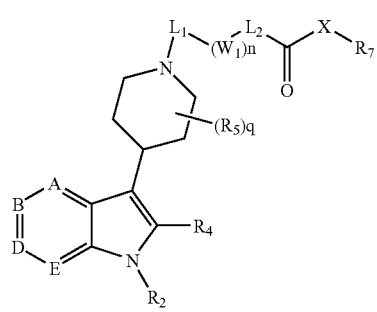

wherein:

each of A, B, D and E independently represents a nitrogen atom or a —$CR_1$— group, with the proviso that at least one of A, B, D or E is a nitrogen atom;

$R_1$ represents a hydrogen or a halogen atom, or a hydroxy, alkyl, alkenyl, alkynyl, alkoxy, alkylthio, amino, monalkyalmino, dialkylamino, nitro, cyano or acylamino group, the hydrocarbon chains of these groups being optionally substituted by one or more, for example, 1, 2, 3 or 4, further substituents selected from halogen, hydroxy, oxo, alkoxy, alkylthio, acylamino, phenyl, alkoxycarbonyl, amino, monoalkylamino, dialkylamino and hydroxycarbonyl groups;

$R_2$ represents a hydrogen atom or a group of formula $L_3$—$(W_2)_p$;

$L_1$, $L_2$ and $L_3$ each independently represents a single bond or an acyclic, straight or branched, saturated or unsaturated hydrocarbon chain having from 1 to 10 carbon atoms, optionally containing 1 to 3 groups independently selected from —S—, —O— or —$NR_3$—, which replace a corresponding number of non-adjacent carbon atoms, and wherein $R_3$ is selected from hydrogen or an alkyl group; the hydrocarbon chain being optionally substituted by one or more, for example, 1, 2, 3 or 4, substituents selected from halogen, hydroxy, oxo, acylamino, phenyl, alkoxycarbonyl and hydroxycarbonyl groups;

$R_4$ and $R_5$ each independently represents a hydrogen or halogen atom, a hydroxy group, or a group selected from one of alkyl, alkoxy, alkenyl, alkynyl or phenyl, which is optionally substituted by one or more, for example, 1, 2, 3 or 4, substituents selected from, halogen, hydroxy, oxo, alkoxy, alkylthio, acylamino, phenyl, alkoxycarbonyl, amino, monoalkylamino, dialkylamino and hydroxycarbonyl groups;

X represents —O— or —$NR_6$—;

$R_6$ and $R_7$ each independently represents a hydrogen atom, a group of formula —$(CH_2)_m$—$W_3$ or a group selected from alkyl, alkenyl or alkynyl, which is optionally substituted by one or more, for example 1, 2, 3 or 4, substituents selected from —$(CH_2)_m$—$W_3$, —O—$(CH_2)_m$—$W_3$, —S—$(CH_2)_m$—$W_3$, —$NR_3$—$(CH_2)_m$—$W_3$, hydroxy, oxo, halogen, alkoxy, alkylthio, amino, monoalkylamino, and dialkylamino; the alkyl chains in the alkoxy, alkylthio, monoalkylamino and dialkylamino substituents being optionally substituted by one or more, for example 1, 2, 3 or 4, further substituents selected from —$(CH_2)_m$—$W_3$, hydroxy, oxo, halogen, alkoxy, alkylthio, amino, monoalkylamino and dialkylamino groups;

$W_1$, $W_2$ and $W_3$ each independently represents a 3- to 7-membered aromatic or non-aromatic cyclic group containing from 0 to 4 heteroatoms selected from N, O and S, which is optionally fused to another 3- to 7-membered aromatic or non-aromatic cyclic group containing from 0 to 4 heteroatoms selected from N, O and S; the cyclic groups being optionally substituted by one or more, for example 1, 2, 3 or 4, substituents selected from halogen, alkyl, alkenyl, alkynyl, aryl, cycloalkyl, heteroaryl, heterocyclyl, hydroxy, alkylenedioxy, alkoxy, alkylthio, amino, monoalkylamino, dialkylamino, nitro, cyano, oxo, hydroxycarbonyl, alkylcarbonyl, alkoxycarbonyl, acylamino, carbamoyl, and alkylcarbamoyl groups; the hydrocarbon chains and the cyclic moieties of these substituents being optionally substituted by one or more, for example 1, 2, 3 or 4, further substituents selected from halogen, hydroxy, oxo, alkoxy, alkylthio, acylamino, carbamoyl, alkylcarbamoyl, hydroxyalkoxy, phenyl, alkoxycarbonyl, amino, monoalkylamino, dialkylamino and hydroxycarbonyl groups;

m is an integer from 0 to 4;

n and p are independently 0 or 1;

q is an integer from 1 to 9;

and N-oxides and pharmaceutically acceptable salts thereof; with the proviso that the compound of formula I is not the tert-butyl ester of 4-(5-amino-1H-pyrrolo[3,2-b]pyridin-3-yl)piperidine-1-carboxylic acid.

As used herein, a hydrocarbon chain is a straight or branched non-cyclic sequence of carbon atoms covalently linked by single, double or triple bonds, and substituted by hydrogen atoms, for example straight or branched alkyl, alkenyl or alkynyl groups, moieties or chains. Typically, the hydrocarbon chains, contain from 1 to 10 carbon atoms.

As used herein, an alkyl, alkenyl or alkynyl group or moiety is a straight or branched group or moiety. Typically it is a $C_1$-$C_{10}$ group or moiety, for example a $C_1$-$C_6$ group or moiety, preferably a $C_1$-$C_4$ group or moiety. Examples include methyl, ethyl, i-propyl, n-propyl, n-butyl, t-butyl, allyl, 2-propenyl and 3-butynyl. Where a group contains two or more alkyl, alkenyl or alkynyl moieties, these moieties may be the same or different. When an alkyl, alkenyl or alkynyl chain, group or moiety carries 2 or more substituents, the substituents may be the same or different.

As used herein, an alkylene group or moiety is a divalent alkyl moiety typically having from 1 to 6, for example from 1 to 4, carbon atoms. Examples of $C_1$-$C_4$ alkylene groups include methylene, ethylene, propylene and butylene groups. When an alkylene or alkylenedioxy group is present as a substituent on another group it shall be deemed to be a single substituent, rather than a group formed by two substituents.

As used herein, the alkyl chains present in the alkoxy, alkylthio, monoalkylamino, dialkylamino, hydroxyalkoxy, alkylcarbonyl, alkoxycarbonyl, alkylcarbamoyl and alkylenedioxy groups are typically straight or branched alkyl chains containing from 1 to 6 carbon atoms.

As used herein, an acyl group or moiety typically has from 2 to 7 carbon atoms. Thus, it is typically a group of formula —COR wherein R is a hydrocarbon chain group having from 1 to 6 carbon atoms. Preferably, it is a group of formula —COR wherein R is a $C_1$-$C_6$ alkyl group.

As used herein, an aryl group or moiety is typically a $C_6$-$C_{10}$ aryl group or moiety such as phenyl or naphthyl. Phenyl is preferred. When an aryl group or moiety carries 2 or more substituents, the substituents may be the same or different.

As used herein, a heteroaryl group or moiety is typically a 5- to 10-membered aromatic ring, such as a 5- or 6-membered ring, containing at least one heteroatom selected from O, S and N. Examples include pyridyl, pyrazinyl, pyrimidinyl, pyridazinyl, furanyl, oxadiazolyl, oxazolyl, imidazolyl, thiazolyl, thiadiazolyl, thienyl, pyrazolidinyl, pyrrolyl and pyrazolyl groups. Oxadiazolyl, oxazolyl, pyridyl, pyrrolyl, imidazolyl, thiazolyl, thiadiazolyl, thienyl, furanyl, pyrazinyl and pyrimidinyl groups are preferred. When a heteroaryl group or moiety carries 2 or more substituents, the substituents may be the same or different.

As used herein, a cycloalkyl group typically has from 3 to 6 carbon atoms. Examples include cyclopropyl, cyclobutyl, cyclopentyl and cyclohexyl. It is preferably cyclopropyl, cyclopentyl or cyclohexyl. When a cycloalkyl group carries 2 or more substituents, the substituents may be the same or different.

As used herein, a heterocyclyl group is typically a non-aromatic, saturated or unsaturated $C_3$-$C_{10}$ carbocyclic ring in which one or more, for example 1, 2, 3 or 4 of the carbon atoms are replaced by a heteroatom selected from N, O and S. Saturated heterocyclyl groups are preferred. Examples of suitable heterocyclyl groups include piperidinyl, piperazinyl, morpholinyl, 4,5-dihydro-oxazolyl, 3-aza-tetrahydrofuranyl, imidazolidinyl and pyrrolidinyl groups. Where a heterocyclyl group carries 2 or more substituents, the substituents may be the same or different.

As used herein, some of the atoms, groups, moieties, chains or cycles present in the general structures of the invention are "optionally substituted". This means that these atoms, groups, moieties, chains or cycles can be either unsubstituted or substituted by one or more, for example 1, 2, 3 or 4, substituents, whereby the hydrogen atoms bound to the unsubstituted atoms, groups, moieties, chains or cycles are replaced by chemically acceptable atoms, groups, moieties, chains or cycles.

As used herein, when one of the substituents is a halogen atom, it is preferably a chlorine, fluorine or bromine atom.

Compounds of the formula (I) containing one or more chiral centre may be used in enantiomerically or diastereoisomerically pure form, or in the form of a mixture of isomers.

As used herein, an N-oxide is formed from the pyridines present in the molecule, using a convenient oxidising agent.

As used herein, a pharmaceutically acceptable salt is a salt with a pharmaceutically acceptable acid or base. Pharmaceutically acceptable acids include both inorganic acids, for example hydrochloric, sulphuric, phosphoric, diphosphoric, hydrobromic and nitric acid and organic acids, for example citric, fumaric, maleic, malic, ascorbic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, aralkyl amines and heterocyclic amines.

Preferred compounds of the invention are those wherein only one or two of A, B, D or E is a nitrogen atom. When only one is nitrogen it is preferably at positions D or E. When two of them are nitrogen they are preferably at positions A and D or B and E.

Also preferred are compounds wherein each $R_1$ is independently selected from a hydrogen or halogen atom or an alkyl, or alkoxy group. More preferably, $R_1$ is hydrogen, chlorine; fluorine or methoxy and still more preferably $R_1$ is hydrogen.

Further preferred compounds are those wherein each of $L_1$, $L_2$ and $L_3$ independently represents a single bond or an alkyl, oxyalkyl, aminoalkyl, thioalkyl or alkoxyalkyl group. When $L_1$ or $L_2$ represents an oxyalkyl, aminoalkyl or thioalkyl group the orientation of the group is typically such that the alkyl moiety is attached to the N atom. Most preferred are compounds wherein $L_1$ is an alkyl, oxyalkyl; aminoalkyl or thioalkyl group, for example methyl, ethyl, n-propyl, oxyethyl, oxypropyl, aminoethyl or thioethyl; $L_2$ is a single bond or an alkyl group, for example methyl or ethyl; and $L_3$ is a single bond or an alkyl, oxyalkyl or alkoxyalkyl group, for example methyl, ethyl, n-propyl, isopropyl, butyl, oxyethyl, methoxyethyl or ethoxyethyl.

$W_1$ is preferably an aromatic monocyclic group which is optionally substituted by one or more, for example, 1, 2, 3 or 4, substituents selected from halogen atoms, alkyl or alkoxy groups. More preferably $W_1$ is selected from a phenyl, furanyl or thienyl group, which is optionally substituted by one or more, for example 1, 2, 3 or 4, substituents selected from halogen, alkyl or alkoxy, such as fluorine, chlorine, bromine, methyl or methoxy. Most preferred are compounds wherein $W_1$ is a phenyl group optionally substituted by one or more, for example 1, 2, 3 or 4, substituents selected from halogen, alkyl or alkoxy, such as fluorine, chlorine, bromine, methyl or methoxy.

Alternatively, in yet other preferred compounds of the invention n is 0.

$W_2$ is preferably a cycloalkyl group, for example cyclopropyl, cyclobutyl or cyclopentyl, a phenyl group, or a 5- or 6-membered heterocyclyl group, for example a tetrahydropyranyl, furanyl, thienyl, pyrrolyl, pyridinyl, oxetanyl or dioxanyl group. More preferably $W_2$ is selected from cyclopropyl, phenyl, pyridinyl, furanyl and thienyl.

$W_2$ is optionally substituted by one or more, for example 1, 2, 3 or 4, substituents selected from halogen, alkyl or alkoxy, such as fluorine, chlorine, bromine, methyl, ethyl or methoxy.

Alternatively, in yet other preferred compounds of the invention p is 0 or $R_2$ is hydrogen.

In the preferred compounds of the invention $R_4$ and $R_5$ each independently represents a hydrogen or halogen atom, a $C_1$-$C_4$ alkyl group or a phenyl group, which is optionally substituted by one or more, for example 1, 2, 3 or 4, substituents selected from halogen, alkyl or alkoxy, such as fluorine, chlorine, bromine, methyl, ethyl or methoxy. Most preferably $R_4$ and $R_5$ are both hydrogen.

In the most preferred compounds of the invention X is —O— and $R_7$ is hydrogen, alkyl or a —$(CH_2)_n$-phenyl group, wherein n is 0 or 1, for example methyl, ethyl, tert-butyl, phenyl or benzyl, excluding the tert-butyl ester of 4-(5-amino-1H-pyrrolo[3,2-b]pyridin-3-yl)-piperidine-1-carboxylic acid.

Alternatively, when X is —N—$R_6$, the most preferred compounds are those wherein $R_6$ and $R_7$ are independently hydrogen, alkyl or a —$(CH_2)_n$-phenyl group, wherein n is 0 or 1, for example methyl, ethyl, tert-butyl, phenyl or benzyl.

Particular individual compounds of the invention include:
1. 3-{4-[1-(2-methoxyethyl)-1H-pyrrolo[2,3-b]pyridin-3-yl]piperidin-1-ylmethyl}benzoic acid
2. 3-[4-(1-furan-3-ylmethyl-1H-pyrrolo[2,3-b]pyridin-3-yl)piperidin-1-ylmethyl]benzoic acid
3. 2-{2-[4-(1-furan-3-ylmethyl-1H-pyrrolo[2,3-b]pyridin-3-yl)piperidine-1-yl]ethoxy}benzoic acid
4. 3-{4-[1-(2-ethoxyethyl)-1H-pyrrolo[2,3-b]pyridin-3-yl]piperidin-1-ylmethyl}benzoic acid
5. 5-{4-[1-(2-ethoxyethyl)-1H-pyrrolo[2,3-b]pyridin-1-ylmethyl}-2-methoxybenzoic acid
6. 2-(2-{4-[1-(2-ethoxyethyl)-1H-pyrrolo[2,3-b]pyridin-3-yl]piperidin-1-ylethoxy)benzoic acid
7. 5-[4-(1-furan-3-ylmethyl-1H-pyrrolo[2,3-b]pyridin-3-yl)-piperidin-1-ylmethyl]-2-methoxybenzoic acid
8. 2-{2-[4-(1-furan-2-ylmethyl-1H-pyrrolo[2,3-b]pyridin-3-yl)-piperidin-1-yl]-ethoxy}-benzoic acid
9. 3-[4-(1-furan-2-ylmethyl-1H-pyrrolo[2,3-b]pyridin-3-yl)piperidin-1-ylmethyl]-benzoic acid
10. 5-[4-(1-furan-2-ylmethyl-1H-pyrrolo[2,3-b]pyridin-3-yl)piperidin-1-ylmethyl]-2methoxy-benzoic acid
11. 2-{2-[4-(1-thiophen-2-ylmethyl-1H-pyrrolo[2,3-b]pyridin-3-yl)-piperidin-1-yl]-ethoxy}benzoic acid
12. 3-[4-(1-thiophen-2-ylmethyl-1H-pyrrolo[2,3-b]pyridin-3-yl)piperidin-1-ylmethyl]-benzoic acid
13. 2-methoxy-5-[4-(1-thiophen-2-ylmethyl-1H-pyrrolo[2,3-b]pyridin-3-yl)-piperidin-1-ylmethyl]-benzoic acid
14. 2-{2-[4-(1-thiophen-3-ylmethyl-1H-pyrrolo[2,3-b]pyridin-3-yl)-piperidin-1-yl]-ethoxy}-benzoic acid
15. 3-[4-(1-thiophen-3-ylmethyl-1H-pyrrolo[2,3-b]pyridin-3-yl)-piperidin-1-ylmethyl]-benzoic acid
16. 2-methoxy-5-[4-(1-thiophen-3-ylmethyl-1H-pyrrolo[2,3-b]pyridin-3-yl)piperidin-1-ylmethyl]-benzoic acid
17. 2-(2-{4-[1-(5-chlorothiophen-2-ylmethyl)-1H-pyrrolo[2,3-b]pyridin-3-yl]-piperidin-1-yl}-ethoxy)-benzoic acid
18. 3-{4-[1-(5-chlorothiophen-2-ylmethyl)-1H-pyrrolo[2,3-b]pyridin-3-yl]-piperidin-1-ylmethyl}-benzoic acid
19. 5-{4-[1-(5-chlorothiophen-2-ylmethyl)-1H-pyrrolo[2,3-b]pyridin-3-yl]-piperidin-1-ylmethyl}2-methoxybenzoic acid
20. 2-(2-{4-[1-(2-methoxyethyl)-1H-pyrrolo[2,3-b]pyridin-3-yl]-piperidin-1-yl}-ethoxy)-benzoic acid
21. 2-methoxy-5-{4-[1-(2-methoxyethyl)-1H-pyrrolo[2,3-b]pyridin-3-yl]-piperidin-1-ylmethyl}-benzoic acid
22. 2,4-dimethoxy-3-{4-[1-(2-methoxyethyl)-1H-pyrrolo[2,3-b]pyridin-3-yl]-piperidin-1-ylmethyl}-benzoic acid
23. 2-methoxy-6-(2-{4-[1-(2-methoxyethyl)-1H-pyrrolo[2,3-b]pyridin-3-yl]-piperidin-1-yl}-ethoxy)benzoic acid
24. 5-[4-(1-butyl-1H-pyrrolo[2,3-b]pyridin-3-yl)piperidin-1-ylmethyl]-2-methoxybenzoic acid
25. 2-{2-[4-(1-butyl-1H-pyrrolo[2,3-b]pyridin-3-yl)piperidin-1-yl]-ethoxy}-benzoic acid
26. 3-[4-(1-butyl-1H-pyrrolo[2,3-b]pyridin-3-yl)piperidin-1-ylmethyl]-benzoic acid
27. 2-{2-[4-(1-cyclopropylmethyl-1H-pyrrolo[2,3-b]pyridin-3-yl)-piperidin-1-yl]-ethoxy}-benzoic acid
28. 3-[4-(1-cyclopropylmethyl-1H-pyrrolo[2,3-b]pyridin-3-yl)-piperidin-1-ylmethyl]-benzoic acid
29. 5-[4-(1-cyclopropylmethyl-1H-pyrrolo[2,3-b]pyridin-3-yl)-piperidin-1-ylmethyl]-2-methoxybenzoic acid
30. 2-{2-[4-(1-isopropyl-1H-pyrrolo[2,3-b]pyridin-3-yl)-piperidin-1-yl]-ethoxy}-benzoic acid
31. 3-[4-(1-isopropyl-1H-pyrrolo[2,3-b]pyridin-3-yl)piperidin-1-ylmethyl]-benzoic acid
32. 5-[4-(1-isopropyl-1H-pyrrolo[2,3-b]pyridin-3-yl)-piperidin-1-ylmethyl]-2-methoxybenzoic acid
33. 2-(2-{4-[1-(4-fluorobenzyl)-1H-pyrrolo[2,3-b]pyridin-3-yl]-piperidin-1-yl}ethoxy)-benzoic acid
34. 4-{4-[1-(4-fluorobenzyl)-1H-pyrrolo[2,3-b]pyridin-3-yl]-piperidin-1-yl}-butyric acid
35. (2-{4-[1-(4-fluorobenzyl)-1H-pyrrolo[2,3-b]pyridin-3-yl]-piperidin-1-yl}-ethoxy)-acetic acid
36. 2-(2-{4-[1-(2-ethoxyethyl)-1H-pyrrolo[2,3-b]pyridin-3-yl]-piperidin-1-yl}-ethoxy)-4-methoxybenzoic acid
37. 2-(2-{4-[1-(2-ethoxyethyl)-1H-pyrrolo[2,3-b]pyridin-3-yl]-piperidin-1-yl}-ethoxy)-3-methoxybenzoic acid
38. 4-chloro-2-(2-{4-[1-(2-ethoxyethyl)-1H-pyrrolo[2,3-b]pyridin-3-yl]-piperidin-1-yl}-ethoxy)benzoic acid
39. 5-{4-[1-(2-ethoxyethyl)-1H-pyrrolo[2,3-b]pyridin-3-yl]-piperidin-1-ylmethyl}-2-fluorobenzoic acid
40. 3-{4-[1-(2-ethoxyethyl)-1H-pyrrolo[2,3-b]pyridin-3-yl]-piperidin-1-ylmethyl}-2-methoxybenzoic acid
41. 3-{4-[1-(2-ethoxyethyl)-1H-pyrrolo[2,3-b]pyridin-3-yl]-piperidin-1-ylmethyl}-2,4-dimethoxybenzoic acid
42. 2-(2-{4-[1-(2-ethoxyethyl)-1H-pyrrolo[2,3-b]pyridin-3-yl]-piperidin-1-yl}-ethoxy)-6-methoxybenzoic acid
43. 2-{2-[4-(1-furan-3-ylmethyl-1H-pyrrolo[2,3-b]pyridin-3-yl)piperidin-1-yl]-ethoxy}-4-methoxybenzoic acid
44. 4-chloro-2-{2-[4-(1-furan-3-ylmethyl-1H-pyrrolo[2,3-b]pyridin-3-yl)-piperidin-1-yl]-ethoxy}-benzoic acid
45. 2-fluoro-5-[4-(1-furan-3-ylmethyl-1H-pyrrolo[2,3-b]pyridin-3-yl)-piperidin-1-ylmethyl]-benzoic acid
46. 2-{2-[4-(1-furan-3-ylmethyl-1H-pyrrolo[2,3-b]pyridin-3-yl)-piperidin-1-yl]-ethoxy}-3-methoxybenzoic acid
47. 3-[4-(1-furan-3-ylmethyl-1H-pyrrolo[2,3-b]pyridin-3-yl)-piperidin-1-ylmethyl]-2-methoxybenzoic acid
48. 3-[4-(1-furan-3-ylmethyl-1H-pyrrolo[2,3-b]pyridin-3-yl)piperidin-1-ylmethyl]-2,4-dimethoxybenzoic acid
49. 2-{2-[4-(1-furan-3-ylmethyl-1H-pyrrolo[2,3-b]pyridin-3-yl)-piperidin-1-yl]-ethoxy}-6-methoxybenzoic acid
50. 2-{2-[4-(1-furan-2-ylmethyl-1H-pyrrolo[2,3-b]pyridin-3-yl)-piperidin-1-yl]-ethoxy}-4-methoxybenzoic acid
51. 2-{2-[4-(1-furan-2-ylmethyl-1H-pyrrolo[2,3-b]pyridin-3-yl)-piperidin-1-yl]-ethoxy}-3-methoxybenzoic acid 52. 4-chloro-2-{2-[4-(1-furan-2-ylmethyl-1H-pyrrolo[2,3-b]pyridin-3-yl)piperidin-1-yl]-ethoxy}-benzoic acid
53. 2-fluoro-5-[4-(1-furan-2-ylmethyl-1H-pyrrolo[2,3-b]pyridin-3-yl)-piperidin-1-ylmethyl]-benzoic acid
54. 2-(2-{4-[1-(5-chlorothiophen-2-ylmethyl)-1H-pyrrolo[2,3-b]pyridin-3-yl]-piperidin-1-yl}-ethoxy)-3-methoxybenzoic acid
55. 2-(2-{4-[1-(5-chlorothiophen-2-ylmethyl)-1H-pyrrolo[2,3-b]pyridin-3-yl]-piperidin-1-yl}-ethoxy)-4-methoxybenzoic acid
56. 4-chloro-2-(2-{4-[1-(5-chlorothiophen-2-ylmethyl)-1H-pyrrolo[2,3-b]pyridin-3-yl]-piperidin-1-yl}-ethoxy)benzoic acid
57. 5-{4-[1-(5-chlorothiophen-2-ylmethyl)-1H-pyrrolo[2,3-b]pyridin-3-yl]-piperidin-1-ylmethyl}-2-fluorobenzoic acid
58. 3-{4-[1-(5-chlorothiophen-2-ylmethyl)-1H-pyrrolo[2,3-b]pyridin-3-yl]-piperidin-1-ylmethyl}-2-methoxybenzoic acid
59. 3-{4-[1-(5-chlorothiophen-2-ylmethyl)-1H-pyrrolo[2,3-b]pyridin-3-yl]-piperidin-1-ylmethyl}-2,4-dimethoxybenzoic acid
60. 2-(2-{4-[1-(5-chlorothiophen-2-ylmethyl)-1H-pyrrolo[2,3-b]pyridin-3-yl]-piperidin-1-yl}-ethoxy)-6-methoxybenzoic acid
61. 2-{2-[4-(1-butyl-1H-pyrrolo[2,3-b]pyridin-3-yl)piperidin-1-yl]-ethoxy}-4-methoxybenzoic acid
62. 2-{2-[4-(1-butyl-1H-pyrrolo[2,3-b]pyridin-3-yl)piperidin-1-yl]-ethoxy}-3-methoxybenzoic acid
63. 2-{2-[4-(1-butyl-1H-pyrrolo[2,3-b]pyridin-3-yl)-piperidin-1-yl]-ethoxy}-4-chlorobenzoic acid
64. 5-[4-(1-butyl-1H-pyrrolo[2,3-b]pyridin-3-yl)-piperidin-1-ylmethyl]-2-fluorobenzoic acid
65. 3-[4-(1-butyl-1H-pyrrolo[2,3-b]pyridin-3-yl)piperidin-1-ylmethyl]-2-methoxybenzoic acid
66. 3-[4-(1-butyl-1H-pyrrolo[2,3-b]pyridin-3-yl)-piperidin-1-ylmethyl]-2,4-dimethoxybenzoic acid
67. 2-{2-[4-(1-butyl-1H-pyrrolo[2,3-b]pyridin-3-yl)-piperidin-1-yl]-ethoxy}-6-methoxybenzoic acid
68. 2-{2-[4-(1-pyridin-2-ylmethyl-1H-pyrrolo[2,3-b]pyridin-3-yl)-piperidin-1-yl]-ethoxy}-benzoic acid
69. 4-[4-(1-pyridin-2-ylmethyl-1H-pyrrolo[2,3-b]pyridin-3-yl)-piperidin-1-yl]-butyric acid
70. 2-(2-{4-[1-(2-ethoxyethyl)-1H-pyrrolo[2,3-c]pyridin-3-yl]-piperidin-1-yl}-ethoxy)-benzoic acid
71. 2-(2-{4-[1-(2-ethoxyethyl)-1H-pyrrolo[2,3-c]pyridin-3-yl]-piperidin-1-yl}-ethoxy)-3-methoxybenzoic acid
72. 2-(2-{4-[1-(2-ethoxyethyl)-1H-pyrrolo[2,3-c]pyridin-3-yl]-piperidin-1-yl}-ethoxy)-4-methoxybenzoic acid
73. 4-chloro-2-(2-{4-[1-(2-ethoxyethyl)-1H-pyrrolo[2,3-c]pyridin-3-yl]-piperidin-1-yl}-ethoxy)-benzoic acid
74. 5-{4-[1-(2-ethoxyethyl)-1H-pyrrolo[2,3-c]pyridin-3-yl]-piperidin-1-ylmethyl}2-methoxybenzoic acid
75. 4-bromo-3-{4-[1-(2-ethoxyethyl)-1H-pyrrolo[2,3-c]pyridin-3-yl]-piperidin-1-ylmethyl}-benzoic acid
76. 2-{2-[4-(1-furan-3-ylmethyl-1H-pyrrolo[2,3-c]pyridin-3-yl)-piperidin-1-yl]-ethoxy}-4-methoxybenzoic acid
77. 2-{2-[4-(1-furan-3-ylmethyl-1H-pyrrolo[2,3]pyridin-3-yl)-piperidin-1-yl]-ethoxy}-benzoic acid
78. 5-[4-(1-furan-3-ylmethyl-1H-pyrrolo[2,3-c]pyridin-3-yl)-piperidin-1-ylmethyl]-2-methoxybenzoic acid
79. 3-[4-(1-furan-3-ylmethyl-1H-pyrrolo[2,3-c]pyridin-3-yl)piperidin-1-ylmethyl]-2-methoxybenzoic acid
80. 4-chloro-2-{2-[4-(1-furan-3-ylmethyl-1H-pyrrolo[2,3-c]pyridin-3-yl)piperidin-1-yl]-ethoxy}-benzoic acid
81. 2-{2-[4-(1-butyl-1H-pyrrolo[2,3-c]pyridin-3-yl)-piperidin-1-yl]-ethoxy}-benzoic acid
82. 2-{2-[4-(1-butyl-1H-pyrrolo[2,3-c]pyridin-3-yl)-piperidin-1-yl]-ethoxy}-3-methoxy-benzoic acid
83. 2-{2-[4-(1-butyl-1H-pyrrolo[2,3]pyridin-3-yl)piperidin-1-yl]-ethoxy}-4-methoxy-benzoic acid
84. 2-{2-[4-(1-butyl-1H-pyrrolo[2,3-c]pyridin-3-yl)piperidin-1-yl]-ethoxy}-4-chlorobenzoic acid
85. 5-[4-(1-butyl-1H-pyrrolo[2,3-c]pyridin-3-yl)-piperidin-1-ylmethyl]-2-methoxybenzoic acid
86. 4-bromo-3-[4-(1-butyl-1H-pyrrolo[2,3-c]pyridin-3-yl)piperidin-1-ylmethyl]-benzoic acid
87. 3-[4-(1-butyl-1H-pyrrolo[2,3-c]pyridin-3-yl)-piperidin-1-ylmethyl]-benzoic acid
88. 5-{4-[1-(5-chlorothiophen-2-ylmethyl)-1H-pyrrolo[2,3-c]pyridin-3-yl]-piperidin-1-ylmethyl}-2-methoxybenzoic acid
89. 2-(2-{4-[1-(5-chlorothiophen-2-ylmethyl)-1H-pyrrolo[2,3-c]pyridin-3-yl]-piperidin-1-yl}ethoxy)-benzoic acid
90. 2-(2-{4-[1-(5-chlorothiophen-2-ylmethyl)-1H-pyrrolo[2,3-]pyridin-3-yl]-piperidin-1-yl}-ethoxy)-3-methoxybenzoic acid
91. 2-(2-{4-[1-(5-chlorothiophen-2-ylmethyl)-1H-pyrrolo[2,3-c]pyridin-3-yl]-piperidin-1-yl}ethoxy)-4-methoxybenzoic acid
92. 4-chloro-2-(2-{4-[1-(5-chlorothiophen-2-ylmethyl)-1H-pyrrolo[2,3-c]pyridin-3-yl]-piperidin-1-yl}-ethoxy)-benzoic acid
93. (2-{4-[1-(5-chlorothiophen-2-ylmethyl)-1H-pyrrolo[2,3-c]pyridin-3-yl]-piperidin-1-yl}-ethoxy)acetic acid
94. 2-{2-[4-(1-thiophen-2-ylmethyl-1H-pyrrolo[2,3-c]pyridin-3-yl)piperidin-1-yl]-ethoxy}-benzoic acid
95. 2-{2-[4-(1-furan-2-ylmethyl-1H-pyrrolo[2,3-c]pyridin-3-yl)-piperidin-1-yl]-ethoxy}-benzoic acid
96. 5-[4-(1-furan-2-ylmethyl-1H-pyrrolo[2,3-c]pyridin-3-yl)-piperidin-1-ylmethyl]-2-methoxybenzoic acid
97. 4-methoxy-2-{2-[4-(1-thiophen-3-ylmethyl-1H-pyrrolo[2,3-c]pyridin-3-yl)piperidin-1-yl]-ethoxy}-benzoic acid
98. 2-methoxy-5-[4-(1-thiophen-3-ylmethyl-1H-pyrrolo[2,3-c]pyridin-3-yl)piperidin-1-ylmethyl]-benzoic acid
99. 2-(2-{4-[1-(2-methoxyethyl)-1H-pyrrolo[2,3-c]pyridin-3-yl]-piperidin-1-yl}-ethoxy)-benzoic acid
100. 2-(2-{4-[1-(2-ethoxyethyl)-7-hydroxy-1H-pyrrolo[2,3-b]pyridin-3-yl]-piperidin-1-yl}-ethoxy)-benzoic acid
101. 3-{4-[1-(2-methoxyethyl)-1H-pyrrolo[2,3-b]pyridin-3-yl]piperidin-1-ylmethyl}benzoic acid ethyl ester
102. 3-[4-(1-furan-3-ylmethyl-1H-pyrrolo[2,3-b]pyridin-3-yl)piperidin-1-ylmethyl]benzoic acid methyl ester
103. 2-{2-[4-(1-furan-3-ylmethyl-1H-pyrrolo[2,3-b]pyridin-3-yl)piperidine-1-yl]ethoxy}benzoic acid methyl ester
104. 3-{4-[1-(2-ethoxyethyl)-1H-pyrrolo[2,3-b]pyridine-3-yl]piperidin-1-ylmethyl}benzoic acid methyl ester
105. 5-{4-[1-(2-ethoxyethyl)-1H-pyrrolo[2,3-b]pyridine-1-ylmethyl}-2-methoxybenzoic acid ethyl ester
106. 2-(2-{4-[1-(2-ethoxyethyl)-1H-pyrrolo[2,3-b]pyridin-3-yl]piperidin-1-ylethoxy)benzoic acid methyl ester
107. 5-[4-furan-3-ylmethyl-1H-pyrrolo[2,3-b]pyridin-3-yl)-piperidin-1-ylmethyl]-2-methoxybenzoic acid ethyl ester
108. 2-(2-{4-[1-(5-chlorothiophen-2-ylmethyl)-1H-pyrrolo[2,3-b]pyridin-3-yl]-piperidin-1-yl}ethoxy)-benzoic acid methyl ester
109. 5-[4-(1-butyl-1H-pyrrolo[2,3-b]pyridin-3-yl)piperidin-1-ylmethyl]-2-methoxybenzoic acid ethyl ester
110. 2-(2-{4-[1-(2-ethoxyethyl)-1H-pyrrolo[2,3-b]pyridin-3-yl]-piperidin-1-yl}-ethoxy)-4-methoxybenzoic acid methyl ester
111. 2-(2-{4-[1-(2-ethoxyethyl)-1H-pyrrolo[2,3-c]pyridin-3-yl]-piperidin-1-yl}-ethoxy)-benzoic acid methyl ester
112. 2-{2-[4-(1-furan-3-ylmethyl-1H-pyrrolo[2,3]pyridin-3-yl)-piperidin-1-yl]-ethoxy}-4-methoxy-benzoic acid methyl ester
113. 2-{2-[4-(1-butyl-1H-pyrrolo[2,3-c]pyridin-3-yl)piperidin-1-yl]-ethoxy}-benzoic acid methyl ester 114. 5-{4-[1-(5-chlorothiophen-2-ylmethyl)-1H-pyrrolo[2,3-c]pyridin-3-yl]-piperidin-1-ylmethyl}-2-methoxybenzoic acid ethyl ester
115. 4-(1-furan-3-ylmethyl-1H-pyrrolo[2,3-b]pyridin-3-yl)piperidine-1 carboxylic acid tert-butyl ester
116. 4-(1-furan-3-ylmethyl-1H-pyrrolo[2,3-b]pyridin-3-yl)piperidine-1-carboxylic acid ethyl ester
117. 4-[1-(5-chlorothiophen-2-ylmethyl)-1H-pyrrolo[2,3-b]pyridin-3-yl]-piperidine-1-carboxylic acid tert-butyl ester
118. 4-(1-butyl-1H-pyrrolo[2,3-b]pyridin-3-yl)piperidine-1-carboxylic acid ethyl ester
119. 4-[1-(2-ethoxyethyl)-1H-pyrrolo[2,3-c]pyridin-3-yl]-piperidine-1-carboxylic acid ethyl ester
120. 4-(1-furan-3-ylmethyl-1H-pyrrolo[2,3-c]pyridin-3-yl)piperidine-1-carboxylic acid ethyl ester
121. 4-(1-butyl-1H-pyrrolo[2,3-c]pyridin-3-yl)piperidine-1-carboxylic acid ethyl ester
122. 4-[1-(5-chlorothiophen-2-ylmethyl)-1H-pyrrolo[2,3-c]pyridin-3-yl]-piperidine-1-carboxylic acid ethyl ester
123. 4-(1-furan-3-ylmethyl-1H-pyrrolo[2,3-b]pyridin-3-yl)piperidine-1-carboxylic acid tert-butyl ester
124. 4-(1-furan-3-ylmethyl-1H-pyrrolo[2,3-b]pyridin-3-yl)-piperidine-1 carboxylic acid ethyl ester
125. 4-[1-(chlorothiophen-2-ylmethyl)-1H-pyrrolo[2,3-b]pyridin-3-yl]-piperidine-1-carboxylic acid tert-butyl ester
126. 4-(1-butyl-1H-pyrrolo[2,3-b]pyridin-3-yl)-piperidine-1-carboxylic acid ethyl ester
127. 4-[1-(2-ethoxyethyl)-1H-pyrrolo[2,3-c]pyridin-3-yl]-piperidine-1-carboxylic acid ethyl ester
128. 4-(1-furan-3-ylmethyl-1H-pyrrolo[2,3-c]pyridin-3-yl)-piperdine-1-carboxylic acid ethyl ester
129. 4-(1-butyl-1H-pyrrolo[2,3]pyridin-3-yl)-piperidine-1-carboxylic acid ethyl ester
130. 4-[1-(5-chlorothiophen-2-ylmethyl)-1H-pyrrolo[2,3-c]pyridin-3-yl]-piperidine-1-carboxylic acid ethyl ester
131. 3-(methyl-{2-[4-(1H-pyridin-2-ylmethyl-1H-pyrrolo[3,2-c]pyridin-3-yl)piperidin-1-yl]-ethyl}-amino)-benzoic acid
132. 6-[4-(1-thiophen-3-ylmethyl-1H-pyrrolo[2,3-c]pyridin-3-yl)piperidin-1-yl]-hexanoic acid
133. 3-[4-(1-butyl-1H-pyrrolo[3,2-c]pyridin-3-yl)piperidin-1-ylmethyl]-isonicotinic acid
134. 5-{4-[1-(2-[1,4]dioxan-2-yl-ethyl)-1H-pyrrolo[3,2-c]pyridin-3-yl]-piperidin-1-ylmethyl}2-fluorobenzoic acid
135. (E)-4-{4-[7-(4-fluoro-benzyl)-7H-pyrrolo[2,3-d]pyrimidin-5-yl]-piperidin-1-yl}-but-2-enoic acid
136. 5-(4-{7-[2-(4-methoxy-phenyl)ethyl]-7H-pyrrolo[2,3-d]pyrimidin-5-yl}-piperidin-1-ylmethyl)-furan-2-carboxylic acid
137. 4-bromo-3-[4-(7-oxy-1-propyl-1H-pyrrolo[2,3-b]pyridin-3-yl)-piperidin-1-ylmethyl]-benzoic acid
138. {2-[4-(4-chloro-1-thiophen-2-ylethyl-1H-pyrrolo[2,3-c]pyridin-3-yl)-piperidin-1-yl]-ethoxy}-acetic acid
139. 2-(2-{4-[7-fluoro-1-(2-methoxyethyl)-1H-pyrrolo[3,2-b]pyridin-3-yl]-piperidin-1-yl}-ethoxy)-thiophene-3-carboxylic acid
140. 2-(4-{2-[4-(2-methoxy-7H-pyrrolo[2,3-d]pyrimidin-5-yl)-piperidin-1-yl]-ethyl}-phenyl)-2-methyl-propionic acid
141. 5-[4-(1-furan-2-ylmethyl-1H-pyrrolo[2,3-b]pyridin-3-yl)-piperidin-1-yl]-pentanoic acid (4-trifluoromethyl-phenyl)amide
142. 3-[4-(3-{4-hydroxy-4-[5-methylsulfanyl-2-phenyl-1-(tetrahydro-furan-2-ylmethyl)-1H-pyrrolo[2,3-b]pyridin-3-yl]-piperidin-1-yl}-propyl)-furan-2-yl]-propionic acid benzyl ester
143. 1-[2-(2-{4-[1-(2-cyclopropylmethoxy-ethyl)-6,7-dimethoxy-1H-pyrrolo[3,2-b]pyridin-3-yl]-piperidin-1-yl}-ethylsulfanyl)ethyl]-piperidine-2-carboxylic acid
144. 2-{5-acetyl-2-[(3-{4-[4-(2-methoxy-ethoxy)methyl-7H-pyrrolo[2,3-d]pyrimidin-5-yl]-piperidin-1-yl}propyl)-methyl-amino]-phenoxy}-N,N-dimethyl-acetamide
145. (3-{3-[4-(2-bromo-7-isopropoxy-1H-pyrrolo[3,2-c]pyridin-3-yl)-2,2-dimethyl-piperidin-1-yl]-propanoyl}-5-chloro-phenoxy)acetic acid tert-butyl ester
146. 5-(2-{4-[4-dimethylamino-1-(2-ethylsulfanyl-ethyl)-7-fluoro-1H-pyrrolo[3,2-c]pyridin-3-yl]-piperidin-1-yl}-ethoxy)-N,N-dimethyl-nicotinamide
147. [7-{1-[(E)-4-(5-{1-[(1,1-diphenyl-methyl)carbamoyl]-1-methyl-ethyl}-furan-2-yl)-but-2-enyl]-piperidin-4-yl}5-(2-hydroxy-1-phenyl-ethyl)-5H-pyrrolo[3,2-d]pyrimidin-2-yl]-acetic acid ethyl ester In accordance with another embodiment, the present invention provides a method for preparing the novel azaindolylpiperidine compounds represented by formula I. The compounds of formula I can be prepared according to Scheme 1 starting from an intermediate of general formula IX wherein A, B, D, E, $R_2$, $R_4$, $R_5$ and q are as defined above.

Scheme 1

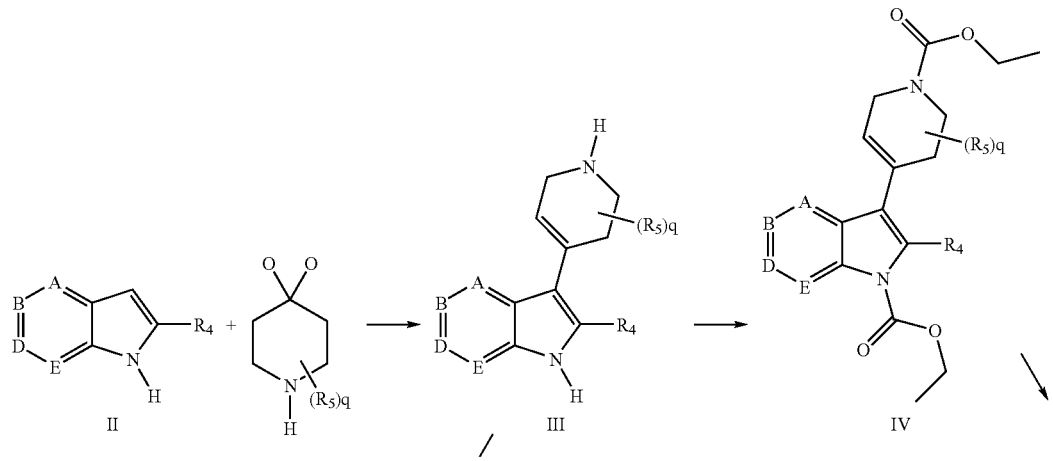

-continued
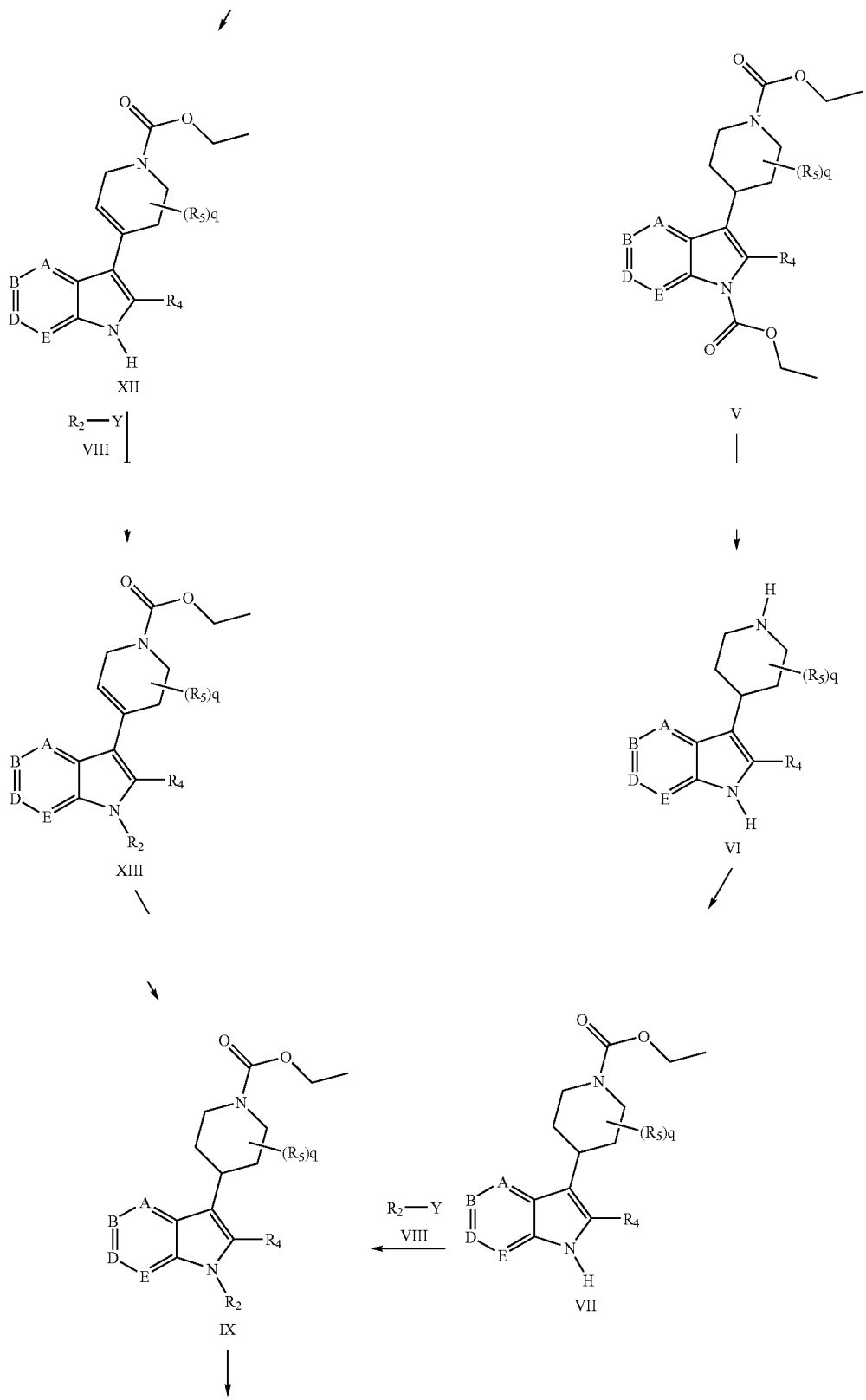

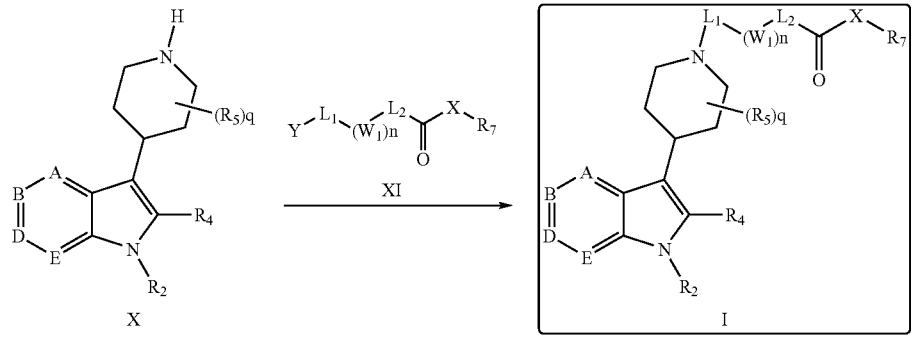

Compound IX is deprotected by boiling it in the presence of an excess of sodium or potassium hydroxide in an alcoholic solvent such as ethanol, isopropanol or n-butanol at a temperature between 80° C. and 180° C. This leads to a compound of general formula X, wherein A, B, D, E, $R_2$, $R_4$, $R_5$ and q are as defined above. Compounds of formula X are novel, with the exception of those wherein A is a nitrogen atom; D and E are both —CH—; $R_2$, $R_4$ and $R_5$ are all hydrogen; and B is a —$CR_1$— group, $R_1$ being an acylamino group. The novel compounds of formula X constitute a further embodiment of the invention.

Further alkylation of compound X with a reactive intermediate of general formula XI wherein $L_1$, $L_2$, $W_1$, n, X and $R_7$ are as defined above and Y is a leaving group, such as a chlorine or a bromine atom or a methane sulphonate, p-toluene sulphonate or a benzene sulphonate group, gives a compound of general formula I. This reaction is preferably carried out in an organic solvent such as toluene, dichloromethane, dioxane or methyl isobutylketone at a temperature between 25° C. and 140° C. in the presence of a base such as an alkali metal carbonate or bicarbonate, triethylamine or diisopropylethylamine. Occasionally, the solvent used is dimethylformamide.

Compounds of general formula I wherein X is an oxygen atom are treated with sodium or potassium hydroxide in a solvent such as methanol, ethanol or tetrahydrofuran at a temperature between 25° C. and 60° C. Further treatment with an inorganic acid such as hydrochloric acid provides the corresponding azaindolylpiperidine derivatives of general formula XIV wherein A, B, D, E, $L_1$, $L_2$, $R_2$ $R_4$, $R_5$, q, $W_1$ and n are as defined above (see Scheme 2)

Scheme 2

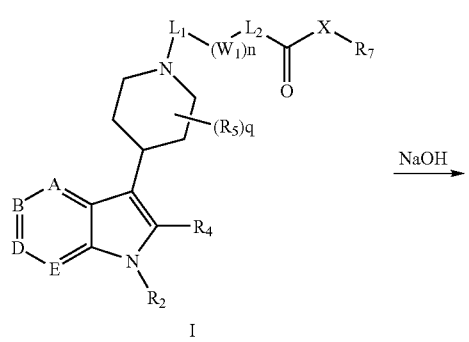

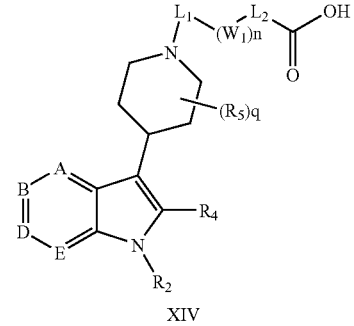

The intermediate of general formula IX can be prepared following two different pathways (see Scheme 1).

According to the first pathway a compound of general structure III wherein A, B, D, E, $R_4$, $R_5$ and q are as defined above, is treated with two equivalents of ethyl chloroformate in the presence of a base such as triethylamine or pyridine at a temperature between 0° C. and room temperature to give a compound of general formula IV wherein A, B, D, E, $R_4$, $R_5$ and q are as defined above.

Compound IV is hydrogenated using palladium or platinum oxide as a catalyst in a solvent such as ethanol or methanol in neutral or acidic conditions at a pressure between 2 and 3 bar, to provide a compound of general formula V wherein A, B, D, E, $R_4$, $R_5$ and q are as defined above.

Subsequent deprotection of the carbamate moieties of the compound of general formula V by boiling it in the presence of an excess of sodium or potassium hydroxide in an alcoholic solvent such as ethanol, isopropanol or n-butanol at a temperature between 80° C. and 180° C. gives a compound of formula VI wherein A, B, D, E, $R_4$, $R_5$ and q are as defined above.

The piperidine moiety of compound VI is reprotected using the same conditions as described above for preparing compound IV, giving a compound of general formula VII wherein A, B, D, E, $R_4$, $R_5$ and q are as defined above.

Alkylation of compound VII with a reactive intermediate of general formula VIII wherein $R_2$ is as defined above and Y is a leaving group, such as a iodine, chlorine or bromine atom or a methane sulphonate, p-toluenesulphonate or a benzenesulphonate group, gives a compound of general formula IX. This reaction is preferably carried out in an inert solvent such as dimethylformamide, tetrahydrofuran or ethyl ether at a temperature between 0° C. and 80° C. in the presence of an inorganic base such as sodium hydride or sodium amide.

Occasionally, the base used is potassium carbonate in the presence of copper and copper oxide.

According to an alternative pathway (see Scheme 1), a compound of general formula III wherein A, B, D, E, $R_4$, $R_5$ and q are as defined above, is treated with 1 equivalent of ethyl chloroformate in the presence of a base such as triethylamine or pyridine at a temperature between 0° C. and room temperature to give a compound of general formula XII wherein A, B, D, E, $R_4$, $R_5$ and q are as defined above.

Compound XII is alkylated with the reactive intermediate VIII, which is as defined above, to give a compound of general formula XIII wherein A, B, D, E, $R_2$, $R_4$, $R_5$ and q are as defined above. This reaction is preferably carried out in an inert solvent such as dimethylformamide, tetrahydrofuran or ethyl ether at a temperature between 0° C. and 80° C. in a presence of an inorganic base such as sodium hydride or sodium amide.

Compound XIII is hydrogenated using palladium or platinum oxide as a catalyst in a solvent such as methanol or ethanol in neutral or acidic conditions at a pressure between 2 and 3 bar, to lead to the compound of general formula IX.

The final products of formula I are purified by chromatography or by recrystallisation. Occasionally, the products are purified by preparative HPLC-MS, using a C-18 column.

The starting compounds of the general formula II are either commercially available or prepared following described procedures (*Heterocycles*, 1992, 34, 2379; *J. Heterocyclic Chem.* 1992, 29, 359); the azaindolylpiperidine derivatives of general formula III can be prepared from 4-piperidone as described in *J. Med. Chem.* 1992, 35, 4813.

The present invention will be further illustrated by the following Examples. These Examples are given by way of illustration only and are not to be construed as limiting.

TABLE 1

List of examples according to Scheme I

| Example | R1 | R2 | Mol. weight |
|---|---|---|---|
| 1 | | | 393.484 |
| 2 | | | 415.491 |
| 3 | | | 445.516 |
| 4 | | | 407.511 |
| 5 | | | 437.537 |
| 6 | | | 437.537 |

The sign (*) in the structures shows the point of attachment. It does not symbolise a carbon atom.

EXAMPLE 1

Preparation of 3-{4-[1-(2-methoxyethyl)-1H-pyrrolo [2,3-b]pyridin-3-yl]piperidin-1-ylmethyl}benzoic acid A. Preparation of 3-(1,2,3,6-tetrahydropyridin-4-yl)- 1H-pyrrolo[2,3-b]pyridine 0.5 g (4.23 mmol) of 7-azaindole and 1.95 g (12.7 mmol) of 4-piperidine monohydrate hydrochloride were added to an ice-cooled solution of 0.9 g (16.07 mmol) of potassium hydroxide in 15 ml of methanol. The mixture was warmed to room temperature and then refluxed for 18 hours. Once cooled to room temperature, the formed solid was isolated by suction filtration. The filtered solution was concentrated and the residue was dissolved in a mixture of water and dichloromethane. After the separation of the organic phase the aqueous phase was further extracted with dichloromethane. The organic phases were washed with water and brine, dried with magnesium sulphate, filtered and the solvent was removed under reduced pressure affording 0.65 g of a deep-red oil.

After treatment with ethyl ether, 0.36 g (77% of yield) of a yellowish solid were filtered off.

B. Preparation of 3-(1-ethoxycarbonyl-1,2,3,6-tetrahydro-pyridinyl)pyrrolo[2,3-b]pyridine-1-carboxylic acid ethyl ester 5.04 g (25.29 mmol) of 3-(1,2,3,6-tetrahydropyridinyl)-1H-pyrrolo[2,3-b]pyridine were solved in 45 ml of dichloromethane and 7.0 ml (50.59 mmol) of triethylamine were added to the solution. After cooling to 0° C., 5.0 ml (50.59 mmol) of ethyl chloroformate were added dropwise. The mixture was stirred at 0° C. for 6 hours and then washed with water and brine. The organic layer was separated and dried with magnesium sulphate. After removing the solvent under reduced pressure, 8.48 g (98% of yield) of an oil were obtained which crystallized at room temperature.

C. Preparation of 3-(1-ethoxycarbonyl-piperidin-4-yl)pyrrolo[2,3-b]pyridine-1-carboxylic acid ethyl ester 1.87 g of palladium, 10% (dry basis) on activated carbon (50% in water) were added over a solution of 8-48 g (24.7 mmol) of 3-(1-ethoxycarbonyl-1,2,3,6-tetrahydro-pyridinyl)pyrrolo[2,3-b]pyridine-1-carboxylic acid ethyl ester in 250 ml methanol and this mixture was hydrogenated at 2 bar for 20 hours. After filtering through Celite and removing the solvent under reduced pressure, 7.27 g (85% of yield) of the expected product were obtained.

D. Preparation of 3-piperidinyl-1H-pyrrolo[2,3-b]pyridine 14.67 g (42.0 mmol) of 3-(1-ethoxycarbonyl-piperidin-4-yl)-pyrrolo[2,3-b]pyridine-1-carboxylic acid ethyl ester were added to a solution of 40.32 g (720 mmol) of potassium hydroxide in 630 ml of isopropanol. The mixture was refluxed for 20 hours. The solvent was distilled off and cold water was added. This solution was acidified with concentrated hydrochloric acid and then basified with 8 N aqueous sodium hydroxide solution. This aqueous solution was extracted twice with ethyl acetate. The organic phase was washed with water and brine, dried over magnesium sulphate, filtered and evaporated under reduced pressure affording 4.66 g (48% of yield) of the expected product as an oil.

E. Preparation of 4-(1H-pyrrolo[2,3-b]pyridin-3-yl)piperidine-1-carboxylic acid ethyl ester 4.66 g (20.0 mmol) of 3-piperidin-4-yl-1H-pyrrolo[2,3-b] pyridine were solved in 34 ml of dichloromethane and 3.1 ml (22.0 mmol) of triethylamine were added to the solution. After cooling to 0° C., 2.2 ml (22.0 mmol) of ethyl chloroformate were added dropwise. The mixture was stirred at 0° C. for 6 hours and then washed with water and brine. The organic layer was separated and dried with magnesium sulphate. After removing the solvent under reduced pressure, 5.33 g of an oil were obtained, which was purified by flash chromatography over silica gel. 3.23 g (59% of yield) of 4-(1H-pyrrolo[2,3-b]pyridin-3-yl)-piperidine-1 carboxylic acid ethyl ester were isolated.

F. Preparation of 4-[1-(2-methoxyethyl)-1H-pyrrolo[2,3-b]pyridin-3-yl]-piperidine-1-carboxylic acid ethyl ester 1.0 g (3.66 mmol) of 4-(1H-pyrrolo[2,3-b]pyridin-3-yl) piperidine-1-carboxylic acid ethyl ester were dissolved in 10 ml of DMF and, at room temperature, 0.19 g (4.76 mmol) of 60% sodium hydride were carefully added. This mixture was stirred for half an hour. 0.45 ml (5.12 mmol) of 1-bromo-2-methoxyethane were added dropwise and the mixture was further stirred for 24 hours at 60° C. The reaction mixture was cooled to room temperature and poured over cold water. The aqueous phase was extracted twice with dichloromethane and the organic phase was washed with water and brine, dried with magnesium sulphate, filtered and evaporated to dryness. This resulted in 0.86 g (71% of yield) of product.

NMR (300 MHz, CDCl3) δ=1.18-1.38 (t, 3H), 1.58-1.72 (m, 2H), 1.95-2.10 (m, 2H), 2.80-3.10 (m, 3H), 3.30 (s, 3H), 3.62-3.80 (t, 2H), 4.10-4.38 (m, 4H), 4.39-4.42 (t, 2H), 6.90-7.15 (m, 2H), 7.85-7.95 (d, 1H), 8.25-8.35 (m, 1H).

G. Preparation of 1-(2-methoxyethyl)-3-piperidinyl-1H-pyrrolo[2,3-b]pyridine 0.86 g (2.59 mmol) of 4-[1-(2-methoxyethyl)-1H-pyrrolo [2,3-b]pyridin-3-yl]-piperidine-1-carboxylic acid ethyl ester were added to a solution of 1.71 g (25.9 mmol) of potassium hydroxide in 25 ml of isopropanol. The mixture was refluxed for 20 hours. The solvent was distilled off and cold water was added. This solution was acidified with concentrated hydrochloric acid and then basified with 8 N aqueous sodium hydroxide solution. This aqueous solution was extracted twice with ethyl acetate. The organic phase was washed with water and brine, dried over magnesium sulphate, filtered and evaporated under reduced pressure. 0.42 g (68% of yield) of the expected product were obtained as an oil.

H. Preparation of 3-{4-[1-(2-methoxyethyl)-1H-pyrrolo[2,3-b]pyridin-3-yl]-piperidin-1-ylmethyl}-benzoic acid methyl ester 0.42 g (1.62 mmol) of 1-(2-methoxyethyl)-3-piperidin-4-yl-1H-pyrrolo[2,3-b]pyridine and 0.45 g (1.94 mmol) of 3-bromomethylbenzoic acid methyl ester were solved in 9 ml of 4-methyl-2-butanone and 0.67 g (4.86 mmol) of potassium carbonate and 0.02 g (0.16 mmol) of sodium iodide were added. The mixture was refluxed for 18 hours and, after cooling, water was added, the organic layer separated and washed with water and brine. The solvent was distilled off. The crude material weighed 0.67 g and was used in the following step without further purification.

I. Preparation of 3-{4-[1-(2-methoxyethyl)-1H-pyrrolo[2,3-b]pyridin-3-yl]piperidin-1-ylmethyl}benzoic acid 0.66 g (1.62 mmol) of 3-{4-[1-(2-methoxyethyl)-1H-pyrrolo[2,3-b]pyridin-3-yl]-piperidin-1-ylmethyl}-benzoic acid methyl ester were dissolved in 0.8 ml of ethyl alcohol and 2.43 ml of 2 N sodium hydroxide were added. After stirring at room temperature for 20 hours, the solvent was evaporated under reduced pressure and the residue dissolved in water. The mixture was neutralised with 2 N hydrochloric acid and extracted twice with dichlormethane. The organic phase was washed with water and brine, dried with magnesium sulphate, filtrated and evaporated. The crude material weighed 0.46 g and was purified by flash chromatography over silica gel affording 0.2 g (31% of yield) of the expected product.

Melting point=154.9-156.3° C.

NMR (300 MHz, DMSO-d6) δ=1.67-1.71 (m, 2H), 1.91-1.95 (d, 2H), 2.15 (t, 2H), 2.70-2.80 (t, 1H), 3.23 (s, 3H), 3.35-3.37 (m, 2H), 3.59 (s, 3H), 3.66-3.70 (t, 2H), 4.33-4.37 (t, 2H), 7.01-7.06 (m, 1H), 7.32 (s, 1H), 7.44-7.49 (m, 1H), 7.57-7.59 (m, 1H), 7.83-7.85 (m, 1H), 7.93 (s, 1H), 7.98-8.01 (m, 1H), 8.19-8.21 (m, 1H).

EXAMPLE 2

Preparation of 3-[4-(1-furan-3-ylmethyl-1H-pyrrolo[2,3-b]pyridin-3-yl)piperidin-1-ylmethyl]benzoic acid A. Preparation of 4-(1-furan-3-ylmethyl-1H-pyrrolo[2,3-b]pyridin-3-yl)-piperidine-1-carboxylic acid ethyl ester This compound was prepared following the procedure described in example 1, part F, starting with 1.22 g (4.46 mmol) of 4-(1H-pyrrolo[2,3-b]pyridin-3-yl)piperidine-1-carboxylic acid ethyl ester and 6.3 ml (6.24 mmol) of a freshly prepared 1 M solution of 3-bromomethylfuran in ethyl ether. The crude mixture was stirred at 60° C. for 3 hours. After standard work-up, 1 g (63% of yield) of the expected product was isolated.

B. Preparation of 1-furan-3-ylmethyl-3-piperidin-4-yl-1H-pyrrolo[2,3-b]pyridine

This compound was prepared following the procedure described in example 1, part G, starting with 1 g (2.83 mmol) of 4-(1-furan-3-ylmethyl-1H-pyrrolo[2,3-b]pyridin-3-yl)piperidine-1-carboxylic acid ethyl ester. After standard work-up, 0.82 g (100% of yield) of the expected product were isolated.

NMR (300 MHz, CDCl$_3$) δ=1.50-1.68 (m, 2H), 1.82-2.10 (m, 2H), 2.65-2.99 (m, 3H), 3.05-3.25 (m, 2H), 5.27 (s, 2H), 6.30 (s, 1H), 6.95 (s, 1H), 6.96-7.15 (m, 1H), 7.30-7.42 (m, 2H), 7.95-8.00 (d, 1H), 8.20-8.40 (m, 1H).

C. Preparation of 3-[4-(1-furan-3-ylmethyl-1H-pyrrolo[2,3-b]pyridin-3-yl)piperidin-1-ylmethyl]-benzoic acid methyl ester 0.3 ml of triethylamine were added over a solution of 0.4 g (1.42 mmol) of 1-furan-3-ylmethyl-3-piperidin-4-yl-1H-pyrrolo[2,3-b]pyridine in 5 ml of dichloromethane. A solution of 0.39 g (1.71 mmol) of 3-bromomethyl-benzoic acid methyl ester in 2 ml of dichloromethane was added and the crude mixture was stirred at room temperature for 18 hours. The mixture was diluted with 25 ml of dichloromethane and it was washed with water and brine. The organic phase was dried over magnesium sulphate and after filtration and evaporation, 0.53 g of the crude residue were obtained. The crude mixture was purified by flash chromatography over silica gel affording 0.3 g (49% of yield) of the expected product.

NMR (300 MHz, CDCl$_3$) δ=1.70-1.99 (m, 4H), 2.05-2.25 (m, 2H), 2.60-2.90 (m, 1H), 2.92-3.10 (m, 2H), 3.60 (s, 2H), 3.98 (s, 3H), 5.22 (s, 2H), 6.25 (s, 1H), 6.90-7.12 (m, 2H), 7.30-7.42 (m, 3H), 7.70-7.81 (d, 1H), 7.80-8.15 (m, 3H), 8.22-8.28 (d, 1H).

D. Preparation of 3-[4-(1-furan-3-ylmethyl-1H-pyrrolo[2,3-b]pyridin-3-yl)piperidin-1-ylmethyl]benzoic acid This compound was prepared following the procedure described in example 1, part I, starting with 0.22 g (0.51 mmol) of 3-[(1-furan-3-ylmethyl-1H-pyrrolo[2,3-b]pyridin-3-yl)-piperidin-1-ylmethyl]-benzoic acid methyl ester. After standard work-up, 0.17 g (81% of yield) of the expected product were obtained.

Melting point=177.0-178.8° C.

NMR (300 MHz, DMSO-d6) δ=1.61-1.73 (m, 2H), 1.89-1.92 (m, 2H), 2.13 (t, 2H), 2.72-2.79 (t, 1H), 2.87-2.91 (d, 2H), 3.33-3.35 (m, 2H), 3.57 (s, 3H), 5.22 (s, 2H), 6.42 (s, 1H), 7.02-7.06 (m, 1H), 7.34 (s, 1H), 7.41-7.47 (m, 1H), 7.55-7.57 (m, 2H), 7.63 (s, 1H), 7.81-7.84 (d, 1H), 7.91 (s, 1H), 7.98-8.00 (d, 1H), 8.21-8.23 (m, 1H).

EXAMPLE 3

Preparation of 2-{2-[4-(1-furan-3-ylmethyl-1H-pyrrolo[2,3-b]pyridin-3-yl)piperidine-1-yl]ethoxy}benzoic acid A. Preparation of 2-{2-[4-(1-furan-3-ylmethyl-1H-pyrrolo[2,3-b]pyridin-3-yl)-piperidin-1-yl]-ethoxy}-benzoic acid methyl ester This compound was prepared following the procedure described in example 1, part H, starting with 0.28 g (1 mmol) of 1-furan-3-ylmethyl-3-piperidin-4-yl-1H-pyrrolo[2,3-b]pyridine and 0.26 g (1.2 mmol) of 2-(2-chloroethoxy)-benzoic acid methyl ester. After standard work-up and purification, 0.16 g (35% of yield) of the expected product were obtained.

B. Preparation of 2-{2-[4-(1-furan-3-ylmethyl-1H-pyrrolo[2,3-b]pyridin-3-yl)piperidine-1-yl]ethoxy}benzoic acid This compound was prepared following the procedure described in example 1, part I, starting with 0.16 g (0.35 mmol) of 2-{2-[4 (1-furan-3-ylmethyl-1H-pyrrolo[2,3-b]pyridin-3-yl)piperidin-1-yl]-ethoxy}-benzoic acid methyl ester. After standard work-up, 0.12 g (77% of yield) of the expected product were obtained.

Melting point=105.2-106.8° C.

NMR (300 MHz, DMSO-d6) δ=1.97 (m, 4H), 2.62 (m, 2H), 2.91 (m, 1H), 2.97 (m, 2H), 3.20-3.24 (d, 2H), 4.44 (m, 3H), 5.26 (s, 2H), 6.45 (s, 1H), 6.99-7.10 (m, 2H), 7.22-7.25 (d, 1H), 7.36 (s, 1H), 7.39-7.42 (m, 1H), 7.53-7.56 (d, 1H), 7.58 (s, 1H), 7.67 (s, 1H) 8.16-8.18 (d, 1H), 8.26-8.27 (m, 1H).

EXAMPLE 4

Preparation of 3-{4-[1-(2-ethoxyethyl)-1H-pyrrolo[2,3-b]pyridin-3-yl]piperidin-1-ylmethyl}benzoic acid A. Preparation of 4-(1H-pyrrolo[2,3-b]pyridin-3-yl)-3,6-dihydro-2H-pyridine-1-carboxylic acid ethyl ester 4.37 g (21.93 mmol) of 3-(1,2,3,6-tetrahydro-pyridinyl)-1H-pyrrolo[2,3-b]pyridine were solved in 40 ml of dichloromethane and 3.34 ml (24.12 mmol) of triethylamine were added to the solution. After cooling at 0° C., 2.3 ml (24.12 mmol) of ethyl chloroformate were added dropwise. The mixture was stirred at 0° C. for 6 hours and then washed with water and brine. The organic layer was separated and dried with magnesium sulphate. After removing the solvent under reduced pressure, 5.5 g of an oil were obtained which was purified by flash chromatography over silica gel. 1.96 g (33% of yield) of 4-(1H-pyrrolo[2,3-b]pyridin-3-yl)-3,6-dihydro-2H-pyridine-1-carboxylic acid ethyl ester were isolated.

B. Preparation of 4-[1-(2-ethoxyethyl)-1H-pyrrolo[2,3-b]pyridin-3-yl]-3,6-dihydro-2H-pyridine-1-carboxylic acid ethyl ester 1.30 g (4.76 mmol) of 4-(1H-pyrrolo[2,3-b]pyridin-3-yl)-3,6-dihydro-2H-pyridine-1-carboxylic acid ethyl ester were dissolved in 11 ml of DMF and, at room temperature, 0.25 g (5.6 mmol) of 60% sodium hydride were carefully added. This mixture was stirred for half an hour at room temperature. 0.75 ml (6.0 mmol) of 2-bromoethyl ethyl ether were dropwise added and the stirring was continued for 24 hours at 60° C. The reaction mixture was cooled to room temperature and poured over cold water. This aqueous phase was extracted twice with dichloromethane and the organic phase was washed with water and brine, dried with magnesium sulphate, filtered and evaporated to dryness. The 1.46 g (74% of yield) of crude material were pure enough for the next synthetic step.

C. Preparation of 4-[1-(2-ethoxyethyl)-1H-pyrrolo[2,3-b]pyridin-3-yl]-piperidine-1-carboxylic acid ethyl ester 0.19 g of palladium, 10% (dry basis) on activated carbon (50% in water) were added to a solution of 1.46 g (4.25 mmol) of 4-[1-(2-ethoxyethyl)-1H-pyrrolo[2,3-b]pyridin-3-yl]-3,6-dihydro-2H-pyridine-1-carboxylic acid ethyl ester in 40 ml methanol and this mixture was hydrogenated at 2 bar for 6 hours. After filtering through celite and removing the solvent under reduced pressure, 0.81 g (55% of yield) of 4-[1-(2-ethoxyethyl)-1H-pyrrolo[2,3-b]pyridin-3-yl]-piperidine-1-carboxylic acid ethyl ester were obtained. NMR (300 MHz, CDCl$_3$) δ=1.05-1.38 (m, 6H), 1.55-2.12 (m, 5H), 2.90-3.05 (m, 2H), 3.20-3.50 (m, 4H), 3.60-3.65 (m, 2H), 4.03-4.26 (m, 2H), 4.30-4.45 (m, 2H), 6.97-7.26 (m, 2H), 7.90-8.03 (m, 1H), 8.22-8.27 (m, 1H).

D. Preparation of 1-(2-ethoxyethyl)-3-piperidinyl-1H-pyrrolo[2,3-b]pyridine 1.1 g (3.18 mmol) of 4-[1-(2-ethoxyethyl)-1H-pyrrolo[2,3-b]pyridin-3-yl]-piperidine-1-carboxylic acid ethyl ester were added to a solution of 2.1 g (31.8 mmol) of potassium hydroxide in 30 ml of isopropanol. The mixture was refluxed for 20 hours. The solvent was distilled off and cold water was added. This solution was acidified with concentrated hydrochloric acid and then basified with 8 N aqueous sodium hydroxide solution. This aqueous solution was extracted twice with ethyl acetate. The organic phase was washed with water and brine, dried over magnesium sulphate, filtered and evaporated under reduced pressure affording 0.65 g (75% of yield) of 1-(2-ethoxyethyl)-3-piperidinyl-1H-pyrrolo[2,3-b]pyridine obtained as an oil.

E. Preparation of 3-{4-[1-(2-ethoxyethyl)-1H-pyrrolo[2,3-b]pyridin-3-yl]-piperidin-1-ylmethyl}-benzoic acid methyl ester 0.98 g (3.58 mmol) of 1-(2-ethoxyethyl)-3-piperidinyl-1H-pyrrolo[2,3-b]pyridine and 0.92 g (4.29 mmol) of methyl 2-(2-chloroethoxy)benzoate were dissolved in 21 ml of 4-methyl-2-butanone and 1.48 g (10.74 mmol) of potassium carbonate and 0.07 g (0.4 mmol) of sodium iodide were added. The mixture was refluxed for 18 hours and, after cooling, water was added, the organic layer separated, washed with water and brine. The solvent was distilled off. The crude material weighed 2.1 g and was purified by flash chromatography over silica gel affording 0.58 g (36% of yield) of the expected product.

F. Preparation of 3{-([1-(2-ethoxyethyl)-1H-pyrrolo[2,3-b]pyridin-3-yl]piperidin-1-ylmethyl}benzoic acid 0.58 g (1.28 mmol) of 3-{4-[1-(2-ethoxyethyl)-1H-pyrrolo[2,3-b]pyridin-3-yl]-piperidin-1-ylmethyl}-benzoic acid methyl ester were dissolved in 5 ml of ethyl alcohol and 1.93 ml of 2 N sodium hydroxide were added. After stirring at room temperature for 20 hours, the solvent was evaporated under reduced pressure and the residue dissolved in water. The mixture was neutralised with 2 N hydrochloric acid and extracted twice with dichloromethane. The organic phase was washed with water and brine, dried with magnesium sulphate, filtrated and evaporated. The crude material weighed 0.65 g and was purified by flash chromatography over silica gel affording 0.3 g (54% of yield) of the expected product.

Melting point=173.2-175.0° C.

NMR (300 MHz, DMSO-d6) δ=1.05-1.09 (t, 3H), 2.07-2.22 (m, 4H), 3.02-3.12 (m, 3H), 3.40-3.46 (q, 2H), 3.51-3.55 (m, 1H), 3.73-3.76 (m, 2H), 4.27 (s, 2H), 4.37-4.39 (m, 2H), 7.05-7.09 (m, 1H), 7.30 (s, 1H), 7.48-7.53 (t, 1H), 7.63-7.65 (d, 1H), 8.04-8.10 (m, 2H), 8.19-8.21 (m, 2H).

EXAMPLE 5

Preparation of 5-{4-[1-(2-ethoxyethyl)-1H-pyrrolo[2,3-b]pyridin-1-ylmethyl}-2-methoxybenzoic acid A. Preparation of 5-{4-[1-(2-ethoxyethyl)-1H-pyrrolo[2,3-b]pyridin-3-yl]-piperidin-1-ylmethyl}-2-methoxy-benzoic acid ethyl ester This compound was prepared following the procedure described in example 4, part E, starting with 0.73 g (2.67 mmol) of 1-(2-ethoxyethyl)-3-piperidin-4-yl-1H-pyrrolo[2,3-b]pyridine and 0.88 g (3.20 mmol) of 5-bromomethyl-2-methoxybenzoic acid ethyl ester. After standard work-up and purification, 0.38 g (31% of yield) of the expected product were obtained.

NMR (300 MHz, CDCl$_3$) δ=0.99-1.14 (t, 3H), 1.21-1.28 (t, 3H), 1.60-2.15 (m, 4H), 2.58-2.79 (m, 1H), 2.80-2.99 (m, 2H), 3.22-3.45 (m, 4H), 3.55-3.62 (m, 2H), 3.78 (s, 3H), 4.20-4.38 (m, 4H), 5.18 (s, 2H), 6.78-7.00 (m, 3H), 7.35-7.41 (m, 1H), 7.62 (s, 1H), 7.78-7.82 (m, 1H), 8.18-8.20 (m, 1H).

B. 5-{4-[1-(2-ethoxyethyl)-1H-pyrrolo[2,3-b]pyridin-1-ylmethyl}-2-methoxybenzoic acid This compound was prepared following the procedure described in example 4, part F, starting with 0.38 g (0.52 mmol) of 5-{4-[1-(2-ethoxyethyl)-1H-pyrrolo[2,3-b]pyridin-3-yl]-piperidin-1-ylmethyl}-2-methoxy-benzoic acid ethyl ester. After standard work-up, 0.22 g (62% of yield) of the expected product were obtained.

Melting point=207.9-209.2° C.

NMR (300 MHz, DMSO-d6) δ=1.02-1.07 (t, 3H), 1.17-1.23 (m, 2H), 1.73-1.77 (m, 2H), 1.96-1.99 (m, 2H), 2.20-2.40 (m, 1H), 2.83 (m, 1H), 3.02 (m, 2H), 3.37-3.44 (m, 4H), 3.68-3.72 (t, 2H), 3.82 (s, 3H), 4.34-4.36 (m, 2H), 7.02-7.06 (m, 1H), 7.13-7.15 (d, 1H), 7.33 (s, 1H), 7.50-7.52 (d, 1H), 7.66 (s, 1H), 7.99-8.03 (d, 1H), 8.20-8.21 (m, 1H).

EXAMPLE 6

Preparation of 2-(2-{4-[1-(2-ethoxyethyl)-1H-pyrrolo[2,3-b]pyridin-3-yl]-piperidin-1-ylethoxy)benzoic acid A. Preparation of 2-(2-{4-[1-(2-ethoxyethyl)-1H-pyrrolo[2,3-b]pyridin-3-yl]-piperidin-1-yl}-ethoxy)-benzoic acid methyl ester This compound was prepared following the procedure described in example 4, part E, starting with 0.98 g (3.58 mmol) of 1-(2-ethoxyethyl)-3-piperidin-4-yl-1H-pyrrolo[2,3-b]pyridine and 0.92 g (4.29 mmol) of 2-(2-chloroethoxy)benzoic acid methyl ester. After standard work-up and purification, 0.58 g (36% of yield) of the expected product were obtained.

B. 2-(2-{4-[1-(2-ethoxyethyl)-1H-pyrrolo[2,3-b]pyridin-3-yl]piperidin-1-ylethoxy)benzoic acid This compound was prepared following the procedure described in example 4, part F, starting with 0.58 g (1.28 mmol) of 2-(2-{4-[1-(2-ethoxyethyl)-1H-pyrrolo[2,3-b]pyridin-3-yl]-piperidin-1-yl}-ethoxy)-benzoic acid methyl ester. After standard work-up, 0.3 g (54% of yield) of the expected product were obtained.

Melting point=136.6-140.3° C.

NMR (300 MHz, DMSO-d6) δ=1.03-1.08 (t, 3H), 1.97-2.45 (m, 4H), 2.59-2.68 (m, 2H), 2.89-2.99 (m, 3H), 3.21-3.24 (d, 2H), 3.37-3.46 (q, 2H), 3.70-3.73 (t, 2H), 4.34-4.38 (t, 2H), 4.42-4.46 (m, 2H), 5.20-6.20 (m, 1H), 6.99-7.08 (m, 2H), 7.22-7.25 (d, 1H), 7.34 (s, 1H), 7.37-7.42 (m, 1H), 7.53-7.56 (d, 1H), 8.14-8.17 (d, 1H), 8.23-8.24 (d, 1H).

Alternatively, the novel azaindolylpiperidine derivatives of the present invention can be prepared according to a different strategy as shown in Scheme 3.

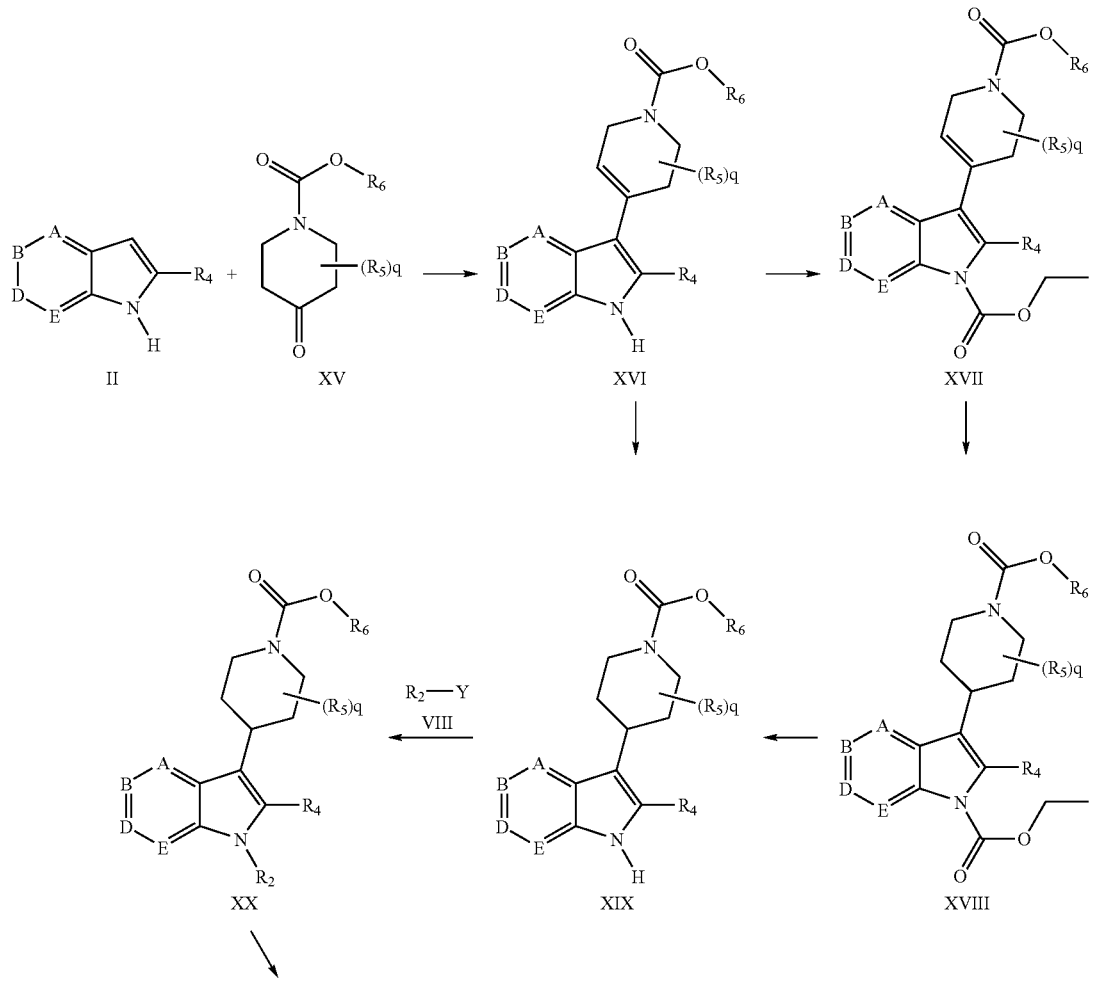

Scheme 3

-continued

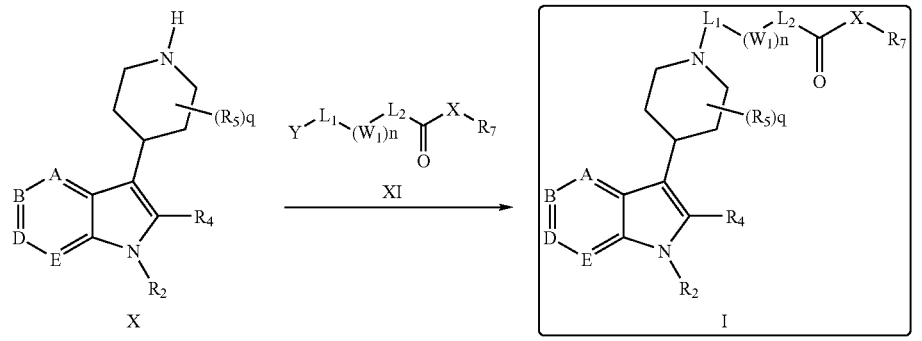

A condensation between a compound of general formula II wherein A, B, D, E and R₄ are as defined above and a compound of general formula XV wherein R₅ and q are as defined above and R₈ is an ethyl or tert-butyl group gives a compound of general formula XVI. This reaction is preferably carried out in the presence of a base such as sodium or potassium hydroxide in an alcoholic solvent such as methanol, ethanol or isopropanol at a temperature between 60° and 150° C.

The compound of general formula XVI, wherein A, B, D, E, R₄, R₅ and q are as defined above and R₈ is a tert-butyl group, is treated with ethyl chloroformate in the presence of a base such as triethylamine at a temperature between 0° C. and 80° C. to give a compound of general formula XVII wherein A, B, D, E, R₄, R₅ and q are as defined above and R₈ is a tert-butyl group.

Compound XVII is either hydrogenated using palladium or platinum oxide as catalyst in a solvent such as methanol or ethanol in acidic or neutral conditions at a pressure between 2 or 3 bar or reduced with an hydride such as sodium borohydride to give a compound of general formula XVIII wherein A, B, D, E, R₄, R₅ and q are as defined above and R₈ is a tert-butyl group.

The ethyl carbamate moiety on the indolyl group is deprotected by boiling compound XVIII in the presence of an excess of sodium or potassium hydroxide in an alcoholic solvent such as ethanol or isopropanol at a temperature between 80° C. and 180° C., giving a compound of general formula XIX wherein A, B, D, E, R₄, R₅ and q are as defined above and R₈ is a tert-butyl group.

Alternatively, the compound of general formula XVI wherein A, B, D, E, R₄, R₅ and q are as defined above and R₈ is an ethyl group is either hydrogenated using palladium or platinum oxide as catalyst in a solvent such as methanol or ethanol in acidic or neutral conditions at a pressure between 2 or 3 bar or reduced using an hydride such as sodium borohydride, to give a compound of general formula XIX wherein A, B, D, E, R₄, R₅ and q are as defined before and R₈ is an ethyl group.

The compound of general formula XIX wherein R₈ is either an ethyl or a tert-butyl group is alkylated with a reactive intermediate of general formula VIII, which is as previously defined in Scheme 1, to give a compound of general formula XX wherein A, B, D, E, R₂, R₄, R₅ and q are as defined above, and R₈ is an ethyl or a tert-butyl group. This reaction is preferably carried out in an inert solvent such as tetrahydrofuran, dimethylformamide or ethyl ether in the presence of an inorganic base such as sodium hydride or sodium amide at a temperature between 0° C. and 80° C.

The compound of general formula XX is deprotected to give a compound of formula X, which is as previously defined in Scheme 1. When the substituent R₈ of compound XX is a tert-butyl group this is done by treatment with trifluoroacetic acid in dichloromethane at a temperature between 0° C. and room temperature. When the substituent R₈ of compound XX is an ethyl group it is deprotected by treatment with sodium or potassium hydroxide in a solvent such as ethanol, isopropanol or n-butanol at a temperature between 80° C. and 180° C.

As in Scheme 1, the alkylation of compound X with a reactive intermediate of general formula XI gives a compound of general formula I. This reaction is preferably carried out in an organic solvent such as toluene, dichloromethane, dioxane or methyl isobutylketone at a temperature between 25° C. and 140° C. and in the presence of a base such as an alkali metal carbonate or bicarbonate, triethylamine or diisopropylethylamine.

Compounds of general formula I wherein R₇ is an oxygen atom are treated with sodium or potassium hydroxide in a solvent such as methanol, ethanol or tetrahydrofuran at a temperature between 25° C. and 60° C. Further treatment with an inorganic acid such as hydrochloric acid provides the corresponding azaindolylpiperidine derivatives of general formula XIV wherein A, B, D, E, L₁, L₂, R₂, R₄, R₅, q, W₁, n and X are as defined above (see Scheme 2).

The following Examples represent typical synthetic procedures according to Scheme 3. These Examples are given by way of illustration only and are not intended to limit the scope of the present invention in any way.

TABLE 2

List of examples according to Scheme 3

| Example | R1 | R2 | Mol. weight |
|---|---|---|---|
| 7 | 5-(methylene)-2-methoxybenzoic acid | furan-3-ylmethyl | 445.516 |
| 8 | 2-(2-oxyethyl)benzoic acid | furan-2-ylmethyl | 445,516 |
| 9 | 3-(methylene)benzoic acid | furan-2-ylmethyl | 415,516 |
| 10 | 5-(methylene)-2-methoxybenzoic acid | furan-2-ylmethyl | 445,516 |
| 11 | 2-(2-oxyethyl)benzoic acid | furan-2-ylmethyl | 461.583 |
| 12 | 3-(methylene)benzoic acid | thien-2-ylmethyl | 431.558 |
| 13 | 5-(methylene)-2-methoxybenzoic acid | thien-2-ylmethyl | 461.583 |

TABLE 2-continued

List of examples according to Scheme 3

| Example | R1 | R2 | Mol. weight |
|---------|----|----|-------------|
| 14 | 2-(propoxy)benzoic acid | thiophen-3-ylmethyl | 461.583 |
| 15 | 3-methylbenzoic acid | thiophen-3-ylmethyl | 431.558 |
| 16 | 5-methyl-2-methoxybenzoic acid | thiophen-3-ylmethyl | 461.583 |
| 17 | 2-(propoxy)benzoic acid | (5-chlorothiophen-2-yl)methyl | 496.003 |
| 18 | 3-methylbenzoic acid | (5-chlorothiophen-2-yl)methyl | 466.003 |
| 19 | 5-methyl-2-methoxybenzoic acid | (5-chlorothiophen-2-yl)methyl | 496.003 |
| 20 | 2-(propoxy)benzoic acid | 2-methoxyethyl | 423.510 |

TABLE 2-continued
List of examples according to Scheme 3
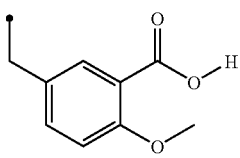
| Example | R1 | R2 | Mol. weight |
|---|---|---|---|
| 21 | 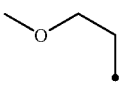 | 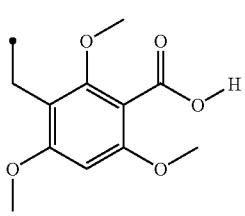 | 423.510 |
| 22 | 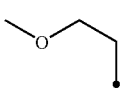 | 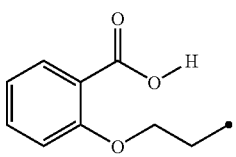 | 453.536 |
| 23 | 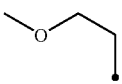 | 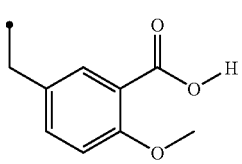 | 453.536 |
| 24 | 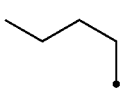 | 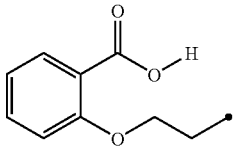 | 421.538 |
| 25 | 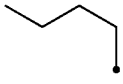 | 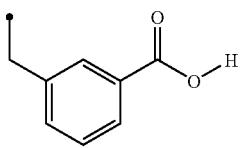 | 421.538 |
| 28 | 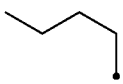 | 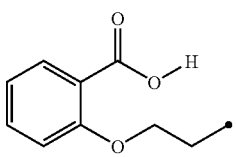 | 391.512 |
| 27 | 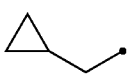 | | 419.522 |

TABLE 2-continued

List of examples according to Scheme 3

| Example | R1 | R2 | Mol. weight |
|---|---|---|---|
| 28 | 3-(carboxy)benzyl | cyclopropylmethyl | 389.496 |
| 29 | 3-(carboxy)-4-methoxybenzyl | cyclopropylmethyl | 419.522 |
| 30 | 2-(2-carboxyphenoxy)ethyl | isopropyl | 407.511 |
| 31 | 3-(carboxy)benzyl | isopropyl | 377.485 |
| 32 | 3-(carboxy)-4-methoxybenzyl | isopropyl | 407.511 |
| 33 | 2-(2-carboxyphenoxy)ethyl | 4-fluorobenzyl | 473.545 |
| 34 | 4-carboxybutyl | 4-fluorobenzyl | 395.475 |
| 35 | 2-(carboxymethoxy)ethyl | 4-fluorobenzyl | 411.474 |

TABLE 2-continued

List of examples according to Scheme 3

| Example | R1 | R2 | Mol. weight |
|---|---|---|---|
| 36 | 4-methoxy-2-(propyloxy)benzoic acid (2-methoxy-4-carboxyphenoxy)propyl | 2-ethoxyethyl | 467.563 |
| 37 | 3-methoxy-2-(propyloxy)benzoic acid group | 2-ethoxyethyl | 467.563 |
| 38 | 4-chloro-2-(propyloxy)benzoic acid group | 2-ethoxyethyl | 471.982 |
| 39 | (2-fluoro-3-carboxyphenyl)methyl | 2-ethoxyethyl | 425.501 |
| 40 | (2-methoxy-3-carboxyphenyl)methyl | 2-ethoxyethyl | 437.537 |
| 41 | (2,4-dimethoxy-3-... carboxyphenyl)methyl | 2-ethoxyethyl | 467.563 |

TABLE 2-continued

List of examples according to Scheme 3

| Example | R1 | R2 | Mol. weight |
|---|---|---|---|
| 42 | 2-methoxy-6-(propoxy) benzoic acid | 2-ethoxyethyl | 467.563 |
| 43 | 4-methoxy-2-(propoxy) benzoic acid | furan-3-ylmethyl | 475.542 |
| 44 | 4-chloro-2-(propoxy) benzoic acid | furan-3-ylmethyl | 479.961 |
| 45 | 2-fluoro-5-methyl benzoic acid | furan-3-ylmethyl | 433.481 |
| 46 | 3-methoxy-2-(propoxy) benzoic acid | furan-3-ylmethyl | 475.542 |
| 47 | 2-methoxy-3-methyl benzoic acid | furan-3-ylmethyl | 445.516 |
| 48 | 2-methoxy-3-methyl-4-methoxy benzoic acid | furan-3-ylmethyl | 475.542 |

TABLE 2-continued

List of examples according to Scheme 3

| Example | R1 | R2 | Mol. weight |
|---|---|---|---|
| 49 | 2-methoxy-6-(propoxy)benzoic acid linker | furan-3-ylmethyl | 475.542 |
| 50 | 4-methoxy-2-(propoxy)benzoic acid linker | furan-2-ylmethyl | 475.542 |
| 51 | 3-methoxy-2-(propoxy)benzoic acid linker | furan-2-ylmethyl | 475.542 |
| 52 | 4-chloro-2-(propoxy)benzoic acid linker | furan-2-ylmethyl | 479.961 |
| 53 | 2-fluoro-5-methylbenzoic acid linker | furan-2-ylmethyl | 433.481 |
| 54 | 3-methoxy-2-(propoxy)benzoic acid linker | 5-chlorothiophen-2-ylmethyl | 526.054 |

TABLE 2-continued

List of examples according to Scheme 3

| Example | R1 | R2 | Mol. weight |
|---------|----|----|-------------|
| 55 | 4-methoxy-2-(propoxy)benzoic acid | 5-chlorothiophen-2-ylmethyl | 526.054 |
| 56 | 4-chloro-2-(propoxy)benzoic acid | 5-chlorothiophen-2-ylmethyl | 530.474 |
| 57 | 2-fluoro-5-methylbenzoic acid | 5-chlorothiophen-2-ylmethyl | 483.993 |
| 58 | 2-methoxy-3-methylbenzoic acid | 5-chlorothiophen-2-ylmethyl | 496.028 |
| 59 | 2,4-dimethoxy-3-methylbenzoic acid | 5-chlorothiophen-2-ylmethyl | 526.054 |
| 60 | 2-methoxy-6-(propoxy)benzoic acid | 5-chlorothiophen-2-ylmethyl | 526.054 |
| 61 | 4-methoxy-2-(propoxy)benzoic acid | pentyl | 451.564 |

TABLE 2-continued
List of examples according to Scheme 3
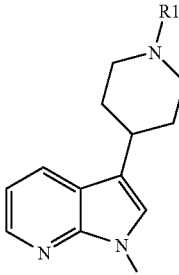
| Example | R1 | R2 | Mol. weight |
|---|---|---|---|
| 62 |  | 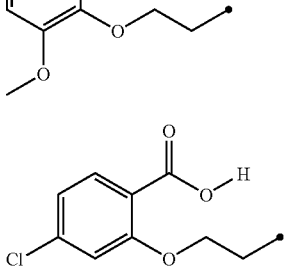 | 451.564 |
| 63 | 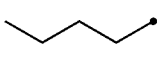 | 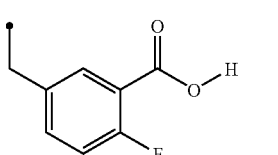 | 455.983 |
| 64 | 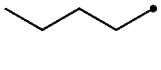 | 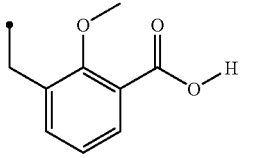 | 409.502 |
| 65 |  | 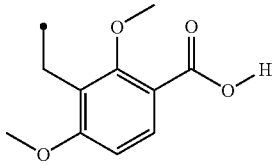 | 421.538 |
| 66 | 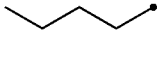 | 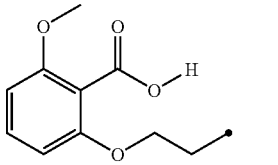 | 451.564 |
| 67 |  | 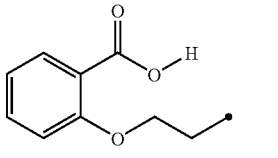 | 451.564 |
| 68 | 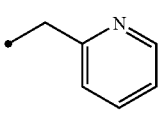 | | 456.543 |

TABLE 2-continued

List of examples according to Scheme 3

| Example | R1 | R2 | Mol. weight |
|---|---|---|---|
| 69 | butanoic acid (·-CH₂CH₂CH₂-COOH) | 2-pyridylmethyl | 378.473 |
| 70 | 2-(carboxyphenoxy)propyl | 2-ethoxyethyl | 437.537 |
| 71 | 2-(carboxy-3-methoxyphenoxy)propyl | 2-ethoxyethyl | 467.563 |
| 72 | 2-(carboxy-4-methoxyphenoxy)propyl | 2-ethoxyethyl | 467.563 |
| 73 | 2-(carboxy-4-chlorophenoxy)propyl | 2-ethoxyethyl | 471.982 |
| 74 | 3-(carboxy-4-methoxyphenyl)methyl | 2-ethoxyethyl | 437.537 |
| 75 | 3-(carboxy-4-bromophenyl)methyl | 2-ethoxyethyl | 486.407 |

TABLE 2-continued

List of examples according to Scheme 3

| Example | R1 | R2 | Mol. weight |
|---|---|---|---|
| 76 | 4-methoxy-2-(propyloxy)benzoic acid | furan-3-ylmethyl | 475.542 |
| 77 | 2-(propyloxy)benzoic acid | furan-3-ylmethyl | 445.516 |
| 78 | 3-(methyl)benzoic acid | furan-3-ylmethyl | 445.516 |
| 79 | 3-(methyl)benzoic acid | furan-3-ylmethyl | 445.516 |
| 80 | 4-chloro-2-(propyloxy)benzoic acid | furan-3-ylmethyl | 479.961 |
| 81 | 2-(propyloxy)benzoic acid | pentyl | 421.538 |
| 82 | 3-methoxy-2-(propyloxy)benzoic acid | pentyl | 451.564 |

TABLE 2-continued
List of examples according to Scheme 3
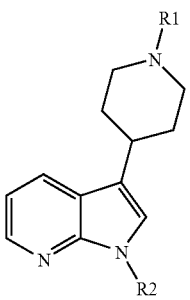
| Example | R1 | R2 | Mol. weight |
|---|---|---|---|
| 83 | 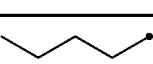 | 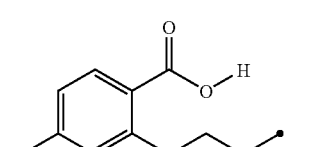 | 451.564 |
| 84 | 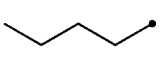 | 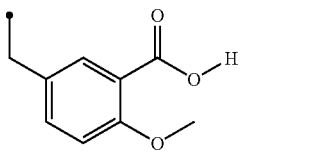 | 455.983 |
| 85 | 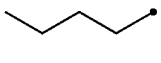 | 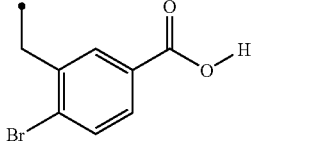 | 421.538 |
| 86 | 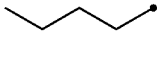 | 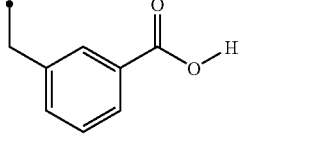 | 470.408 |
| 87 | 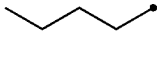 | 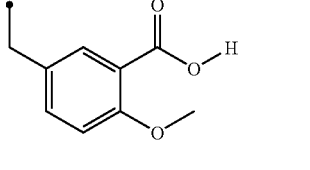 | 391.512 |
| 88 | 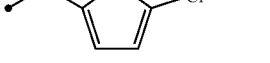 | 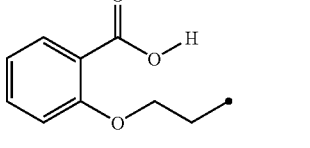 | 496.028 |
| 89 | 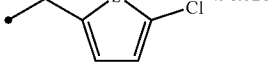 | 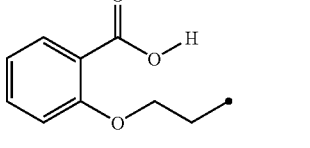 | 496.028 |

TABLE 2-continued

List of examples according to Scheme 3

| Example | R1 | R2 | Mol. weight |
|---|---|---|---|
| 90 | 3-methoxy-2-(propoxy)benzoic acid | 5-chlorothiophen-2-ylmethyl | 526.054 |
| 91 | 4-methoxy-2-(propoxy)benzoic acid | 5-chlorothiophen-2-ylmethyl | 526.054 |
| 92 | 4-chloro-2-(propoxy)benzoic acid | 5-chlorothiophen-2-ylmethyl | 530.474 |
| 93 | (ethoxy)acetic acid | 5-chlorothiophen-2-ylmethyl | 433.958 |
| 94 | 2-(propoxy)benzoic acid | tetrahydrothiophen-2-ylmethyl | 461.583 |
| 95 | 2-(propoxy)benzoic acid | furan-2-ylmethyl | 445.516 |
| 96 | 5-methyl-2-methoxybenzoic acid | furan-2-ylmethyl | 445.516 |

TABLE 2-continued

List of examples according to Scheme 3

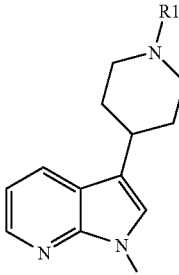

| Example | R1 | R2 | Mol. weight |
|---|---|---|---|
| 97 |  | 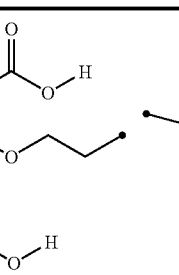 | 491.609 |
| 98 |  | 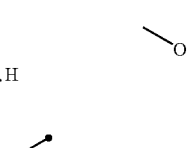 | 461.583 |
| 99 | 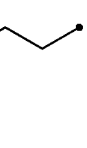 | (structure) | 423.510 |

The sign (*) in the structures shows the point of attachment. It does not symbolise a carbon atom.

EXAMPLE 7

Preparation of 5-[4-(1-furan-3-ylmethyl-1H-pyrrolo [2,3-b]pyridin-3-yl)-piperidin-1-ylmethyl]-2-methoxy-benzoic acid A. Preparation of 4-(1H-pyrrolo[2,3-b]pyridin-3-yl)-3,6-dihydro-2H-pyridine-1-carboxylic acid tert-butyl ester 5 g (40 mmol) of 7-azaindole and 20 g (100 mmol) 4-oxopiperidine-1-carboxylic acid tert-butyl ester were added to an ice-cooled solution of 6 g (100 mmol) of potassium hydroxide in 120 ml of methanol. The mixture was heated to room temperature and then refluxed for 18 hours. Once cooled to room temperature, the formed solid was isolated by suction filtration. The filtered solution was concentrated at vacuum and a mixture of 22 ml of ethanol and 50 ml of water was added to the residue. A yellowish solid precipitated which corresponded to 6.32 g (53% of yield) of the expected product.

B. Preparation of 3-(1-tert-butoxycarbonyl-1,2,3,6-tetrahydro-pyridinyl)-pyrrolo[2,3-b]pyridine-1-carboxylic acid ethyl ester Over a solution of 6.3 g (21.07 mmol) of 4-(1H-pyrrolo[2,3-b]pyridin-3-yl)-3,6-dihydro-2H-pyridine-1-carboxylic acid tert-butyl ester and 3.2 ml (23.16 mmol) of triethylamine in 50 ml of dichloromethane at 0° C., 2.2 ml (23.16 mmol) of ethyl chloroformate were added dropwise. The crude mixture was stirred at 0° C. for 1 hour and then warmed to room temperature for 8 hours. The reaction mixture was washed with 50 ml of water and the organic phase was separated. After drying over sodium sulphate, filtering and removing the solvent at reduced pressure, 8.7 g (100% of yield) of 3-(1-tert-butoxycarbonyl-1,2,3,6-tetrahydro-pyridinyl)-pyrrolo [2,3-b]pyridine-1-carboxylic acid ethyl ester were isolated.

C. Preparation of 3-(1-tert-butoxycarbonyl-piperidin-4-yl)pyrrolo[2,3-b]pyridine-1-carboxylic acid ethyl ester 0.47 g of palladium, 10% (dry basis) on activated carbon were added to a solution of 4.67 g (12.6 mmol) of 3-(1-tert-butoxycarbonyl-1,2,3,6-tetrahydro-pyridinyl)-pyrrolo[2,3-b]pyridine-1-carboxylic acid ethyl ester in 150 ml of methanol and this mixture was submitted to hydrogenation at 30 psi for 24 hours. After filtering through celite and removing the solvent under reduced pressure, 4 g (85% of yield) of the expected product were obtained.

D. Preparation of 4-(1H-pyrrolo[2,3-b]pyridin-3-yl)-piperidine-1-carboxylic acid tert-butyl ester 4 g (10.72 mmol) of 3-(1-tert-butoxycarbonyl-piperidin-4-yl)-pyrrolo[2,3-b]pyridine-1-carboxylic acid ethyl ester were added to a solution of 3 g (53.6 mmol) of potassium hydroxide in 120 ml of isopropanol. The mixture was refluxed for 16 hours. The solvent was distilled off and cold water was added. This solution was acidified with concentrated hydrochloric acid and then basified with 8 N aqueous sodium hydroxide solution. This aqueous solution was extracted twice with ethyl acetate. The organic phase was washed with water and brine, dried over magnesium sulphate, filtered and evaporated under reduced pressure. 1.6 g (50% of yield) of the expected product were obtained as yellowish solid.

E. Preparation of 4-(1-furan-3-ylmethyl-1H-pyrrolo[2,3-b]pyridin-3-yl)piperidine-1-carboxylic acid tert-butyl ester Under nitrogen atmosphere, 1.14 g (3.76 mmol) of 4-(1H-pyrrolo[2,3-b]pyridin-3-yl)-piperidine-1-carboxylic acid tert-butyl ester were dissolved in 30 ml of anhydrous DMF and, at room temperature, carefully added to a suspension containing 0.24 g (6.05 mmol) of 60% sodium hydride. This mixture was stirred for 30 minutes and 8.2 ml (4.92 mmol) of a freshly prepared 0.6 M solution of 3-bromomethylfuran in ethyl ether were dropwise added and the reaction mixture was stirred at room temperature for 16 hours. The solvent was removed under reduced pressure and the crude mixture was extracted between ethyl acetate and water. The organic phase was washed with water and brine, dried with magnesium sulphate, filtered and evaporated to dryness. The crude mixture was purified by flash chromatography over silica gel affording 1.4 g (97% of yield) of the expected product.

F. Preparation of 1-furan-3-ylmethyl-3-piperidinyl-1H-pyrrolo[2,3-b]pyridine Over a solution of 1.4 g (3.7 mmol) of 4-(1-furan-3-ylmethyl-1H-pyrrolo[2,3-b]pyridin-3-yl) piperidine-1-carboxylic acid tert-butyl ester in 10 ml of dichloromethane, 2.85 ml of trifluoroacetic acid were carefully added. The crude mixture was stirred at room temperature for 1 hour. The solvent was removed under reduced pressure and the crude residue was dissolved in 10 ml of ethyl acetate and washed with saturated aqueous solution of sodium carbonate and brine. After drying over sodium sulphate, filtering and removing the solvent under reduced pressure, 0.62 g (60% of yield) of the expected product were obtained.

NMR (300 MHz, CDCl3) δ=1.50-1.68 (m, 2H), 1.82-2.10 (m, 2H), 2.65-2.99 (m, 3H), 3.05-3.25 (m, 2H), 5.27 (s, 2H), 6.30 (s, 1H), 6.95 (s, 1H), 6.96-7.15 (m, 1H), 7.30-7.42 (m, 2H), 7.95-8.00 (d, 1H), 8.20-8.40 (m, 1H).

G. Preparation of 5-[4-(1-furan-3-ylmethyl-1H pyrrolo[2,3-b]pyridin-3-yl)-piperidin-1-ylmethyl]-2-methoxy-benzoic acid ethyl ester This compound was prepared following the procedure described in example 4, part E, starting with 0.62 g (2.2 mmol) of 1-furan-3-ylmethyl-3-piperidinyl-1H-pyrrolo[2,3-b]pyridine and 0.79 g (2.9 mmol) of 5-bromomethyl-2-methoxybenzoic acid ethyl ester. After standard work-up and purification, 0.95 g (91% of yield) of the expected ester were obtained.

NMR (300 MHz, CDCl$_3$) δ=1.35-1.42 (t, 3H), 1.80-2.15 (m, 6H), 2.70-3.15 (m, 3H), 3.55 (s, 2H), 3.98 (s, 3H), 4.30-4.40 (q, 2H), 5.23 (s, 2H), 6.92-7.30 (m, 5H), 7.35-7.45 (m, 3H), 7.70 (s, 1H), 7.90 (d, 1H), 8.30 (d, 1H).

H. Preparation of 5-[4-(1-furan-3-ylmethyl-1H-pyrrolo[2,3-b]pyridin-3-yl)piperidin-1-ylmethyl]-2-methoxy-benzoic acid This compound was prepared following the procedure described in example 4, part F, starting with 0.95 g (2 mmol) of 5-[4-(1-furan-3-ylmethyl-1H-pyrrolo[2,3-b]pyridin-3-yl)-piperidin-1-ylmethyl]-2-methoxy-benzoic acid ethyl ester. After standard work-up, 0.7 g of the crude acid were obtained which were washed with hot water, ethanol and ethyl ether affording 0.33 g (37% of yield) of the pure acid.

Melting point=230.5-232.4° C.

NMR (300 MHz, DMSO-d6) δ=1.61-1.72 (m, 2H), 1.89-1.93 (m, 2H), 2.08-2.15 (t, 2H), 2.73-2.80 (m, 1H), 2.88-2.92 (d, 2H), 3.48 (s, 2H), 3.80 (s, 3H), 5.23 (s, 2H), 6.43 (s, 1H), 7.03-7.09 (m, 2H), 7.34 (s, 1H), 7.41-7.45 (dd, 1H), 7.56-7.58 (m, 2H), 7.64 (s, 1H), 7.99-8.01 (d, 1H), 8.23-8.24 (m, 1H).

EXAMPLES 8-9

These compounds were prepared following the procedure described in example 7, parts G and H, starting with 0.094 g (0.33 mmol) of 1-furan-2-ylmethyl-3-piperidin-4-yl-1H-pyrrolo[2,3-b]pyridine. The crude mixtures were purified by preparative HPLC triggered by MS. ESI/MS and purity data corresponding to these compounds are shown in table 3.

A. Preparation of 1-furan-2-ylmethyl-3-piperidin-4-yl-1H-pyrrolo[2,3-b]pyridine This compound was prepared following the procedure described in example 7, parts E and F, starting with 0.3 g (1 mmol) of 4-(1H-pyrrolo[2,3-b]pyridin-3-yl)-piperidine-1-carboxylic acid tert-butyl ester and 2.12 ml of a freshly prepared 0.61 M solution of 2-bromomethylfuran in ethyl ether. After standard work-up, 0.28 g (97% of yield) of the expected product were isolated.

TABLE 3

| Example | ESI/MS m/e [(M)+] | Purity (%) |
|---|---|---|
| 8 | 445 | 100 |
| 9 | 415 | 100 |

EXAMPLE 10

Preparation of 5-[4-(1-furan-2-ylmethyl-1H-pyrrolo[2,3-b]pyridin-3-yl)piperidin-1-ylmethyl]-2-methoxybenzoic acid This compound was prepared following the procedure described in example 7, part G and H starting with 2.37 g (8.4 mmol) of 1-furan-2-ylmethyl-3-piperidin-4-yl-1H-pyrrolo[2,3-b]pyridine and 3 g (11 mmol) of 5-bromomethyl-2-methoxy-benzoic acid ethyl ester. After standard purification the overall yield was 76% (1.6 g).

Melting point=230.9-231.8° C.

NMR (300 MHz, DMSO-d6) δ=1.61-1.73 (m, 2H), 1.89-1.93 (d, 2H), 2.09-2.16 (t, 2H), 2.73-2.81 (t, 1H), 2.89-2.92 (d, 2H), 3.49 (s, 2H), 3.80 (s, 3H), 5.40 (s, 2H), 6.36-6.39 (m, 2H), 7.04-7.08 (dd, 1H), 7.30 (s, 1H), 7.41-7.44 (dd, 1H), 7.56-7.58 (m, 2H), 8.00-8.03 (m, 1H), 8.23-8.25 (dd, 1H)

EXAMPLES 11-13

These compounds were prepared following the procedure described in example 7, parts G and H, starting with 0.098 g (0.33 mmol) of 3-piperidin-4-yl-1-thiophen-2-ylmethyl-1H-pyrrolo[2,3-b]pyridine. The crude mixtures were purified by preparative HPLC triggered by MS. ESI/MS data corresponding to these compounds are shown in table 4.

A. Preparation of 3-piperidinyl-1-thiophen-2-ylmethyl-1H-pyrrolo[2,3-b]pyridine This compound was prepared following the procedure described in example 7, parts E and F, starting with 0.3 g (1 mmol) of 4-(1H-pyrrolo[2,3-b]pyridin-3-yl)piperidine-1-carboxylic acid tert-butyl ester and 2.12 ml of a freshly prepared 0.61 M solution of 2-bromomethylthiophene in ethyl ether. After standard work-up, 0.29 g (100% of yield) of the expected product were isolated.

TABLE 4

| Example | ESI/MS m/e [(M)+] | Purity (%) |
|---|---|---|
| 11 | 461 | 100 |
| 12 | 431 | 51 |
| 13 | 461 | 100 |

EXAMPLES 14-16

These compounds were prepared following the procedure described in example 7, parts G and H, starting with 0.098 g (0.33 mmol) of 3-piperidinyl-1-thiophen-3-ylmethyl-1H-pyrrolo[2,3-b]pyridine. The crude mixtures were purified by preparative HPLC triggered by MS. ESI/MS and purity data corresponding to these compounds are shown in table 5.

A. Preparation of 3-piperidinyl-1-thiophen-3-ylmethyl-1H-pyrrolo[2,3-b]pyridine This compound was prepared following the procedure described in example 7, parts E and F, starting with 0.3 g (1 mmol) of 4-(1H-pyrrolo[2,3-b]pyridin-3-yl)-piperidine-1-carboxylic acid tert-butyl ester and 2.12 ml of a freshly prepared 0.61 M solution of 3-bromomethylthiophene in ethyl ether. After standard work-up, 0.39 g (100% of yield) of the expected product were isolated.

TABLE 5

| Example | ESI/MS m/e [(M)+] | Purity (%) |
|---|---|---|
| 14 | 461 | 100 |
| 15 | 431 | 100 |
| 16 | 461 | 100 |

EXAMPLE 17

Preparation of 2-(2-{4-[1-(5-chlorothiophen-2-ylmethyl)-1H-pyrrolo[2,3-b]pyridin-3-yl]piperidin-1-yl}ethoxy)benzoic acid

A. Preparation of 4-[1-(5-chlorothiophen-2-ylmethyl)-1H-pyrrolo[2,3-b]pyridin-3-yl]-piperidine-1-carboxylic acid tert-butyl ester This compound was prepared following the procedure described in example 7, part E, starting with 2 g (6.6 mmol) of 4-(1H-pyrrolo[2,3-b]pyridin-3-yl)-piperidine-1-carboxylic acid tert-butyl ester and 0.94 ml (8 mmol) of 2-chloro-5-(chloromethyl)thiophen. After standard work-up and purification, 2.86 g of 4-[1-(5-chlorothiophen-2-ylmethyl)-1H-pyrrolo[2,3-b]pyridin-3-yl]-piperidine-1-carboxylic acid tert-butyl ester were obtained.

B. Preparation of 1-(5-chlorothiophen-2-ylmethyl)-3-piperidin-4-yl-1H-pyrrolo[2,3-b]pyridine Over a solution of 2.86 g (6.6 mmol) of 4-[1-(5-chlorothiophen-2-ylmethyl)-1H-pyrrolo[2,3-b]pyridin-3-yl]-piperidine-1-carboxylic acid tert-butyl ester in 20 ml of dichloromethane, 5.1 ml of trifluoroacetic acid were added. After 1 hour at room temperature, the solvent was removed under reduced pressure. The crude mixture was dissolved in ethyl acetate and washed with saturated solution of potassium carbonate and brine. The organic phase was dried over magnesium sulphate, filtered and removed under reduced pressure affording 2.8 g of a crude mixture which was pure enough for the next synthetic step.

C. Preparation of 2-(2-{4-[1-(5-chlorothiophen-2-ylmethyl)-1H-pyrrolo[2,3-b]pyridin-3-yl]piperidin-1-yl}ethoxy)benzoic acid methyl ester This compound was prepared following the procedure described in example 4, part E starting with 2.8 g (6.5 mmol) of 1-(5-chloro-thiophen-2-ylmethyl)₃-piperidin-4-yl-1H-pyrrolo[2,3-b]pyridine and 1.5 g (7.2 mmol) of methyl 2-(2-chloroethoxy)benzoate. After standard work-up and purification, 1.1 g (33% yield) of 2-(2-{4-[1-(5-chlorothiophen-2-ylmethyl)-1H-pyrrolo[2,3-b]pyridin-3-yl]piperidin-1-yl}ethoxy)benzoic acid methyl ester were obtained.

D. Preparation of 2-(2-{4-[1-(5-chlorothiophen-2-ylmethyl)-1H-pyrrolo[2,3-b]pyridin-3-yl]piperidin-1-yl}ethoxy)benzoic acid This compound was prepared following the procedure described in example 4, part F starting with 1.1 g (2.2 mmol) of 2-(2-{4-[1-(5-chlorothiophen-2-ylmethyl)-1H-pyrrolo[2,3-b]pyridin-3-yl]piperidin-1-yl}ethoxy)benzoic acid methyl ester. After standard work-up and purification, 0.38 g (35% yield) were obtained.

Melting point=149.9-151.3° C.

NMR (300 MHz, DMSO-d6) δ=1.80-2.01 (m, 4H), 2.50-2.72 (m, 2H), 2.88-3.12 (m, 3H), 3.20-3.24 (m, 2H), 4.43 (m, 2H), 5.54 (s, 2H), 6.96-7.04 (m, 4H), 7.08-7.12 (t, 1H), 7.22-7.24 (d, 1H), 7.37-7.42 (m, 2H), 7.54-7.56 (d, 1H), 8.16-8.19 (d, 1H), 8.28-8.29 (d, 1H)

EXAMPLE 18

This compound was prepared following the procedure described in example 17, parts C and D, starting with 0.098 g (0.33 mmol) of 1-(5-chloro-thiophen-2-ylmethyl)-3-piperidin-4-yl-1H-pyrrolo[2,3-b]pyridine. The crude mixture was purified by preparative HPLC triggered by MS.

EXAMPLE 19

Preparation of 5-{4-[1-(5-chloro-thiophen-2-ylmethyl)-1H-pyrrolo[2,3]pyridin-3-yl]-piperidin-1-ylmethyl}-2-methoxy-benzoic acid This compound was prepared following the procedure described in example 4, part F, starting with 2.8 g (5.35 mmol) of 5-{4-[1-(5-chloro-thiophen-2-ylmethyl)-1H-pyrrolo[2,3-b]pyridin-3-yl]-piperidin-1-ylmethyl}-2-methoxy-benzoic acid ethyl ester. After standard work-up, 2 g (75% of yield) of the expected acid were obtained.

Melting point=200.9-202.0° C.

NMR (300 MHz, DMSO-d6) δ=1.63-1.69 (m, 2H), 1.90-1.95 (m, 2H), 2.72-2.78 (m, 1H), 2.89-2.93 (d, 2H), 3.51 (s, 2H), 3.81 (s, 3H), 5.51 (s, 2H), 6.94-6.98 (m, 2H), 7.06-7.10 (m, 2H), 7.40-7.46 (m, 2H), 7.59 (s, 1H), 8.01-8.04 (d, 1H), 8.25-8.26 (d, 1H).

EXAMPLES 20-23

These compounds were prepared following the procedure described in example 7, parts G and H, starting with 0.082 g (0.32 mmol) of 1-(2-methoxyethyl)$_3$-piperidinyl-1H-pyrrolo[2,3-b]pyridine. The crude mixtures were purified by preparative HPLC triggered by MS. ESI/MS and purity data corresponding to these compounds are shown in table 6.

A. Preparation of 1-(2-methoxyethyl)-3-piperidin-4-yl-1H-pyrrolo[2,3-b]pyridine This compound was prepared following the procedure described in example 7, parts E and F, starting with 0.2 g (0.66 mmol) of 4-(1H-pyrrolo[2,3-b]pyridin-3-yl)-piperidine-1-carboxylic acid tert-butyl ester and 0.081 ml (0.864 mmol) of 1-bromo-2-methoxyethane. After standard work-up, 0.15 g (100% of yield) of the expected product were isolated.

TABLE 6

| Example | ESI/MS m/e [(M)+] | Purity (%) |
|---------|-------------------|------------|
| 20 | 423 | 100 |
| 21 | 423 | 98 |
| 22 | 453 | 99 |
| 23 | 453 | 96 |

EXAMPLE 24

Preparation of 5-[4-(1-butyl-1H-pyrrolo[2,3-b]pyridin-3-yl)-piperidin-1-ylmethyl]-2-methoxybenzoic acid

A. Preparation of 4-(1H-pyrrolo[2,3-b]pyridin-3-yl)-3,6-dihydro-2H-pyridine-1-carboxylic acid ethyl ester A suspension 5.51 g (0.05 mol) of 7-azaindol, 9.6 g (0.056 mol) of 4-oxo-piperidine-1-carboxylic acid ethyl ester and 5 g (0.075 mol) of potassium hydroxide in 120 ml of methanol was heated at 75° C. for 16 hours. The crude mixture was cooled at room temperature and the precipitate formed was filtered off. 7.8 g (57% of yield) of 4-(1H-pyrrolo[2,3-b]pyridin-3-yl)-3,6-dihydro-2H-pyridine-1-carboxylic acid ethyl ester were obtained.

B. Preparation of 4-(1H-pyrrolo[2,3-b]pyridin-3-yl)-piperidine-1-carboxylic acid ethyl ester 7.8 g (0.029 mol) of 4-(1H-pyrrolo[2,3-b]pyridin-3-yl)-3,6-dihydro-2H-pyridine-1-carboxylic acid ethyl ester were dissolved in 250 ml of ethanol and 7.8 g of palladium over carbon at 10% were added. The crude mixture was hydrogenated at 30 psi for 24 hours. After filtering the catalyst and removal of the solvent at reduced pressure, 4.95 g (62% of yield) of 4-(1H-pyrrolo[2,3-b]pyridin-3-yl)-piperidine-1-carboxylic acid ethyl ester were obtained.

C. Preparation of 4-(1-butyl-1H-pyrrolo[2,3-b]pyridin-3-yl)-piperidine-carboxylic acid ethyl ester Under nitrogen atmosphere, over a suspension of 0.55 g (13.72 mmol) of sodium hydride 60% in paraffin oil in 10 ml of DMF, a solution of 2.5 g (9.1 mmol) of 4-(1H-pyrrolo[2,3-b]pyridin-3-yl)-piperidine-1-carboxylic acid ethyl ester in 10 ml of DMF was added. After 30 minutes, a solution of 1.2 ml of 4-bromobutane in 2 ml of DMF was added. The crude mixture was stirred at room temperature for 15 hours. The solvent was removed under reduced pressure and the crude was partionated between ethyl acetate and water. The organic phase was dried over sodium sulphate, filtered and the solvent was removed under reduced pressure affording 3.1 g of 4-(1-butyl-1H-pyrrolo[2,3-b]pyridin-3-yl)-piperidine-1-carboxylic acid ethyl ester.

D. Preparation of 1-butyl-3-piperidin-4-yl-1H-pyrrolo[2,3-b]pyridine

This compound was prepared following the procedure described in example 4, part D, starting with 3.1 g (9.1 mmol) of 4-(1-butyl-1H-pyrrolo[2,3-b]pyridin-3-yl)piperidine-1-carboxylic acid ethyl ester. After standard work-up, 2.23 g (95% yield) of 1-butyl-3-piperidinyl-1H-pyrrolo[2,3-b]pyridine were obtained.

E. Preparation of 5-[4-(1-butyl-1H-pyrrolo[2,3-b]pyridin-3-yl)-piperidin-1-ylmethyl]-2-methoxy-benzoic acid methyl ester Over a solution of 2.2 g (8.66 mmol) of 1-butyl-3-piperidinyl-1H-pyrrolo[2,3-b]pyridine in 40 ml of dichloromethane, 1.66 ml (9.52 mmol) of DIEA were added. Over the crude mixture, a solution of 2.6 g (9.5 mmol) of 5-bromomethyl-2-methoxy-benzoic acid ethyl ester in 5 ml of dichloromethane was carefully added. The crude mixture was stirred at room temperature for 16 hours and it was diluted with 50 ml of dichloromethane. The organic phase was washed with bicarbonate aqueous solution and brine. It was dried over sodium sulphate, filtered and the solvent removed under reduced pressure. The crude mixture was purified by chromatography over silica gel affording 2.9 g (77% yield) of 5-[4-(1-butyl-1H-pyrrolo[2,3-b]pyridin-3-yl)-piperidin-1-ylmethyl]-2-methoxy-benzoic acid methyl ester were obtained.

F. Preparation of 5-[4-(1-butyl-1H-pyrrolo[2,3-b]pyridin-3-yl)piperidin-1-ylmethyl]-2-methoxy-benzoic acid This compound was prepared following the procedure described in example 4, part F, starting with 1.45 g (3.22 mmol) of 5-[4-(1-butyl-1H-pyrrolo[2,3-b]pyridin-3-yl)-piperidin-1-ylmethyl]-2-methoxy-benzoic acid methyl ester. After standard work-up and purification, 0.83 g (92% yield) of 5-[4-(1-butyl-1H-pyrrolo[2,3-b]pyridin-3-yl)-piperidin-1-ylmethyl]-2-methoxy-benzoic acid were obtained.

Melting point=243-0-244.2° C.

NMR (300 MHz, DMSO-d6) δ=0.85-0.90 (t, 3H), 1.19-1.27 (m, 2H), 1.64-1.80 (m, 4H), 1.89-1.99 (m, 2H), 2.10-2.40 (m, 2H), 2.70-2.90 (m, 3H), 3.59-3.62 (m, 2H), 3.81 (s, 3H), 4.16-4.21 (t, 2H), 7.00-7.04 (dd, 1H), 7.08-7.11 (d, 1H), 7.33 (s, 1H), 7.42-7.49 (m, 1H), 7.58-7.63 (m, 1H), 7.95-8.00 (m, 1H) 8.18-8.22 (m, 1H)

EXAMPLES 25-26

Example 25 was prepared following the procedure described in example 4 (parts E and F) and example 26 was prepared following the procedure described in example 24 (parts E and F) starting with 0.059 g (0.23 mmol) of 1-butyl-3-piperidinyl-1H-pyrrolo[2,3-b]pyridine. The crude mixtures were purified by preparative HPLC triggered by MS. ESI/MS and purity data corresponding to these compounds are shown in table 7.

TABLE 7

| Example | ESI/MS m/e [(M)+] | Purity (%) |
|---|---|---|
| 25 | 421 | 100 |
| 26 | 391 | 96 |

EXAMPLES 27-29

Example 27 was prepared following the procedure described in example 4 (parts E and F) and example 28 and 29 were prepared following the procedure described in example 24 (parts E and F), starting with 0.080 g (0.32 mmol) of 1-cyclopropylmethyl-3-piperidin-4-yl-1H-pyrrolo[2,3-b]pyridine. The crude mixtures were purified by preparative HPLC triggered by MS. ESI/MS and purity data corresponding to these compounds are shown in table 8.

A. Preparation of 1-cyclopropylmethyl-3-piperidin-4-yl-1H-pyrrolo[2,3-b]pyridine This compound was prepared following the procedure described in example 24, parts C and D, starting with 0.3 g (1 mmol) of 4-(1H-pyrrolo[2,3-b]pyridin-3-yl)-piperidine-1-carboxylic acid ethyl ester and 0.175 g (1.23 mmol) of bromomethylcyclopropane. After standard work-up, 0.242 g (96% of yield) of the expected product were isolated.

TABLE 8

| Example | ESI/MS m/e [(M)+] | Purity (%) |
|---|---|---|
| 27 | 419 | 100 |
| 28 | 389 | 100 |
| 29 | 419 | 100 |

EXAMPLES 30-32

These compounds were prepared following the procedure described in example 4, parts E and F, starting with 0.080 g (0.32 mmol) of 1-isopropyl-3-piperidin-4-yl-1H-pyrrolo[2,3-b]pyridine. The crude mixtures were purified by preparative HPLC triggered by MS. ESI/MS and purity data corresponding to these compounds are shown in table 9.

A. Preparation of 1-isopropyl-3-piperidin 4-yl-1H-pyrrolo[2,3-b]pyridine

This compound was prepared following the procedure described in example 24, parts C and D, starting with 0.3 g (1 mmol) of 4-(1H-pyrrolo[2,3-b]pyridin-3-yl-piperidine-1-carboxylic acid ethyl ester and 0.159 g (1.23 mmol) of 2-bromopropane. After standard work-up, 0.242 g (100% of yield) of the expected product were isolated.

TABLE 9

| Example | ESI/MS m/e [(M)+] | Purity (%) |
|---|---|---|
| 30 | 407 | 98 |
| 31 | 377 | 66 |
| 32 | 407 | 99 |

EXAMPLES 33-35

These compounds were prepared following the procedure described in example 4, parts E and F, starting with 0.066 g (0.22 mmol) of 1-(4-fluorobenzyl)-3-piperidin-4-yl-1H-pyrrolo[2,3-b]pyridine. The crude mixtures were purified by preparative HPLC triggered by MS. ESI/MS and purity data corresponding to these compounds are shown in table 10.

A. Preparation of 1-(4-fluorobenzyl)-3-piperidin-4-yl-1H-pyrrolo[2,3-b]pyridine

This compound was prepared following the procedure described in example 24, parts C and D, starting with 0.2 g (0.66 mmol) of 4-(1H-pyrrolo[2,3-b]pyridin-3-yl)-piperidine-1-carboxylic acid ethyl ester and 0.163 g (0.86 mmol) of 2-bromomethylpyridine. After standard work-up, 0.21 g (68% of yield) of the expected product were isolated.

TABLE 10

| Example | ESI/MS m/e [(M)+] | Purity (%) |
|---|---|---|
| 33 | 473 | 80 |
| 34 | 395 | 100 |
| 35 | 411 | 82 |

EXAMPLE 36

Preparation of 2-(2-{4-[1-(2-ethoxyethyl)-1H-pyrrolo[2,3-b]pyridin-3-yl]-piperidin-1-yl}-ethoxy)-4-methoxybenzoic acid A. Preparation of 4-[1-(2-ethoxyethyl)-1H-pyrrolo[2,3-b]pyridin-3-yl]-piperidine-1-carboxylic acid ethyl ester This compound was prepared following the procedure described in example 24, part C, starting with 2.8 g (10 mmol) of 4-(1H-pyrrolo[2,3-b]pyridin-3-yl)-piperidine-1-carboxylic acid ethyl ester and 1.7 ml (15 mmol) of 2-bromoethylethyl ether. After standard work-up and purification, 3.5 g of 4-[1-(2-ethoxyethyl)-1H-pyrrolo[2,3-b]pyridin-3-yl]-piperidine-1-carboxylic acid ethyl ester were obtained.

B. Preparation of 1-(2-ethoxyethyl)-3-piperidinyl-1H-pyrrolo[2,3-b]pyridine

This compound was prepared following the procedure described in example 24, part D, starting with 3.5 g (10 mmol) 4-[1-(2-ethoxyethyl)-1H-pyrrolo[2,3-b]pyridin-3-yl]-piperidine-1-carboxylic acid ethyl ester. After standard work-up, 3 g (84% yield) of 1-(2-ethoxyethyl)-3-piperidin-4-yl-1H-pyrrolo[2,3-b]pyridine were obtained.

C. Preparation of 2-(2-{4-[1-(2-ethoxyethyl)-1H-pyrrolo[2,3-b]pyridin-3-yl]-piperidin-1-yl}-ethoxy)-4-methoxy-benzoic acid methyl ester This compound was prepared following the procedure described in example 4, part E, starting with 3 g (10.9 mmol) of 1-(2-ethoxyethyl)-3-piperidin yl-1H-pyrrolo[2,3-b]pyridine and 4 g (16.5 mmol) of 2-(2-chloroethoxy)-4-methoxy-benzoic acid methyl ester. After standard work-up and purification, 2.3 g (44% yield) of 2-(2-{4-[1-(2-ethoxyethyl)-1H-pyrrolo[2,3-b]pyridin-3-yl]-piperidin-1-yl}-ethoxy)-4-methoxy-benzoic acid methyl ester were obtained.

D. Preparation of 2-(2-{4-[1-(2-ethoxyethyl)-1H-pyrrolo[2,3-b]pyridin-3-yl]-piperidin-1-yl}-ethoxy)-4-methoxy-benzoic acid This compound was prepared following the procedure described in example 4, part F, starting with 2.5 g (4.77 mmol) of 2-(2-{4-[1-(2-ethoxyethyl)-1H-pyrrolo[2,3-b]pyridin-3-yl]-piperidin-1-yl}-ethoxy)-4-methoxy-benzoic acid methyl ester. After standard work-up and purification, 0.8 g (36% yield) of 2-(2-{4-[1-(2-ethoxyethyl)-1H-pyrrolo[2,3-b]pyridin-3-yl]-piperidin-1-yl}ethoxy)-4-methoxy-benzoic acid were obtained.

Melting point=106.1-107.5° C.

NMR (300 MHz, DMSO-d6) δ=1.03-1.07 (t, 3H), 1.81-2.05 (m, 4H), 2.59-2.65 (t, 2H), 2.81-3.01 (m, 3H), 3.26-3.29 (d, 2H), 3.38-3.45 (dd, 2H), 3.69-3.73 (t, 2H), 3.82 (s, 3H), 4.34-4.41 (m, 4H), 6.61-6.64 (d, 1H), 6.77 (m, 1H), 7.03-7.07 (dd, 1H), 7.33 (s, 1H), 7.64-7.67 (d, 1H), 8.08-8.11 (d, 1H), 8.22-8.23 (d, 1H)

EXAMPLES 37-42

These compounds were prepared following the procedure described in example 36. They were purified by preparative HPLC triggered by MS. ESI/MS and purity data are shown in table 11.

TABLE 11

| Example | ESI/MS m/e [(M)+] | Purity (%) |
| --- | --- | --- |
| 37 | 467 | 100 |
| 38 | 471 | 91 |
| 39 | 425 | 100 |
| 40 | 437 | 95 |
| 41 | 467 | 97 |
| 42 | 467 | 92 |

EXAMPLE 43

Preparation of 2-{2-[4-(1-furan-3-ylmethyl-1H-pyrrolo[2,3-b]pyridin-3-yl)-piperidin-1-yl]-ethoxy}-4-methoxy-benzoic acid

A. Preparation of 4-(1H-pyrrolo[2,3-b]pyridin-3-yl)-3,6-dihydro-2H-pyridine-1-carboxylic acid ethyl ester Over a solution of 28 g (0.42 mol) of potassium hydroxide in 300 ml of ethanol, a solution of 20 g (0.17 mol) of 7-azaindol in 40 ml of ethanol was added. Over the crude mixture, 32.1 ml (0.21 mol) of 4-oxo-piperidine-1-carboxylic acid ethyl ester were added. The crude mixture was refluxed for 18 hours. It was partionated between ethyl acetate and water. The organic phase was dried over sodium sulphate, filtered and the solvent was removed under reduced pressure. The residue was crystallised with ethyl acetate affording 16 g (50% yield) of 4-(1H-pyrrolo[2,3-b]pyridin-3-yl)-3,6-dihydro-2H-pyridine-1-carboxylic acid ethyl ester.

B. Preparation of 4-(1H-pyrrolo[2,3-b]pyridin-3-yl)-piperidine-1-carboxylic acid ethyl ester 3.3 g (12 mmol) of 4-(1H-pyrrolo[2,3-b]pyridin-3-yl)-3,6-dihydro-2H-pyridine-1-carboxylic acid ethyl ester were dissolved in 15 ml of ethanol and 5 ml of THF. Over this solution, 3.3 g of Pd over carbon at 10% were added. The crude mixture was hydrogenated at 30 psi for 48 hours. The catalyst was filtered off and the solvent removed under reduced pressure affording 1.55 g (54%) of 4-(1H-pyrrolo[2,3-b]pyridin-3-yl)-piperidine-1-carboxylic acid ethyl ester.

C. Preparation of 4-(1-furan-3-ylmethyl-1H-pyrrolo[2,3-b]pyridin-3-yl)-piperidine-1-carboxylic acid ethyl ester This compound was prepared following the procedure described in example 24, part C, starting with 3 g (11 mmol) of 4-(1H-pyrrolo[2,3-b]pyridin-3-yl)piperidine-1 carboxylic acid ethyl ester and 20 ml of a 0.6M solution of 3-bromomethylfuran freshly prepared. After standard work-up, 4.44 g of 4-(1-furan-3-ylmethyl-1H-pyrrolo[2,3-b]pyridin-3-yl)-piperidine-1-carboxylic acid ethyl ester were obtained.

D. Preparation of 1-furan-3-ylmethyl-3-piperidinyl-1H-pyrrolo[2,3-b]pyridine This compound was prepared following the procedure described in example 24, part D, starting with 4.44 g (11 mmol) of 4-(1-furan-3-ylmethyl-1H-pyrrolo[2,3-b]pyridin-3-yl) piperidine-1-carboxylic acid ethyl ester and 3.6 g of potassium hydroxide. After standard work-up, 3.85 g of 1-furan-3-ylmethyl-3-piperidinyl-1H-pyrrolo[2,3-b]pyridine were obtained.

E. Preparation of 2-{2-[4-(1-furan-3-ylmethyl-1H-pyrrolo[2,3-b]pyridin-3-yl)piperidin-1-yl]-ethoxy}-4-methoxy-benzoic acid methyl ester This compound was prepared following the procedure described in example 4, part E, starting with 3.8 g (11 mmol) of 1-furan-3-ylmethyl-3-piperidin yl-1H-pyrrolo[2,3-b]pyridine and 4.03 g (16.5 mmol) of 2-(2-chloroethoxy)-4-methoxy-benzoic acid methyl ester. After standard work-up and purification, 2.5 g (50% yield) of 22-[4-(1-furan-3-ylmethyl-1H-pyrrolo[2,3-b]pyridin-3-yl)piperidin-1-yl]-ethoxy)-4-methoxy-benzoic acid methyl ester were obtained.

F. Preparation of 2-{2-[4-(1-furan-3-ylmethyl-1H-pyrrolo[2,3-b]pyridin-3-yl)-piperidin-1-yl]-ethoxy}4 methoxy-benzoic acid This compound was prepared following the procedure described in example 4, part F, starting with 2.5 g (5.1 mmol) of 2-{2-[4-(1-furan-3-ylmethyl-1H-pyrrolo[2,3-b]pyridin-3-yl)-piperidin-1-yl]-ethoxy}-4-methoxy-benzoic acid methyl ester. After standard work-up and purification, 1.2 g (50% yield) of 2-{2-[4-(1-furan-3-ylmethyl-1H-pyrrolo[2,3-b]pyridin-3-yl)-piperidin-1-yl]-ethoxy}4-methoxybenzoic acid were obtained.

Melting point=91.5-93.2° C.

NMR (300 MHz, DMSO-d6) δ=1.79-1.98 (m, 4H), 2.40-2.48 (t, 2H), 2.76-2.93 (m, 3H), 3.23-315 (m, 2H), 3.81 (s, 3H), 4.30-4.46 (m, 2H), 5.26 (s, 2H), 6.45 (s, 1H), 6.60-6.63 (m, 1H), 6.77-6.79 (m, 1H), 7.05-7.09 (m, 1H), 7.34 (s, 1H), 7.57-7.66 (m, 2H), 8.10-8.12 (dd, 1H), 8.35-8.27 (m, 1H)

EXAMPLE 44

Preparation of 4-chloro-2-{2-[4-(1-furan-3-ylmethyl-1H-pyrrolo[2,3-b]pyridin-3-yl)-piperidin-1-yl]-ethoxy}-benzoic acid This compound was prepared following the procedure described in example 4, parts E and F, starting with 1.5 g (5.3 mmol) of 1-furan-3-ylmethyl-3-piperidin-4-yl-1H-pyrrolo[2,3-b]pyridine and 1.7 g (6.9 mmol) of 2-(2-chloroethoxy)-4-chlorobenzoic acid methyl ester. After standard work-up and purification, 0.3 g (10% yield) of 4-chloro-2-{2-[4-(1-furan-3-ylmethyl-1H-pyrrolo[2,3-b]pyridin-3-yl)-piperidin-1-yl]-ethoxy}-benzoic acid were obtained.

Melting point=81.6-83.3° C.

NMR (300 MHz, DMSO-d6) δ=1.88-2.14 (m, 4H), 2.70-2.77 (t, 2H), 2.87-2.96 (m, 1H), 3.04-3.08 (t, 2H), 3.29-3.33 (m, 2H), 4.48-4.51 (t, 2H), 5.26 (s, 2H), 6.45 (s, 1H), 7.05-7.10 (m, 2H), 7.33-7.38 (m, 2H), 7.52-7.58 (m, 2H), 7.67 (s, 1H), 8.16-8.22 (dd, 1H), 8.26-8.28 (dd, 1H)

EXAMPLE 45-49

These compounds were prepared following the procedure described in example 44. They were purified by preparative HPLC triggered by MS. ESI/MS and purity data are shown in table 12.

TABLE 12

| Example | ESI/MS m/e [(M)+] | Purity (%) |
|---|---|---|
| 45 | 433 | 100 |
| 46 | 475 | 99 |
| 47 | 445 | 88 |
| 48 | 475 | 91 |
| 49 | 475 | 85 |

EXAMPLE 50

Preparation of 2-{2-[4-(1-furan-2-ylmethyl-1H-pyrrolo[2,3-b]pyridin-3-yl)-piperidin-1-yl]-ethoxy}-4-methoxy-benzoic acid This compound was prepared following the procedure described in example 4, part E and F starting with 3.6 g (11 mmol) of 1-furan-2-ylmethyl-3-piperidin-4-yl-1H-pyrrolo[2,3-b]pyridine and 4.0 g (16.5 mmol) of 2-(2-chloroethoxy)-4-methoxy-benzoic acid methyl ester. After standard purification the overall yield was 36% (1.93 g).

Melting point=186.9-189.2° C.

NMR (300 MHz, DMSO-d6) δ=1.93-2.09 (m, 4H), 2.47-2.54 (m, 2H), 2.76-3.01 (m, 3H); 3.15-3.23 (m, 2H), 3.37-3.50 (m, 2H), 3.82 (s, 3H), 4.45 (m, 2H), 5.43 (s, 2H), 6.40 (m, 2H), 6.62-6.65 (dd, 1H), 6.75-6.76 (m, 1H), 7.07-7.11 (dd, 1H), 7.33 (s, 1H), 7.58 (s, 1H), 7.68-7.71 (d, 1H), 8.13-8.15 (d, 1H), 8.26-8.27 (d, 1H)

EXAMPLES 51-53

These compounds were prepared following the procedure described in example 50. They were purified by preparative HPLC triggered by MS. ESI/MS and purity data are shown in table 13.

TABLE 13

| Example | ESI/MS m/e [(M)+] | Purity (%) |
|---|---|---|
| 51 | 475 | 99 |
| 52 | 479 | 95 |
| 53 | 433 | 100 |

EXAMPLE 54

Preparation of 2-(2-{4-[1-(5-chlorothiophen-2-ylmethyl)-1H-pyrrolo[2,3-b]pyridin-3-yl]-piperidin-1-yl}-ethoxy)-3-methoxy-benzoic acid This compound was prepared following the procedure described in example 4, part E and F starting with 2 g (6 mmol) of 1-(5-chlorothiophen-2-ylmethyl)-3-piperidin-4-yl-1H-pyrrolo[2,3-b]pyridine and 1.9 g (7.85 mmol) of 2-(2-chloroethoxy)-3-methoxy-benzoic acid methyl ester. After standard purification the overall yield was 14% (0.8 g).

Melting point=110.7-112.6° C.

NMR (300 MHz, DMSO-d6) δ=1.90-2.14 (m, 4H), 2.70-2.80 (m, 2H), 2.90-3.11 (m, 3H), 3.25-3.32 (m, 2H), 3.81 (s, 3H), 4.38-4.46 (d, 2H), 5.54 (s, 2H), 6.93-7.15 (m, 6H), 7.44 (s, 1H), 8.21-8.24 (dd, 1H), 8.27-8.30 (dd, 1H)

EXAMPLES 55-60

These compounds were prepared following the procedure described in example 54. They were purified by preparative HPLC triggered by MS. ESI/MS and purity data are shown in table 14.

TABLE 14

| Example | ESI/MS m/e [(M)+] | Purity (%) |
|---|---|---|
| 55 | 526 | 88 |
| 56 | 530 | 92 |
| 57 | 483 | 99 |
| 58 | 496 | 70 |
| 59 | 526 | 71 |
| 60 | 526 | 82 |

EXAMPLE 61

Preparation of 2-{2-[4-(1-butyl-1H-pyrrolo[2,3-b]pyridin-3-yl)-piperidin-1-yl]-ethoxy}-4-methoxy-benzoic acid This compound was prepared following the procedure described in example 4, part E and F starting with 2.5 g (9.1 mmol) of 1-butyl-3-piperidinyl-1H-pyrrolo[2,3-b]pyridine and 3.3 g (13.6 mmol) of 2-(2-chloroethoxy)-4-methoxy-benzoic acid methyl ester. After standard purification the overall yield was 35% (0.77 g).

Melting point=175-177° C.

NMR (300 MHz, DMSO-d6) δ=0.86-0.91 (t, 3H), 1.18-1.31 (m, 2H), 1.70-1.80 (m, 2H), 1.92-2.10 (m, 4H), 2.75-3.00 (m, 3H), 3.13-3.23 (m, 2H), 3.36-3.45 (m, 2H), 3.82 (s, 3H), 4.18-4.23 (t, 2H), 4.43-4.46 (t, 2H), 6.62-6.66 (dd, 1H), 6.74-6.76 (d, 1H), 7.02-7.06 (dd, 1H), 7.35 (s, 1H), 7.68-7.71 (d, 1H), 8.09-8.11 (m, 1H), 8.22-8.23 (m, 1H)

EXAMPLES 62-67

These compounds were prepared following the procedure described in example 61. They were purified by preparative HPLC triggered by MS. ESI/MS and purity data are shown in table 15.

TABLE 15

| Example | ESI/MS m/e [(M)+] | Purity (%) |
|---|---|---|
| 62 | 451 | 95 |
| 63 | 455 | 99 |
| 64 | 409 | 99 |
| 65 | 421 | 97 |
| 66 | 451 | 100 |
| 67 | 451 | 90 |

EXAMPLES 68-69

These compounds were prepared following the procedure described in example 4, parts E and F, starting with 0.066 g (0.22 mmol) of 3-piperidinyl-1-pyridin-2-ylmethyl-1H-pyrrolo[2,3-b]pyridine. The crude mixtures were purified by preparative HPLC triggered by MS. ESI/MS and purity data corresponding to these compounds are shown in table 16.

A. Preparation of 3-piperidin-4-yl-1-pyridin-2-ylmethyl-1H-pyrrolo[2,3-b]pyridine This compound was prepared following the procedure described in example 24, parts C and D, starting with 0.2 g (0.66 mmol) of 4-(1H-pyrrolo[2,3-b]pyridin-3-yl)-piperidine-1-carboxylic acid ethyl ester and 0.149 g (0.86 mmol) of 2-bromomethylpyridine. After standard work-up, 0.21 g (72% of yield) of the expected product were isolated.

TABLE 16

| Example | ESI/MS m/e [(M)+] | Purity (%) |
|---|---|---|
| 68 | 456 | 73 |
| 69 | 378 | 100 |

EXAMPLE 70

Preparation of 2-(2-{4-[1-(2-ethoxyethyl)-1H-pyrrolo[2,3-c]pyridin-3-yl]-piperidin-1-yl}-ethoxy)-benzoic acid

A. Preparation of 4-(1H-pyrrolo[2,3c]pyridin-3-yl) piperidine-1-carboxylic acid ethyl ester This compound was prepared following the procedure described in example 24, parts A and B, starting with 3.1 g (26.24 mmol) of 6-azaindol and 4.36 ml (28.86 mmol) of 1-carbethoxy-4-piperidona. After two synthetic steps, 3.1 g (91% yield) were obtained.

B. Preparation of 4-[1-(2-ethoxyethyl)-1H-pyrrolo[2,3-c]pyridin-3-yl]-piperidine-1-carboxylic acid ethyl ester This compound was prepared following the procedure described in example 24, part C, starting with 1.05 g (3.84 mmol) of 4-(1H-pyrrolo[2,3-c]pyridin-3-yl)-piperidine-1-carboxylic acid ethyl ester and 0.52 ml (4.61 mmol) of 2-bromoethylethyl ether. After standard work-up and purification, 0.83 g (63% yield) 4-[1-(2-ethoxyethyl)-1H-pyrrolo[2,3-c]pyridin-3-yl]-piperidine-1-carboxylic acid ethyl ester were obtained.

C. Preparation of 1-(2-ethoxyethyl)-3-piperidin-4-yl-1H-pyrrolo[2,3]pyridine This compound was prepared following the procedure described in example 24, part D, starting with 0.83 g (2.4 mmol) of 4-[1-(2-ethoxyethyl)-1H-pyrrolo[2,3-c]pyridin-3-yl]-piperidine-1-carboxylic acid ethyl ester. After standard work-up, 0.46 g (71% yield) of 1-(2-ethoxyethyl)-3-piperidinyl-1H-pyrrolo[2,3-c]pyridine were obtained.

D. Preparation of 2-(2-{4-[1-(2-ethoxyethyl)-1H-pyrrolo[2,3c]pyridin-3-yl]-piperidin-1-yl}ethoxy)-benzoic acid methyl ester This compound was prepared following the procedure described in example 4, part E, starting with 0.46 g (1.7 mmol) of 1-(2-ethoxyethyl)-3-piperidin yl-1H-pyrrolo[2,3-c]pyridine and 0.44 g (2.0 mmol) of 2-(2-chloroethoxy)-benzoic acid methyl ester. After standard work-up and purification, 0.2 g (21% yield) of 2-(2-{4-[1-(2-ethoxyethyl)-1H-pyrrolo[2,3-c]pyridin-3-yl]-piperidin-1-yl}-ethoxy)benzoic acid methyl ester were obtained.

E. Preparation of 2-(2-{4-[1-(2-ethoxyethyl)-1H-pyrrolo[2,3-c]pyridin-3-yl]-piperidin-1-yl}-ethoxy) benzoic acid This compound was prepared following the procedure described in example 4, part F, starting with 0.21 g (0.46 mmol) of 2-(2-{4-[1-(2-ethoxyethyl)-1H-pyrrolo[2,3-c]pyridin-3-yl]-piperidin-1-yl}-ethoxy)-benzoic acid methyl ester. After standard work-up and purification, 0.18 g (90% yield) of 5-[4-(1-butyl-1H-pyrrolo[2,3-b]pyridin-3-yl)piperidin-1-ylmethyl]-2-methoxy-benzoic acid were obtained.

Melting point=173.8-175.1° C.

NMR (300 MHz, DMSO-d6) δ=0.99-1.05 (m, 3H), 2.05-2.09 (m, 2H), 2.20-2.30 (m, 2H), 3.14-3.52 (m, 7H), 3.70-3.73 (t, 4H), 4.52-4.58 (m, 4H), 7.04-7.09 (t, 1H), 7.20-7.23 (d, 1H), 7.52-7.57 (t, 1H), 7.67-7.70 (d, 1H), 7.82 (s, 1H), 8.04-8.06 (d, 1H), 8.20-8.22 (d, 1H), 9.13 (s, 1H)

EXAMPLES 71-75

These compounds were prepared following the procedure described in example 70. They were purified by preparative HPLC triggered by MS. ESI/MS and purity data are shown in table 17.

TABLE 17

| Example | ESI/MS m/e [(M)+] | Purity (%) |
|---|---|---|
| 71 | 467 | 100 |
| 72 | 467 | 100 |

TABLE 17-continued

| Example | ESI/MS m/e [(M)+] | Purity (%) |
|---|---|---|
| 73 | 471 | 98 |
| 74 | 437 | 86 |
| 75 | 486 | 92 |

EXAMPLE 76

Preparation of 2-{2-[4-(1-furan-3-ylmethyl-1H-pyrrolo[2,3-c]pyridin-3-yl)-piperidin-1-yl]-ethoxy}-4-methoxy-benzoic acid A. Preparation of 4-(1-furan-3-ylmethyl-1H-pyrrolo[2,3-c]pyridin-3-yl)piperidine-1-carboxylic acid ethyl ester This compound was prepared following the procedure described in example 24, part C, starting with 4.9 g (18 mmol) of 4-(1H-pyrrolo[2,3-c]pyridin-3-yl)-piperidine-1-carboxylic acid ethyl ester and 35.4 ml (21.6 mmol) of a 0.61 M solution of 3-bromomethylfurane. After standard work-up and purification, 5.72 g (91% of yield) of 4-(1-furan-3-ylmethyl-1H-pyrrolo[2,3c]pyridin-3-yl)piperidine-1-carboxylic acid ethyl ester were obtained.

B. Preparation of 1-furan-3-ylmethyl-3-piperidinyl-1H-pyrrolo[2,3-c]pyridine

This compound was prepared following the procedure described in example 4, part D, starting with 5.72 g (16.2 mmol) of 4-(1-furan-3-ylmethyl-1H-pyrrolo[2,3-c]pyridin-3-yl)-piperidine-1-carboxylic acid ethyl ester. After standard work-up, 4.3 g (93% yield) of 1-furan-3-ylmethyl-3-piperidinyl-1H-pyrrolo[2,3-c]pyridine were obtained.

C. Preparation of 2-{2-[4-(1-furan-3-ylmethyl-1H-pyrrolo[2,3-c]pyridin-3-yl)piperidin-1-yl]-ethoxy}-4-methoxy-benzoic acid methyl ester This compound was prepared following the procedure described in example 4, part E, starting with 1.50 g (5.25 mmol) of 1-furan-3-ylmethyl-3-piperidin-4-yl-1H-pyrrolo[2,3-c]pyridine and 1.55 g (6.3 mmol) of 2-(2-chloroethoxy)-4-methoxybenzoic acid methyl ester. After standard work-up and purification, 0.95 g (36% yield) of 2-{2-[4-(1-furan-3-ylmethyl-1H-pyrrolo[2,3-c]pyridin-3-yl)-piperidin-1-yl]-ethoxy}-4-methoxy-benzoic acid methyl ester were obtained.

D. Preparation of 2-{2-[4-(1-furan-3-ylmethyl-1H-pyrrolo[2,3-c]pyridin-3-yl)-piperidin-1-yl]-ethoxy}-4-methoxy-benzoic acid This compound was prepared following the procedure described in example 4, part F, starting with 0.95 g (1.94 mmol) of 2-{2-[4-(1-furan-3-ylmethyl-1H-pyrrolo[2,3-c]pyridin-3-yl)-piperidin-1-yl]-ethoxy}4 methoxy-benzoic acid methyl ester. After standard work-up and purification, 0.27 g (30% yield) of 2-{2-[4-(1-furan-3-ylmethyl-1H-pyrrolo[2,3-c]pyridin-3-yl)piperidin-1-yl]-ethoxy}-methoxy-benzoic acid were obtained.

Melting point=303.4-304.5° C.

NMR (300 MHz, DMSO-d6) δ=1.72-2.00 (m, 4H), 2.33-2.58 (m, 2H), 2.73-2.93 (m, 3H), 3.14-3.17 (m, 2H), 3.79 (s, 3H), 4.37 (s, 2H), 5.28 (s, 3H), 6.42 (s, 1H), 6.59-6.62 (s, 1H), 6.76 (s, 1H), 7.47 (s, 1H), 7.57-7.63 (m, 3H), 7.78 (s, 1H), 8.00 (m, 1H), 9.00 (m, 1H)

EXAMPLES 77-80

These compounds were prepared following the procedure described in example 76. They were purified by preparative HPLC triggered by MS. ESI/MS and purity data are shown in table 18.

TABLE 18

| Example | ESI/MS m/e [(M)+] | Purity (%) |
|---|---|---|
| 77 | 445 | 94 |
| 78 | 445 | 83 |
| 79 | 445 | 75 |
| 80 | 479 | 100 |

EXAMPLE 81

Preparation of 2-{2-[4-(1-butyl-1H-pyrrolo[2,3-c]pyridin-3-yl)-piperidin-1-yl]-ethoxy}-benzoic acid A. Preparation of 4-(1-butyl-1H-pyrrolo[2,3-c]pyridin-3-yl)-piperidine-1-carboxylic acid ethyl ester This compound was prepared following the procedure described in example 24, part C, starting with 4.9 g (18 mmol) of 4-(1H-pyrrolo[2,3-c]pyridin-3-yl)-piperidine-1-carboxylic acid ethyl ester and 35.4 ml (21.6 mmol) of a 0.61 M solution of 3-bromomethylfurane. After standard work-up and purification, 6.14 g (43% of yield) of 4-(1-butyl-1H-pyrrolo[2,3-c]pyridin-3-yl)-piperidine-1-carboxylic acid ethyl ester were obtained.

B. Preparation of 1-butyl-3-piperidinyl-1H-pyrrolo[2,3-c]pyridine

This compound was prepared following the procedure described in example 24, part D, starting with 6.14 g (18.6 mmol) of 4-(1-butyl-1H-pyrrolo[2,3]pyridin-3-yl)piperidine-1-carboxylic acid ethyl ester. After standard work-up, 5.45 g (100% yield) of 1-butyl-3-piperidinyl-1H-pyrrolo[2,3-c]pyridine were obtained.

C. Preparation of 2-{2-[4-(1-butyl-1H-pyrrolo[2,3]pyridin-3-yl)piperidin-1-yl]-ethoxy}-benzoic acid methyl ester This compound was prepared following the procedure described in example 4, part E, starting with 1.35 g (5.25 mmol) of 1-butyl-3-piperidin yl-1H-pyrrolo[2,3-c]pyridine and 1.35 g (6.3 mmol) of 2-(2-chloroethoxy)benzoic acid methyl ester. After standard work-up and purification, 1.1 g (49% yield) of 2-{2-[4-(1-butyl-1H-pyrrolo[2,3-c]pyridin-3-yl)-piperidin-1-yl]-ethoxy}-benzoic acid methyl ester were obtained.

D. Preparation of 2-{2-[4-(1-butyl-1H-pyrrolo[2,3-c]pyridin-3-yl)-piperidin-1-yl]-ethoxy}-benzoic acid This compound was prepared following the procedure described in example 4, part F, starting with 1.1 g (2.57 mmol) of 2-{2-[4-(1-butyl-1H-pyrrolo[2,3-c]pyridin-3-yl)-piperidin-1-yl]-ethoxy}-benzoic acid methyl ester. After standard work-up and purification, 0.42 g (42% yield) of 2-{2-[4-(1-butyl-1H-pyrrolo[2,3-c]pyridin-3-yl)-piperidin-1-yl]ethoxy}-benzoic acid were obtained.

Melting point=157.8-158.8° C.

NMR (300. MHz, DMSO-d6) δ=0.86-0.91 (t, 3H), 1.18-1.31 (m, 2H), 1.70-1.80 (m, 2H), 1.89-2.02 (m, 4H), 2.58-2.69 (m, 2H), 2.82-3.01 (m, 3H), 3.19-3.23 (d, 2H), 4.21-4.25 (t, 2H), 4.41-4.45 (t, 2H), 6.69-7.04 (t, 1H), 7.22-7.24 (d, 1H), 7.36-7.44 (m, 2H), 7.53-7.56 (dd, 1H), 7.65-7.67 (d, 1H), 8.07-8.09 (d, 1H), 8.83 (s, 1H)

EXAMPLES 82-87

These compounds were prepared following the procedure described in example 81. They were purified by preparative HPLC triggered by MS. ESI/MS and purity data are shown in table 19.

TABLE 19

| Example | ESI/MS m/e [(M)+] | Purity (%) |
|---------|-------------------|------------|
| 82 | 451 | 100 |
| 83 | 451 | 100 |
| 84 | 455 | 100 |
| 85 | 421 | 95 |
| 86 | 470 | 100 |
| 87 | 391 | 92 |

EXAMPLE 88

Preparation of 5-{4-[1-(5-chloro-thiophen-2-ylmethyl)-1H-pyrrolo[2,3-c]pyridin-3-yl]-piperidin-1-ylmethyl}-2-methoxy-benzoic acid A. Preparation of 4-[1-(5-chlorothiophen-2-ylmethyl)-1H-pyrrolo[2,3-c]pyridin-3-yl]-piperidine-1-carboxylic acid ethyl ester This compound was prepared following the procedure described in example 24, part C, starting with 8.7 g (31.8 mmol) of 4-(1H-pyrrolo[2,3-c]pyridin-3-yl)-piperidine-1-carboxylic acid ethyl ester and 5.75 ml (47.7 mmol) of 2-chloro-5-chloromethylthiophen. After standard work-up and purification, 7.67 g (60% of yield) of 4-[1-(5-chlorothiophen-2-ylmethyl)-1H-pyrrolo[2,3-c]pyridin-3-yl]-piperidine-1-carboxylic acid ethyl ester were obtained.

B. Preparation of 1-(5-chlorothiophen-2-ylmethyl)-3-piperidinyl-1H-pyrrolo[2,3-c]pyridine This compound was prepared following the procedure described in example 24, part D, starting with 7.67 g (19 mmol) of 4-[1-(5-chlorothiophen-2-ylmethyl)-1H-pyrrolo[2,3-c]pyridin-3-yl]-piperidine-1-carboxylic acid ethyl ester. After standard work-up, 2.94 g (46% yield) of 1-(5-chlorothiophen-2-ylmethyl)-3-piperidin-4-yl-1H-pyrrolo[2,3-c]pyridine.

C. Preparation of 5-{4-[1-(5-chloro-thiophen-2-ylmethyl)-1H-pyrrolo[2,3]pyridin-3-yl]-piperidin-1-ylmethyl}-2-methoxy-benzoic acid ethyl ester This compound was prepared following the procedure described in example 24, part E, starting with 0.44 g (1.32 mmol) of 1-(5-chlorothiophen-2-ylmethyl)-3-piperidin-4-yl-1H-pyrrolo[2,3-c]pyridine and 0.36 g (1.32 mmol) of 5-bromomethyl-2-methoxybenzoic acid ethyl ester. After standard work-up and purification, 0.3 g (43% yield) of 5-{4-[1-(5-chlorothiophen-2-ylmethyl)-1H-pyrrolo[2,3-c]pyridin-3-yl]-piperidin-1-ylmethyl}-2-methoxy-benzoic acid ethyl ester were obtained.

D. Preparation of 5-{4-[1-(5-chlorothiophen-2-ylmethyl)-1H-pyrrolo[2,3-c]pyridin-3-yl]-piperidin-1-ylmethyl}-2-methoxy-benzoic acid This compound was prepared following the procedure described in example 24, part F, starting with 0.3 g (0.57 mmol) of 5-{4-[1-(5-chlorothiophen-2-ylmethyl)-1H-pyrrolo[2,3-c]pyridin-3-yl]-piperidin-1-ylmethyl}-2-methoxy-benzoic acid ethyl ester. After standard work-up and purification, 0.2 g (60% yield) of 5-{4-[1-(5-chloro-thiophen-2-ylmethyl)-1H-pyrrolo[2,3-c]pyridin-3-yl]-piperidin-1-ylmethyl}-2-methoxy-benzoic acid were obtained.

Melting point=125.0-127.2° C.

NMR (300 MHz, DMSO-d6) δ=1.62-1.71 (m, 2H), 1.89-1.94 (m, 2H), 2.07-2.14 (m, 2H), 2.71-2.82 (m, 1H), 2.87-2.95 (m, 2H), 3.47 (s, 2H), 3.80 (s, 3H), 5.60 (s, 2H), 6.98 (s, 1H), 7.06-7.09 (m, 2H), 7.42-7.45 (m, 1H), 7.50 (s, 1H), 7.56-7.58 (m, 2H), 8.08 (s, 1H), 8.89 (m, 1H).

EXAMPLES 89-93

These compounds were prepared following the procedure described in example 88. They were purified by preparative HPLC triggered by MS. ESI/MS and purity data are shown in table 20.

TABLE 20

| Example | ESI/MS m/e [(M)+] | Purity (%) |
|---------|-------------------|------------|
| 89 | 496 | 68 |
| 90 | 526 | 70 |
| 91 | 526 | 62 |
| 92 | 530 | 54 |
| 93 | 433 | 20 |

EXAMPLE 94-99

These compounds were prepared following the procedure described in example 89 starting with the corresponding starting materials. They were purified by preparative HPLC triggered by MS. ESI/MS and purity data are shown in table 21.

TABLE 21

| Example | ESI/MS m/e [(M)+] | Purity (%) |
|---------|-------------------|------------|
| 94 | 461 | 100 |
| 95 | 445 | 93 |
| 96 | 445 | 97 |
| 97 | 491 | 93 |
| 98 | 461 | 81 |
| 99 | 423 | 67 |

EXAMPLE 100

Preparation of 2-(2-{4-[1-(2-ethoxyethyl)-7-hydroxy-1H-pyrrolo[2,3-b]pyridin-3-yl]-piperidin-1-yl}-ethoxy-benzoic acid Over a solution of 0.15 g (0.68 mmol) of 3-chloroperbenzoic acid in 3 ml of dichloromethane at 0° C., a solution of 0.3 g (0.68 mmol) of 2-(2-{4-[1-(2-ethoxyethyl)-1H-pyrrolo[2,3-b]pyridin-3-yl]-piperidin-1-yl}-ethoxy)benzoic acid in 10 ml of dichloromethane was slowly added. After 2 hours at 0° C., the crude mixture was diluted with 15 ml of dichloromethane and washed with brine. The organic phase was dried over magnesium sulphate, filtered and the solvent was removed over reduced pressure. The crude mixture was purified by chromatography over silica gel affording 0.14 g (46% yield) of 2-(2-{4-[1-(2-ethoxyethyl)-7-hydroxy-1H-pyrrolo[2,3-b]pyridin-3-yl]-piperidin-1-yl}ethoxy)-benzoic acid.

Melting point=173.8-175.1° C.

NMR (300 MHz, DMSO-d6) δ=1.01-1.06 (t, 3H), 1.95-1.99 (m, 2H), 2.22-2.33 (m, 2H), 3.01-3.09 (t, 1H), 3.38-3.45 (q, 2H), 3.57-3.73 (m, 6H), 3.79-3.89 (m, 2H), 4.33-4.37 (t, 2H), 4.59.4.77 (m, 2H), 6.95-6.99 (t, 1H), 7.06-7.09 (dd, 1H), 7.16-7.19 (m, 1H), 7.32-7.39 (m, 3H), 7.98-8.01 (d, 1H), 8.22-8.24 (d, 1H).

Also included within the scope of the present invention are pharmaceutical compositions which comprise, as the active ingredient, at least one azaindolylpiperidine derivative of general formula I, or a pharmaceutically acceptable salt thereof, in association with a pharmaceutically acceptable carrier or diluent. Preferably the composition is made up in a form suitable for oral, or parenteral administration. The pharmaceutically acceptable carriers or diluents which are mixed with the active compound or compounds, or salts thereof, to form the composition of this invention are well-known "per se" and the actual excipients used depend "inter alia" on the intended method of administration of the compositions.

Compositions of this invention are preferably adapted for oral administration. In this case, the compositions may take the form of tablets, capsules or effervescent granules or of liquid preparations such as elixirs, syrups or suspensions, all containing one or more compounds of the invention; such preparations may be made by methods well known in the art. The diluents which may be used in the preparation of the compositions include those liquid and solid diluents which are compatible with the active ingredient, together with colouring or flavouring agents, if desired.

Tablets or capsules may conveniently contain between 0.2 and 500 mg, preferably from 0.5 to 100 mg, of active ingredient or the equivalent amount of a pharmaceutically acceptable salt thereof. The compounds may be incorporated into pellets coated with an appropriate natural or synthetic polymer known in the art to produce sustained release characteristics. They can also be incorporated with polymers into tablet form to produce the same characteristics.

The liquid composition adapted for oral use may be in the form of solution or suspension. The solution may be an aqueous solution of an acid addition salt of the azaindolylpiperidine derivative in association with, for example, sucrose or sorbitol to form a syrup. The suspension may comprise an insoluble or microencapsulated form of an active compound of the invention in association with water or other pharmaceutically acceptable liquid medium together with a suspending agent or flavouring agent.

Compositions for parenteral injection may be prepared from soluble salts of the azaindolylpiperidine derivatives, which may or may not be freeze-dried and which may be dissolved in water or an appropriate parenteral injectable fluid.

In human therapy, the doses of the compound of general formula I depend on the desired effect and duration of treatment; adult doses are generally between 0.2 mg and 500 mg per day and preferably between 0.5 mg and 100 mg per day. In general, the physician will decide the dosing regime taking into account the age and weight of the patient being treated.

Pharmacological Action

The following assays were carried out to demonstrate the excellent pharmacological activities of the compounds of the present invention.

(1) In vitro histamine $H_1$ receptor binding assay, to measure the affinity of the compounds.

(2) Histamine-induced skin vascular permeability in rats, to evaluate antiallergic activity.

(3) $H_1$ ex vivo binding studies in mice, to assess the degree of penetration into the central nervous system.

(4) Measurement of blood pressure and heart rate in conscious unrestrained hypertensive rats, to monitor cardiovascular effects.

(1) Histamine-$H_1$ Receptor Binding Assay

The study of binding to histamine-$H_1$ receptors was performed in guinea pig cerebellum membranes as described previously (Chang et al., *J. Neurochem*, 1979, 32, 1653-1663). Briefly, the membrane suspensions (160 µg/ml) were incubated at 30° C. with 0.7 nM [$^3$H]-mepyramine and different concentrations of the test compounds in a final volume of 250 µl. Binding reactions were terminated by filtration after 30 min of incubation and the bound radioactivity was determined. The non-specific binding was measured in the presence of 10 µM of promethazine. The affinity of each test compound to the receptor was determined by using at least six different concentrations run in duplicate. $IC_{50}$ values were obtained by non-linear regression by use of SAS on a DEC AXP computer.

TABLE 13

Histamine-$H_1$ receptor binding assay

| Compound | Binding to histamine $H_1$ receptor ($IC_{50}$, nM) |
|---|---|
| Cetirizine | 226 |
| Fexofenadine | 214 |
| Loratadine | 360 |
| 1 | 240 |
| 2 | 560 |
| 3 | 225 |
| 4 | 403 |
| 5 | 695 |
| 6 | 190 |
| 7 | 205 |
| 8 | 405 |
| 9 | 150 |
| 10 | 335 |
| 11 | 505 |
| 14 | 510 |
| 17 | 265 |
| 18 | 315 |
| 19 | 500 |
| 22 | 235 |
| 23 | 275 |
| 24 | 475 |
| 25 | 235 |
| 26 | 275 |
| 28 | 520 |
| 36 | 160 |
| 37 | 155 |
| 43 | 120 |
| 44 | 70 |
| 45 | 255 |
| 50 | 48 |
| 54 | 695 |
| 61 | 100 |
| 63 | 110 |
| 64 | 380 |
| 73 | 111 |
| 76 | 675 |

TABLE 13-continued

Histamine-$H_1$ receptor binding assay

| Compound | Binding to histamine $H_1$ receptor ($IC_{50}$, nM) |
|---|---|
| 81 | 220 |
| 84 | 74 |
| 92 | 105 |
| 96 | 805 |

Our results show that the compounds of the present invention have affinities for the $H_1$ receptors very similar to the reference compounds cetirizine, fexofenadine and loratadine.

(2) Histamine-Induced Skin Vascular Permeability in Rats

Male Wistar rats (180-210 g) were treated orally with the test compound or vehicle. Either one, four, eight or 24 hours later the rats were lightly anaesthetized with ether and a cutaneous reaction was induced by two intradermal injections of 50 µl of histamine (100 µg/ml) onto the back, followed by a intravenous injection of 3 ml/kg of Evan's Blue (5 mg/ml), both dissolved in saline. Sixty minutes later, the rats were killed by cervical dislocation and the back skin dissected free. The diameter (in millimetres) of the papule was measured in two directions and the area was calculated. Results are given as the % of inhibition at a given dose compared with the vehicle treated group.

The compounds disclosed in examples 1, 2, 3, 4, 5, 6, 7, 8, 9, 10, 19, 24, 25, 36, 44 and 61 produced an inhibition greater than 50% of the vascular permeability induced by histamine four hours after administration of a dose of 3 mg/Kg of the compounds of the invention. Under the same experimental conditions, cetirizine and fexofenadine produced an inhibition of 36% and 21%, respectively.

(3) Histamine-$H_1$ Receptor Ex Vivo Binding Studies in Mice

The assay was performed essentially as described by Leysen et al (*Drug Development Research* 1991, 22, 165-178) with the following modifications. Overnight starved male Swiss albino mice (21±2 g) were treated orally with different doses of the test compounds (10 ml/kg, p.o.) and 90 minutes later were killed. The whole brain was dissected out and homogenized in 10 ml of ice-cold 0.05 M $Na^+/K^+$ phosphate buffer (pH 7.4). A 1 ml aliquot of the homogenate was incubated, in triplicate, with 0.1 ml [$^3$H]-mepyramine (2 nM final concentration, 27 Ci/mmol, Amersham) during 40 minutes at 30° C. The concentration of [$^3$H]-mepyramine bound to the membranes was determined by immediate filtration of the homogenates under vacuum onto glass fibre filters (Whatman GF/B) followed by three rapid rinses with 5 ml of cold buffer containing 10 µM cold mepyramine. The radioactivity bound in the filters was determined by liquid scintillation spectrometry. The non-specific binding was determined by treating the animals with 30 mg/kg p.o. D-chlorpheniramine maleate. Mice treated with vehicle (methylcellulose 0.5% and tween 0.1%) were used to determine the total binding.

The results of this assay, expressed as a percentage of specific binding at a given dose of the test compound, show that the compounds of the present invention display little or no penetration through the blood brain barrier.

(4) Measurement of Blood Pressure and Heart Rate in Conscious Unrestrained Hypertensive Rats Blood pressure sensors were implanted just above the iliac bifurcation in the abdominal aorta of adult male spontaneously hypertensive rats (SHR). After recovery from anaesthesia, rats were housed individually in cages placed on radiofrequency receivers. Amoxicillin (15 mg/kg, i.m., after surgery) was administered to prevent infection. The rats were allowed to recover for at least 2 weeks after transmitter implantation. Arterial blood pressure and heart rate were recorded and analysed by Dataquest V system (Data Science, St. Paul, Minn.). The animals were kept on a 12:12 hours light-dark cycle during the entire recording period. After 18 hours of fasting with water "ad libitum", the animals received drugs orally and were then given food. Hemodynamic recordings were taken every 15 minutes, starting 4 hours before drug administration and continuing up to 24 hours after. Each recording lasted 10 seconds, and the hemodynamic values of all cycles within this period were averaged. All the animals received all the treatments. Between administrations to the same rat there was a seven day wash-out period, and a complete recovery to base-line values was ascertained. The effects of the treatments on mean arterial blood pressure and heart rate were determined with one-way analysis of variance (ANOVA). A P value <0.05 was considered statistically significant.

The compounds of the present invention have little or no effects on blood pressure and heart rate at doses from 3 to 30 mg/kg.

The above described results show that the compounds of the present invention have excellent antihistamine and antiallergic activities, which are at least comparable, and in many cases better, than those of the commercial antihistamines used as reference.

At the same time, the compounds of the present invention have reduced cardiovascular and central nervous system side effects. They can thus be advantageously used for the treatment of allergic disorders, for instance, bronchial asthma, rhinitis, conjunctivitis, dermatitis and urticaria.

The invention thus provides a method for treating an allergic disorder comprising the step of administering to a subject in need of such treatment an effective amount of a compound of formula I.

The invention also provides the use of the compounds of formula I in the manufacture of a medicament for the treatment of an allergic, disorder, as well as pharmaceutical compositions comprising a compound of formula I. Some examples of suitable compositions are shown below.

EXAMPLE 101

Preparation of a Pharmaceutical Composition: Syrup 1000 bottles (150 ml volume) each containing a solution of 750 mg of 5-[4-(1-isopropyl-1H-pyrrolo[2,3-b]pyridin-3-yl) piperidin-1-ylmethyl]-2-methoxy-benzoic acid were prepared as follows:

| | |
|---|---|
| 5-[4-(1-isopropyl-1H-pyrrolo[2,3-b]pyridin-3-yl)- piperidin-1-ylmethyl]-2-methoxy-benzoic acid | 750 g |
| glycerin | 15,000 g |
| hydrogenated castor oil-ethylene oxide | 1,500 g |
| sodium methyl p-hydroxybenzoate | 240 g |
| sodium propyl p-hydroxybenzoate | 60 g |
| sodium saccharin | 300 g |
| flavouring q.s. | |
| sodium hydroxide q.s. pH = 4 | |
| demineralised water q.s. 150 litres | |

Procedure:

To a solution of the p-hydroxybenzoates and saccharin in 30 litres of demineralised water, an aqueous glycerin solution and hydrogenated castor oil-ethylene oxide were added. After stirring, the 5-[4-(1-isopropyl-1H-pyrrolo[2,3-b]pyridin-3-yl)-piperidin-1-ylmethyl]-2-methoxy-benzoic acid was added and homogenised to reach complete dissolution. After this, the flavouring agent was mixed into the solution with vigorous stirring, and the mixture was made up to final volume with demineralised water.

The resultant solution was filled into 150 ml bottles using an appropriate filling machine.

EXAMPLE 102

Preparation of a Pharmaceutical Composition: Capsules 50,000 capsules each containing 50 mg of 2-methoxy-5-{4-[1-(2-methoxy-ethyl)-1H-pyrrolo[2,3-b]pyridin-3-yl]-piperidin-1-ylmethyl}-benzoic acid were prepared from the following formulation:

| | |
|---|---|
| 2-methoxy-5-{4-[1-(2-methoxy-ethyl)-1H-pyrrolo[2,3-b]pyridin-3-yl]-piperidin-1-ylmethyl}-benzoic acid | 2,500 g |
| magnesium stearate | 225 g |
| lactose spray dried | 18,350 g |
| cross-linked sodium carboxymethylcellulose | 900 g |
| sodium lauryl sulphate | 450 g |

Procedure:

2-methoxy-5-{4-[1-(2-methoxy-ethyl)-1H-pyrrolo[2,3-b]pyridin-3-yl]-piperidin-1-ylmethyl}-benzoic acid, sodium lauryl sulphate, lactose and cross-linked sodium carboxymethylcellulose were mixed together and passed through a screen with an opening of 0.6 mm. The magnesium stearate was added and the mixture encapsulated into gelatine capsules of appropriate size.

EXAMPLE 103

Preparation of a Pharmaceutical Composition: Tablets 100,000 tablets each containing 25 mg of 2-{2-[4-(1-furan-3-ylmethyl-1H-pyrrolo[2,3-c]pyridin-3-yl)-piperidin-1-yl]-ethoxy}-benzoic acid were prepared from the following formulation:

| | |
|---|---|
| 2-{2-[4-(1-furan-3-ylmethyl-1H-pyrrolo[2,3-c]pyridin-3-yl)-piperidin-1-yl]-ethoxy}-benzoic acid | 2,500 g |
| microcrystalline cellulose | 1,650 g |
| lactose spray dried | 9,620 g |
| carboxymethyl starch | 570 g |
| sodium stearyl fumarate | 80 g |
| colloidal silicon dioxide | 80 g |

Procedure:

All the powders were passed through a screen with apertures of 0.6 mm. They were then all mixture in a suitable mixer for 30 minutes and compressed into 145 mg tablets using 6 mm discs and flat bevelled punches. The disintegration time of the tablets was about 60 seconds.

The invention claimed is:

1. A compound of formula I

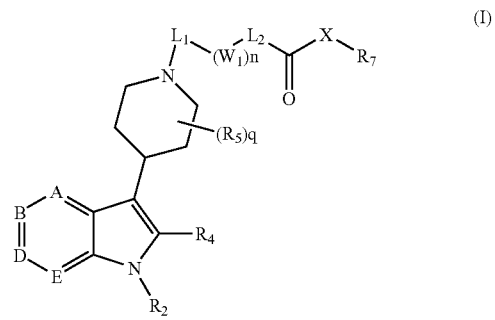

wherein:
each of A, B, D and E independently represents a nitrogen atom or a —$CR_1$-group, with the proviso that only one of A, B, D or E is a nitrogen atom;

$R_1$ represents a hydrogen or a halogen atom, or a hydroxy, alkyl, alkenyl, alkynyl, alkoxy, alkylthio, amino, monalkylamino, dialkylamino, nitro, cyano or acylamino group,
wherein a hydrocarbon chain in $R_1$ is optionally substituted by one or more further substituents chosen from halogen, hydroxy, oxo, alkoxy, alkylthio, acylamino, phenyl, alkoxycarbonyl, amino, monoalkylamino, dialkylamino and hydroxycarbonyl groups;

$R_2$ represents a group of formula $L_3$—$(W_2)_p$;

$L_1$, $L_2$ and $L_3$ each independently represents a single bond or an acyclic, straight or branched, saturated or unsaturated hydrocarbon chain having from 1 to 10 carbon atoms, optionally containing 1 to 3 groups independently chosen from —S—, —O— and —$NR_3$—, which replace a corresponding number of non-adjacent carbon atoms,
wherein
p represents 0 or 1;
when $L_3$ is a single bond, p is 1;

$R_3$ is chosen from hydrogen and an alkyl group; and
wherein a hydrocarbon chain in $L_1$, $L_2$ or $L_3$ is optionally substituted by one or more substituents chosen from halogen, hydroxy, oxo, acylamino, phenyl, alkoxycarbonyl and hydroxycarbonyl groups;

$R_4$ and $R_5$ each independently represents a hydrogen or halogen atom, a hydroxy group, or a group chosen from alkyl, alkoxy, alkenyl, alkynyl and phenyl, wherein each of said alkyl, alkoxy, alkenyl, alkynyl or phenyl groups is independently optionally substituted by one or more substituents chosen from halogen, hydroxy, oxo, alkoxy, alkylthio, acylamino, phenyl, alkoxycarbonyl, amino, monoalkylamino, dialkylamino and hydroxycarbonyl groups;

X represents —O— or —$NR_6$—;

$R_6$ and $R_7$ each independently represents a hydrogen atom, a group of formula —$(CH_2)_m$—$W_3$ or a group chosen from alkyl, alkenyl and alkynyl, wherein each of said alkyl, alkenyl or alkynyl groups is independently optionally substituted by one or more substituents chosen from —$(CH_2)_m$—$W_3$, —O—$(CH_2)_m$—$W_3$, S—$(CH_2)_m$—$W_3$, —$NR_3$—$(CH_2)_m$—$W_3$, hydroxy, oxo, halogen, alkoxy, alkylthio, amino, monoalkylamino, and dialkylamino;

wherein each of the alkyl chains in the alkoxy, alkylthio, monoalkylamino and dialkylamino substituents is independently optionally substituted by one or more further substituents chosen from —$(CH_2)_m$—$W_3$, hydroxy, oxo, halogen, alkoxy, alkylthio, amino, monoalkylamino and dialkylamino groups;

$W_1$, $W_2$ and $W_3$ each independently represents a 3- to 7-membered aromatic or nonaromatic cyclic group containing from 0 to 4 heteroatoms chosen from N, O and S, wherein the 3- to 7-membered aromatic or nonaromatic cyclic group is independently optionally fused to another 3- to 7-membered aromatic or non-aromatic cyclic group containing from 0 to 4 heteroatoms chosen from N, O and S;

wherein each cyclic group is independently optionally substituted by one or more substituents chosen from halogen, alkyl, alkenyl, alkynyl, aryl, cycloalkyl, heteroaryl, heterocyclic, hydroxy, alkylenedioxy, alkoxy, alkylthio, amino, monoalkylamino, dialkylamino, nitro, cyano, oxo, hydroxycarbonyl, alkylcarbonyl, alkoxycarbonyl, acylamino, carbamoyl, and alkylcarbamoyl groups;

wherein each of the hydrocarbon chains and the cyclic moieties of these substituents is independently optionally substituted by one or more further substituents chosen from halogen, hydroxy, oxo, alkoxy, alkylthio, acylamino, carbamoyl, alkylcarbamoyl, hydroxyalkoxy, phenyl, alkoxycarbonyl, amino, monoalkylamino, dialkylamino and hydroxycarbonyl groups;

m is an integer from 0 to 4;
n represents 0 or 1;
q is an integer from 1 to 9;
or a N-oxide or a pharmaceutically acceptable salt thereof, with the proviso that the compound of formula I is not the tert-butyl ester of 4-(5-amino-1H-pyrrolo[3,2-b]pyridin-3-yl)-piperidine-1-carboxylic acid.

2. A compound according to claim 1, wherein only one of D or E is a nitrogen atom.

3. A compound according to claim 1, wherein each $R_1$, is independently chosen from a hydrogen atom, a halogen atom, an alkyl group, and an alkoxy group.

4. A compound according to claim 3, wherein $R_1$, is hydrogen, chlorine, fluorine or methoxy.

5. A compound according to claim 1, wherein each of $L_1$, $L_2$ and $L_3$ independently represents a single bond or an alkyl, oxyalkyl, aminoalkyl, thioalkyl or alkoxyalkyl group.

6. A compound according to claim 5, wherein $L_1$ is an alkyl, oxyalkyl, aminoalkyl or thioalkyl group; $L_2$ is a single bond or an alkyl group; and $L_3$ is a single bond or an alkyl, oxyalkyl or alkoxyalkyl group.

7. A compound according to claim 6, wherein $L_1$ is methyl, ethyl, n-propyl, oxyethyl, oxypropyl, aminoethyl or thioethyl; $L_2$ is a single bond, methyl or ethyl; and $L_3$ is a single bond, methyl, ethyl, n-propyl, isopropyl, butyl, oxyethyl, methoxyethyl or ethoxyethyl.

8. A compound according to claim 1, wherein $W_1$ is an aromatic monocyclic group, which is optionally substituted by one or more substituents chosen from halogen atoms, alkyl and alkoxy groups.

9. A compound according to claim 8, wherein $W_1$ is a phenyl, furanyl or thienyl group, and wherein $W_1$ is optionally substituted by one or more substituents chosen from fluorine, chlorine, bromine, methyl and methoxy.

10. A compound according to claim 1, wherein n is O.

11. A compound according to claim 1, wherein $W_2$ is a cycloalkyl group, a phenyl group, or a 5- or 6-membered heterocyclyl group, and wherein $W_2$ is optionally substituted by one or more substituents chosen from halogen, alkyl and alkoxy.

12. A compound according to claim 11, wherein $W_2$ is a cyclic group chosen from cyclopropyl, cyclobutyl, cyclopentyl, phenyl, tetrahydropyranyl, furanyl, thienyl, pyrrolyl, pyridinyl, oxetanyl and dioxanyl, and is optionally substituted by one or more substituents chosen from fluorine, chlorine, bromine, methyl, ethyl and methoxy.

13. A compound according to claim 1, wherein p is 0.

14. A compound according to claim 1, wherein $R_4$ and $R_5$ each independently represents a hydrogen or halogen atom, a $C_1$-$C_4$ alkyl group or a phenyl group, which is optionally substituted by one or more substituents chosen from halogen, alkyl and alkoxy.

15. A compound according to claim 14, wherein $R_4$ and $R_5$ are both hydrogen.

16. A compound according to claim 1, wherein X is —O— and $R_7$ is hydrogen, alkyl or a —$(CH_2)_n$-phenyl group, and wherein n is 0 or 1.

17. A compound according to claim 16, wherein $R_7$ is hydrogen, methyl, ethyl, tert-butyl, phenyl or benzyl.

18. A compound according to claim 1, wherein X is —N—$R_6$, and $R_6$ and $R_7$ are independently hydrogen, alkyl or a —$(CH_2)_n$-phenyl group, and wherein n is 0 or 1.

19. A compound according to claim 18, wherein $R_6$ and $R_7$ are independently hydrogen, methyl, ethyl, tert-butyl, phenyl or benzyl.

20. A compound according to claim 1 chosen from:
3-{4-[1-(2-methoxyethyl)-1H-pyrrolo[2,3-b]pyridin-3-yl]piperidin-1-ylmethyl}benzoic acid;
3-[4-(1-furan-3-ylmethyl-1H-pyrrolo[2,3-b]pyridin-3-yl)piperidin-1-ylmethyl]benzoic acid;
2-{2-[4-(1-furan-3-ylmethyl-1H-pyrrolo[2,3-b]pyridin-3-yl)piperidine-1-yl]ethoxy}benzoic acid;
3-{4-[1-(2-ethoxyethyl)-1H-pyrrolo[2,3-b]pyridine-3-yl]piperidin-1-ylmethyl}benzoic acid;
5-{4-[1-(2-ethoxyethyl)-1H-pyrrolo[2,3-b]pyridine-1-ylmethyl}-2-methoxybenzoic acid;
2-(2-{4-[1-(2-ethoxyethyl)-1H-pyrrolo[2,3-b]pyridin-3-yl]piperidin-1-ylethoxy)benzoic acid;
5-[4-(1-furan-3-ylmethyl-1H-pyrrolo[2,3-b]pyridin-3-yl)-piperidin-1-ylmethyl]-2-methoxybenzoic acid;
2-{2-[4-(1-furan-2-ylmethyl-1H-pyrrolo[2,3-b]pyridin-3-yl)-piperidin-1-yl]-ethoxy}-benzoic acid;
3-[4-(1-furan-2-ylmethyl-1H-pyrrolo[2,3-b]pyridin-3-yl)-piperidin-1-ylmethyl]-benzoic acid;
5-[4-(1-furan-2-ylmethyl-1H-pyrrolo[2,3-b]pyridin-3-yl)-piperidin-1-ylmethyl]-2-methoxy-benzoic acid;
2-{2-[4-(1-thiophen-2-ylmethyl-1H-pyrrolo[2,3-b]pyridin-3-yl)-piperidin-1-yl]-ethoxy}-benzoic acid;
3-[4-(1-thiophen-2-ylmethyl-1H-pyrrolo[2,3-b]pyridin-3-yl)-piperidin-1-ylmethyl]-benzoic acid;
2-methoxy-5-[4-(1-thiophen-2-ylmethyl-1H-pyrrolo[2,3-b]pyridin-3-yl)-piperidin-1-ylmethyl]-benzoic acid;
2-{2-[4-(1-thiophen-3-ylmethyl-1H-pyrrolo[2,3-b]pyridin-3-yl)-piperidin-1-yl]-ethoxy}-benzoic acid;
3-[4-(1-thiophen-3-ylmethyl-1H-pyrrolo[2,3-b]pyridin-3-yl)-piperidin-1-ylmethyl]-benzoic acid;
2-methoxy-5-[4-(1-thiophen-3-ylmethyl-1H-pyrrolo[2,3-b]pyridin-3-yl)-piperidin-1-ylmethyl]-benzoic acid;
2-(2-{4-[1-(5-chlorothiophen-2-ylmethyl)-1H-pyrrolo[2,3-b]pyridin-3-yl]-piperidin-1-yl}-ethoxy)-benzoic acid;
3-{4-[1-(5-chlorothiophen-2-ylmethyl)-1H-pyrrolo[2,3-b]pyridin-3-yl]-piperidin-1-ylmethyl}-benzoic acid;

5-{4-[1-(5-chlorothiophen-2-ylmethyl)-1H-pyrrolo[2,3-b]pyridin-3-yl]-piperidin-1-ylmethyl}-2-methoxybenzoic acid;
2-(2-{4-[1-(2-methoxyethyl)-1H-pyrrolo[2,3-b]pyridin-3-yl]-piperidin-1-yl}-ethoxy)-benzoic acid;
2-methoxy-5-{4-[1-(2-methoxyethyl)-1H-pyrrolo[2,3-b]pyridin-3-yl]-piperidin-1-ylmethyl}-benzoic acid;
2,4-dimethoxy-3-{4-[1-(2-methoxyethyl)-1H-pyrrolo[2,3-b]pyridin-3-yl]-piperidin-1-ylmethyl}-benzoic acid;
2-methoxy-6-(2-{4-[1-(2-methoxyethyl)-1H-pyrrolo[2,3-b]pyridin-3-yl]-piperidin-1-yl}-ethoxy)-benzoic acid;
5-[4-(1-butyl-1H-pyrrolo[2,3-b]pyridin-3-yl)-piperidin-1-ylmethyl]-2-methoxybenzoic acid;
2-{2-[4-(1-butyl-1H-pyrrolo[2,3-b]pyridin-3-yl)-piperidin-1-yl]-ethoxy}-benzoic acid;
3-[4-(1-butyl-1H-pyrrolo[2,3-b]pyridin-3-yl)-piperidin-1-ylmethyl]-benzoic acid
2-{2-[4-(1-cyclopropylmethyl-1H-pyrrolo[2,3-b]pyridin-3-yl)-piperidin-1-yl]-ethoxy}-benzoic acid;
3-[4-(1-cyclopropylmethyl-1H-pyrrolo[2,3-b]pyridin-3-yl)-piperidin-1-ylmethyl]-benzoic acid;
5-[4-(1-cyclopropylmethyl-1H-pyrrolo[2,3-b]pyridin-3-yl)-piperidin-1-ylmethyl]-2-methoxybenzoic acid;
2-{2-[4-(1-isopropyl-1H-pyrrolo[2,3-b]pyridin-3-yl)-piperidin-1-yl]-ethoxy}-benzoic acid;
3-[4-(1-isopropyl-1H-pyrrolo[2,3-b]pyridin-3-yl)-piperidin-1-ylmethyl]-benzoic acid;
5-[4-(1-isopropyl-1H-pyrrolo[2,3-b]pyridin-3-yl)-piperidin-1-ylmethyl]-2-methoxybenzoic acid;
2-(2-{4-[1-(4-fluorobenzyl)-1H-pyrrolo[2,3-b]pyridin-3-yl]-piperidin-1-yl}-ethoxy)-benzoic acid;
4-{4-[1-(4-fluorobenzyl)-1H-pyrrolo[2,3-b]pyridin-3-yl]-piperidin-1-yl}-butyric acid;
(2-{4-[1-(4-fluorobenzyl)-1H-pyrrolo[2,3-b]pyridin-3-yl]-piperidin-1-yl}-ethoxy)-acetic acid;
2-(2-{4-[1-(2-ethoxyethyl)-1H-pyrrolo[2,3-b]pyridin-3-yl]-piperidin-1-yl}-ethoxy)-4-methoxybenzoic acid;
2-(2-{4-[1-(2-ethoxyethyl)-1H-pyrrolo[2,3-b]pyridin-3-yl]-piperidin-1-yl}-ethoxy)-3-methoxybenzoic acid;
4-chloro-2-(2-{4-[1-(2-ethoxyethyl)-1H-pyrrolo[2,3-b]pyridin-3-yl]-piperidin-1-yl}-ethoxy)-benzoic acid;
5-{4-[1-(2-ethoxyethyl)-1H-pyrrolo[2,3-b]pyridin-3-yl]-piperidin-1-ylmethyl}-2-fluorobenzoic acid;
3-{4-[1-(2-ethoxyethyl)-1H-pyrrolo[2,3-b]pyridin-3-yl]-piperidin-1-ylmethyl}-2-methoxybenzoic acid;
3-{4-[1-(2-ethoxyethyl)-1H-pyrrolo[2,3-b]pyridin-3-yl]-piperidin-1-ylmethyl}-2,4-dimethoxybenzoic acid;
2-(2-{4-[1-(2-ethoxyethyl)-1H-pyrrolo[2,3-b]pyridin-3-yl]-piperidin-1-yl}-ethoxy)-6-methoxybenzoic acid;
2-{2-[4-(1-furan-3-ylmethyl-1H-pyrrolo[2,3-b]pyridin-3-yl)-piperidin-1-yl]-ethoxy}-4-methoxybenzoic acid;
4-chloro-2-{2-[4-(1-furan-3-ylmethyl-1H-pyrrolo[2,3-b]pyridin-3-yl)-piperidin-1-yl]-ethoxy}-benzoic acid;
2-fluoro-5-[4-(1-furan-3-ylmethyl-1H-pyrrolo[2,3-b]pyridin-3-yl)-piperidin-1-ylmethyl]-benzoic acid;
2-{2-[4-(1-furan-3-ylmethyl-1H-pyrrolo[2,3-b]pyridin-3-yl)-piperidin-1-yl]-ethoxy}-3-methoxybenzoic acid;
3-[4-(1-furan-3-ylmethyl-1H-pyrrolo[2,3-b]pyridin-3-yl)-piperidin-1-yl]-ethoxy)-2-methoxybenzoic acid
3-[4-(1-furan-3-ylmethyl-1H-pyrrolo[2,3-b]pyridin-3-yl)-piperidin-1-ylmethyl]-2,4-dimethoxybenzoic acid;
2-{2-[4-(1-furan-3-ylmethyl-1H-pyrrolo[2,3-b]pyridin-3-yl)-piperidin-1-yl]-ethoxy}-6-methoxybenzoic acid;
2-{2-[4-(1-furan-2-ylmethyl-1H-pyrrolo[2,3-b]pyridin-3-yl)-piperidin-1-yl]-ethoxy}-4-methoxybenzoic acid;
2-{2-[4-(1-furan-2-ylmethyl-1H-pyrrolo[2,3-b]pyridin-3-yl)-piperidin-1-yl]-ethoxy}-3-methoxybenzoic acid;
4-chloro-2-{2-[4-(1-furan-2-ylmethyl-1H-pyrrolo[2,3-b]pyridin-3-yl)-piperidin-1-yl]-ethoxy}-benzoic acid;
2-fluoro-5-[4-(1-furan-2-ylmethyl-1H-pyrrolo[2,3-b]pyridin-3-yl)-piperidin-1-ylmethyl]-benzoic acid;
2-(2-{4-[1-(5-chlorothiophen-2-ylmethyl)-1H-pyrrolo[2,3-b]pyridin-3-yl]-piperidin-1-yl}-ethoxy)-3-methoxybenzoic acid;
2-(2-{4-[1-(5-chlorothiophen-2-ylmethyl)-1H-pyrrolo[2,3-b]pyridin-3-yl]-piperidin-1-yl}-ethoxy)-4-methoxybenzoic acid;
4-chloro-2-(2-{4-[1-(5-chlorothiophen-2-ylmethyl)-1H-pyrrolo[2,3-b]pyridin-3-yl]-piperidin-1-yl}-ethoxy)-benzoic acid;
5-{4-[1-(5-chlorothiophen-2-ylmethyl)-1H-pyrrolo[2,3-b]pyridin-3-yl]-piperidin-1-ylmethyl}-2-fluorobenzoic acid;
3-{4-[1-(5-chlorothiophen-2-ylmethyl)-1H-pyrrolo[2,3-b]pyridin-3-yl]-piperidin-1-ylmethyl}-2-methoxybenzoic acid;
3-{4-[1-(5-chlorothiophen-2-ylmethyl)-1H-pyrrolo[2,3-b]pyridin-3-yl]-piperidin-1-ylmethyl}-2,4-dimethoxybenzoic acid;
2-(2-{4-[1-(5-chlorothiophen-2-ylmethyl)-1H-pyrrolo[2,3-b]pyridin-3-yl]-piperidin-1-yl}-ethoxy)-6-methoxybenzoic acid;
2-{2-[4-(1-butyl-1H-pyrrolo[2,3-b]pyridin-3-yl)-piperidin-1-yl]-ethoxy}-4-methoxybenzoic acid;
2-{2-[4-(1-butyl-1H-pyrrolo[2,3-b]pyridin-3-yl)-piperidin-1-yl]-ethoxy}-3-methoxybenzoic acid;
2-{2-[4-(1-butyl-1H-pyrrolo[2,3-b]pyridin-3-yl)-piperidin-1-yl]-ethoxy}-4-chlorobenzoic acid;
5-[4-(1-butyl-1H-pyrrolo[2,3-b]pyridin-3-yl)-piperidin-1-ylmethyl]-2-fluorobenzoic acid;
3-[4-(1-butyl-1H-pyrrolo[2,3-b]pyridin-3-yl)-piperidin-1-ylmethyl]-2-methoxybenzoic acid;
3-[4-(1-butyl-1H-pyrrolo[2,3-b]pyridin-3-yl)-piperidin-1-ylmethyl]-2,4-dimethoxybenzoic acid;
2-{2-[4-(1-butyl-1H-pyrrolo[2,3-b]pyridin-3-yl)-piperidin-1-yl]-ethoxy}-6-methoxybenzoic acid;
2-{2-[4-(1-pyridin-2-ylmethyl-1H-pyrrolo[2,3-b]pyridin-3-yl)-piperidin-1-yl]-ethoxy}-benzoic acid;
4-[4-(1-pyridin-2-ylmethyl-1H-pyrrolo[2,3-b]pyridin-3-yl)-piperidin-1-yl]-butyric acid;
2-(2-{4-[1-(2-ethoxyethyl)-1H-pyrrolo[2,3-c]pyridin-3-yl]-piperidin-1-yl}-ethoxy)-benzoic acid;
2-(2-{4-[1-(2-ethoxyethyl)-1H-pyrrolo[2,3-c]pyridin-3-yl]-piperidin-1-yl}-ethoxy)-3-methoxybenzoic acid;
2-(2-{4-[1-(2-ethoxyethyl)-1H-pyrrolo[2,3-c]pyridin-3-yl]-piperidin-1-yl}-ethoxy)-4-methoxybenzoic acid;
4-chloro-2-(2-{4-[1-(2-ethoxyethyl)-1H-pyrrolo[2,3-c]pyridin-3-yl]-piperidin-1-yl}-ethoxy)-benzoic acid;
5-{4-[1-(2-ethoxyethyl)-1H-pyrrolo[2,3-c]pyridin-3-yl]-piperidin-1-ylmethyl}-2-methoxybenzoic acid;
4-bromo-3-{4-[1-(2-ethoxyethyl)-1H-pyrrolo[2,3-c]pyridin-3-yl]-piperidin-1-ylmethyl}-benzoic acid;
2-{2-[4-(1-furan-3-ylmethyl-1H-pyrrolo[2,3-c]pyridin-3-yl)-piperidin-1-yl]ethoxy}-4-methoxybenzoic acid;
2-{2-[4-(1-furan-3-ylmethyl-1H-pyrrolo[2,3-c]pyridin-3-yl)-piperidin-1-yl]-ethoxy}-benzoic acid;
5-[4-(1-furan-3-ylmethyl-1H-pyrrolo[2,3-c]pyridin-3-yl)-piperidin-1-ylmethyl]-2-methoxybenzoic acid;
3-[4-(1-furan-3-ylmethyl-1H-pyrrolo[2,3-c]pyridin-3-yl)-piperidin-1-ylmethyl]-2-methoxybenzoic acid;
4-chloro-2-{2-[4-(1-furan-3-ylmethyl-1H-pyrrolo[2,3-c]pyridin-3-yl)-piperidin-1-yl]-ethoxy}benzoic acid;
2-{2-[4-(1-butyl-1H-pyrrolo[2,3-c]pyridin-3-yl)-piperidin-1-yl]-ethoxy}-benzoic acid;

2-{2-[4-(1-butyl-1H-pyrrolo[2,3-c]pyridin-3-yl)-piperidin-1-yl]-ethoxy}-3-methoxy-benzoic acid;
2-{2-[4-(1-butyl-1H-pyrrolo[2,3-c]pyridin-3-yl)-piperidin-1-yl]-ethoxy}-4-methoxy-benzoic acid;
2-{2-[4-(1-butyl-1H-pyrrolo[2,3-c]pyridin-3-yl)-piperidin-1-yl]-ethoxy}-4-chlorobenzoic acid;
5-[4-(1-butyl-1H-pyrrolo[2,3-c]pyridin-3-yl)-piperidin-1-ylmethyl]-2-methoxybenzoic acid;
4-bromo-3-[4-(1-butyl-1H-pyrrolo[2,3-c]pyridin-3-yl)-piperidin-1-ylmethyl]-benzoic acid;
3-[4-(1-butyl-1H-pyrrolo[2,3-c]pyridin-3-yl)-piperidin-1-ylmethyl]-benzoic acid;
5-{4-[1-(5-chlorothiophen-2-ylmethyl)-1H-pyrrolo[2,3-c]pyridin-3-yl]-piperidin-1-ylmethyl}-2-methoxybenzoic acid;
2-(2-{4-[1-(5-chlorothiophen-2-ylmethyl)-1H-pyrrolo[2,3-c]pyridin-3-yl]-piperidin-1-yl}-ethoxy)-benzoic acid;
2-(2-{4-[1-(5-chlorothiophen-2-ylmethyl)-1H-pyrrolo[2,3-c]pyridin-3-yl]-piperidin-1-yl}-ethoxy)-3-methoxy-benzoic acid;
2-(2-{4-[1-(5-chlorothiophen-2-ylmethyl)-1H-pyrrolo[2,3-c]pyridin-3-yl]-piperidin-1-yl}-ethoxy)-4-methoxy-benzoic acid;
4-chloro-2-(2-{4-[1-(5-chlorothiophen-2-ylmethyl)-1H-pyrrolo[2,3-c]pyridin-3-yl]-piperidin-1-yl}-ethoxy)-benzoic acid;
(2-{4-[1-(5-chlorothiophen-2-ylmethyl)-1H-pyrrolo[2,3-c]pyridin-3-yl]-piperidin-1-yl}-ethoxy)-acetic acid;
2-{2-[4-[1-thiophen-2-ylmethyl)-1H-pyrrolo[2,3-c]pyridin-3-yl)-piperidin-1-yl]-ethoxy}-benzoic acid;
2-{2-[4-(1-furan-2-ylmethyl-1H-pyrrolo[2,3-c]pyridin-3-yl)-piperidin-1-yl]ethoxy}-benzoic acid;
5-[4-(1-furan-2-ylmethyl-1H-pyrrolo[2,3-c]pyridin-3-yl)-piperidin-1-ylmethyl]-2-methoxybenzoic acid;
4-methoxy-2-{2-[4-(1-thiophen-3-ylmethyl-1H-pyrrolo[2,3-c]pyridin-3-yl)-piperidin-1-yl]-ethoxy}-benzoic acid;
2-methoxy-5-[4-(1-thiophen-3-ylmethyl-1H-pyrrolo[2,3-c]pyridin-3-yl)-piperidin-1-ylmethyl]-benzoic acid;
2-(2-{4-(1-(2-methoxyethyl)-1H-pyrrolo[2,3-c]pyridin-3-yl]-piperidin-1-yl}-ethoxy)-benzoic acid;
2-(2-{4-[1-(2-ethoxyethyl)-7-hydroxy-1H-pyrrolo[2,3-b]pyridin-3-yl]-piperidin-1-yl}-ethoxy)-benzoic acid;
3-{4-[1-(2-methoxyethyl)-1H-pyrrolo[2,3-b]pyridin-3-yl]piperidin-1-ylmethyl}benzoic acid ethyl ester;
3-[4-(1-furan-3-ylmethyl-1H-pyrrolo[2,3-b]pyridin-3-yl)piperidin-1-ylmethyl]benzoic acid methyl ester;
2-{2-[4-(1-furan-3-ylmethyl-1H-pyrrolo[2,3-b]pyridin-3-yl)piperidine-1-yl]ethoxy}benzoic acid methyl ester;
3-{4-[1-(2-ethoxyethyl)-1H-pyrrolo[2,3-b]pyridine-3-yl]piperidin-1-ylmethyl}benzoic acid methyl ester;
5-{4-[1-(2-ethoxyethyl)-1H-pyrrolo[2,3-b]pyridine-1-ylmethyl}-2-methoxybenzoic acid ethyl ester;
2-(2-{4-[1-(2-ethoxyethyl)-1H-pyrrolo[2,3-b]pyridin-3-yl]piperidin-1-ylethoxy)benzoic acid methyl ester;
5-[4-(1-furan-3-ylmethyl-1H-pyrrolo[2,3-b]pyridin-3-yl)-piperidin-1-ylmethyl]-2-methoxybenzoic acid ethyl ester;
2-(2-{4-[1-(5-chlorothiophen-2-ylmethyl)-1H-pyrrolo[2,3-b]pyridin-3-yl]-piperidin-1-yl}-ethoxy)-benzoic acid methyl ester;
5-[4-(1-butyl-1H-pyrrolo[2,3-b]pyridin-3-yl)-piperidin-1-ylmethyl]-2-methoxybenzoic acid ethyl ester;
2-(2-{4-[1-(2-ethoxyethyl)-1H-pyrrolo[2,3-b]pyridin-3-yl]-piperidin-1-yl}-ethoxy)-4-methoxybenzoic acid methyl ester;
2-(2-{4-[1-(2-ethoxyethyl)-1H-pyrrolo[2,3-c]pyridin-3-yl]-piperidin-1-yl}-ethoxy)-benzoic acid methyl ester;
2-{2-[4-(1-furan-3-ylmethyl-1H-pyrrolo[2,3-c]pyridin-3-yl)-piperidin-1-yl]-ethoxy}-4-methoxy-benzoic acid methyl ester;
2-{2-[4-(1-butyl-1H-pyrrolo[2,3-c]pyridin-3-yl)-piperidin-1-yl]-ethoxy}-benzoic acid methyl ester;
5-{4-[1-(5-chlorothiophen-2-ylmethyl)-1H-pyrrolo[2,3-c]pyridin-3-yl]-piperidin-1-ylmethyl}-2-methoxybenzoic acid ethyl ester;
4-(1-furan-3-ylmethyl-1H-pyrrolo[2,3-b]pyridin-3-yl)-piperidine-1-carboxylic acid tert-butyl ester;
4-(1-furan-3-ylmethyl-1H-pyrrolo[2,3-b]pyridin-3-yl)-piperidine-1-carboxylic acid ethyl ester;
4-[1-(5-chlorothiophen-2-ylmethyl)-1H-pyrrolo[2,3-b]pyridin-3-yl]-piperidine-1-carboxylic acid tert-butyl ester;
4-(1-butyl-1H-pyrrolo[2,3-b]pyridin-3-yl)-piperidine-1-carboxylic acid ethyl ester;
4-[1-(2-ethoxyethyl)-1H-pyrrolo[2,3-c]pyridin-3-yl]-piperidine-1-carboxylic acid ethyl ester;
4-(1-furan-3-ylmethyl-1H-pyrrolo[2,3-c]pyridin-3-yl)-piperidine-1-carboxylic acid ethyl ester;
4-(1-butyl-1H-pyrrolo[2,3-c]pyridin-3-yl)-piperidine-1-carboxylic acid ethyl ester;
4-[1-(5-chlorothiophen-2-ylmethyl)-1H-pyrrolo[2,3-c]pyridin-3-yl]-piperidine-1-carboxylic acid ethyl ester;
4-(1-furan-3-ylmethyl-1H-pyrrolo[2,3-b]pyridin-3-yl)-piperidine-1-carboxylic acid tert-butyl ester;
4-(1-furan-3-ylmethyl-1H-pyrrolo[2,3-b]pyridin-3-yl)-piperidine-1-carboxylic acid ethyl ester;
4-[1-(5-chlorothiophen-2-ylmethyl)-1H-pyrrolo[2,3-b]pyridin-3-yl]-piperidine-1-carboxylic acid tert-butyl ester;
4-(1-butyl-1H-pyrrolo[2,3-b]pyridin-3-yl)-piperidine-1-carboxylic acid ethyl ester;
4-[1-(2-ethoxyethyl)-1H-pyrrolo[2,3-c]pyridin-3-yl]-piperidine-1-carboxylic acid ethyl ester;
4-(1-furan-3-ylmethyl-1H-pyrrolo[2,3-c]pyridin-3-yl)-piperidine-1-carboxylic acid ethyl ester;
4-(1-butyl-1H-pyrrolo[2,3-c]pyridin-3-yl)-piperidine-1-carboxylic acid ethyl ester; and
4-[1-(5-chlorothiophen-2-ylmethyl)-1H-pyrrolo[2,3-c]pyridin-3-yl]-piperidine-1-carboxylic acid ethyl ester;
or a N-oxide or a pharmaceutically acceptable salt thereof.

21. A pharmaceutical composition comprising a compound as claimed in claim 1 and a pharmaceutically acceptable diluent or carrier.

* * * * *

UNITED STATES PATENT AND TRADEMARK OFFICE
CERTIFICATE OF CORRECTION

| | | |
|---|---|---|
| PATENT NO. | : 7,622,480 B2 | Page 1 of 1 |
| APPLICATION NO. | : 10/509279 | |
| DATED | : November 24, 2009 | |
| INVENTOR(S) | : Fonquerna Pou et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1194 days.

Signed and Sealed this

Twenty-sixth Day of October, 2010

David J. Kappos
*Director of the United States Patent and Trademark Office*